(12) United States Patent
Sakamoto et al.

(10) Patent No.: US 8,647,634 B2
(45) Date of Patent: Feb. 11, 2014

(54) RECOMBINANT AVIAN INFECTIOUS CORYZA VACCINE AND PROCESS FOR PREPARING SAME

(75) Inventors: Ryuichi Sakamoto, Kikuchi (JP); Susumu Baba, Kikuchi (JP); Masashi Sakaguchi, Kikuchi (JP); Hiroshi Mizokami, Kikuchi (JP)

(73) Assignee: The Chemo-Sero-Therapeutic Research Institute, Kumamoto-shi (JP)

( * ) Notice: Subject to any disclaimer, the term of this patent is extended or adjusted under 35 U.S.C. 154(b) by 0 days.

(21) Appl. No.: 13/142,178

(22) PCT Filed: Dec. 24, 2009

(86) PCT No.: PCT/JP2009/071398
§ 371 (c)(1),
(2), (4) Date: Jun. 24, 2011

(87) PCT Pub. No.: WO2010/074126
PCT Pub. Date: Jul. 1, 2010

(65) Prior Publication Data
US 2012/0003257 A1    Jan. 5, 2012

(30) Foreign Application Priority Data
Dec. 25, 2008   (JP) ................. 2008-330448

(51) Int. Cl.
*A61K 39/00* (2006.01)
*A61K 39/02* (2006.01)
*A61K 39/12* (2006.01)
*A61K 39/38* (2006.01)
*A01N 63/00* (2006.01)

(52) U.S. Cl.
USPC ... 424/192.1; 424/93.1; 424/93.2; 424/184.1; 424/185.1; 424/190.1; 424/199.1; 424/200.1; 424/203.1; 424/234.1; 424/256.1; 424/278.1

(58) Field of Classification Search
None
See application file for complete search history.

(56) References Cited

U.S. PATENT DOCUMENTS 5,739,292 A    4/1998   Gheysen
5,889,168 A    3/1999   Gheysen
(Continued)

FOREIGN PATENT DOCUMENTS

AU    49273/90 A    8/1990
EP    475 478    *    8/1991    ........... A61K 39/102
(Continued)

OTHER PUBLICATIONS
International Search Report issued Feb. 9, 2010 in PCT/JP09/071398 filed Dec. 24, 2009.
(Continued)

Primary Examiner — Ja'Na Hines
(74) Attorney, Agent, or Firm — Oblon, Spivak, McClelland, Maier & Neustadt, L.L.P.

(57) ABSTRACT

A recombinant avian infectious coryza vaccine and a process for preparing the same are provided. A process for preparing a recombinant avian infectious coryza vaccine which comprises step of constructing *E. coli* that may produce as an inclusion body a fusion peptide consisting of peptides derived from outer-membrane protein of *Avibacterium paragarinarum* serotype A and serotype C, step of culturing said *E. coli* and collecting and purifying inclusion body from culture, and step of preparing a preparation comprising said purified inclusion body, and an avian infectious coryza vaccine comprising as an active ingredient the fusion peptide. A linker sequence may be inserted between the respective peptides comprising the fusion peptide. For the peptide derived from the serotypes A and C, an amino acid sequence region of Region 2 or its vicinity responsible for protection from infection may be used.

23 Claims, 5 Drawing Sheets

(56) References Cited

U.S. PATENT DOCUMENTS

| | | | |
|---|---|---|---|
| 6,036,959 | A | 3/2000 | Gheysen |
| 6,153,406 | A | 11/2000 | Tai et al. |
| 6,919,080 | B2 * | 7/2005 | Tokunaga et al. .......... 424/185.1 |
| 2003/0027987 | A1 | 2/2003 | Tokunaga et al. |
| 2004/0131638 | A1 | 7/2004 | Debrus et al. |
| 2006/0034854 | A1 | 2/2006 | Berthet et al. |
| 2006/0051379 | A1 | 3/2006 | Biemans et al. |
| 2006/0057160 | A1 | 3/2006 | Biemans et al. |
| 2006/0141563 | A1 | 6/2006 | Biemans et al. |
| 2006/0240045 | A1 | 10/2006 | Berthet et al. |

FOREIGN PATENT DOCUMENTS

| | | | |
|---|---|---|---|
| EP | 0 475 478 A1 | 3/1992 | |
| JP | 9 500537 | 1/1997 | |
| JP | 10 500009 | 1/1998 | |
| JP | 2004-057078 | 2/2004 | |
| JP | 2004 531540 | 10/2004 | |
| JP | 2005-218414 | 8/2005 | |
| JP | 2006 516183 | 6/2006 | |
| JP | 2008-156317 | 7/2008 | |
| WO | 98 12331 | 3/1998 | |
| WO | WO 98/12331 | * 3/1998 | ............ C12N 15/31 |

OTHER PUBLICATIONS

English translation of the International Preliminary Report on Patentability issued Jul. 28, 2011, in PCT/JP2009/071398.

L. A. Page, "*Haemophilus* Infections in Chickens. I. Characteristics of 12 *Haemophilus* Isolates Recovered from Diseased Chickens", American Journal of Veterinary Research, vol. 23, Jan. 1962, pp. 85-95.

Akira Sawata, et al., "*Haemophilus* Infections in Chickens 2. Types of *Haemophilus* paragallinarum Isolates from Chickens with Infectious Coryza, in Relation to *Haemophilus* gallinarum Strain No. 221", Japanese Journal of Veterinary Science, vol. 40, 1978, pp. 645-652.

Katsumi Kume, et al., "Immunologic Relationship Between Page's and Sawata's Serotype Strains of *Haemophilus* paragallinarum", American Journal of Veterinary Research, vol. 41, No. 5, May 1980, pp. 757-760.

Akira Sawata, et al., "Biologic and Serologic Relationships Between Page's and Sawata's Serotypes of *Haemophilus* paragallinarum", American Journal of Veterinary Research, vol. 41, No. 11, Nov. 1980, pp. 1901-1904.

M. Matsumoto, et al., "A Broth Bacterin Against Infectious Coryza: Immunogenicity of Various Preparations", Avian Diseases, vol. 15, 1971, pp. 109-117.

Extended European Search Report issued Apr. 29, 2013, in European Patent Application No. 09834924.4.

Taichi Noro, et al., "Identification and characterization of haemagglutinin epitopes of Avibacterium paragallinarum serovar C", Veterinary Microbiology, vol. 131, No. 3-4, XP-002695642, Oct. 2008, pp. 406-413.

* cited by examiner

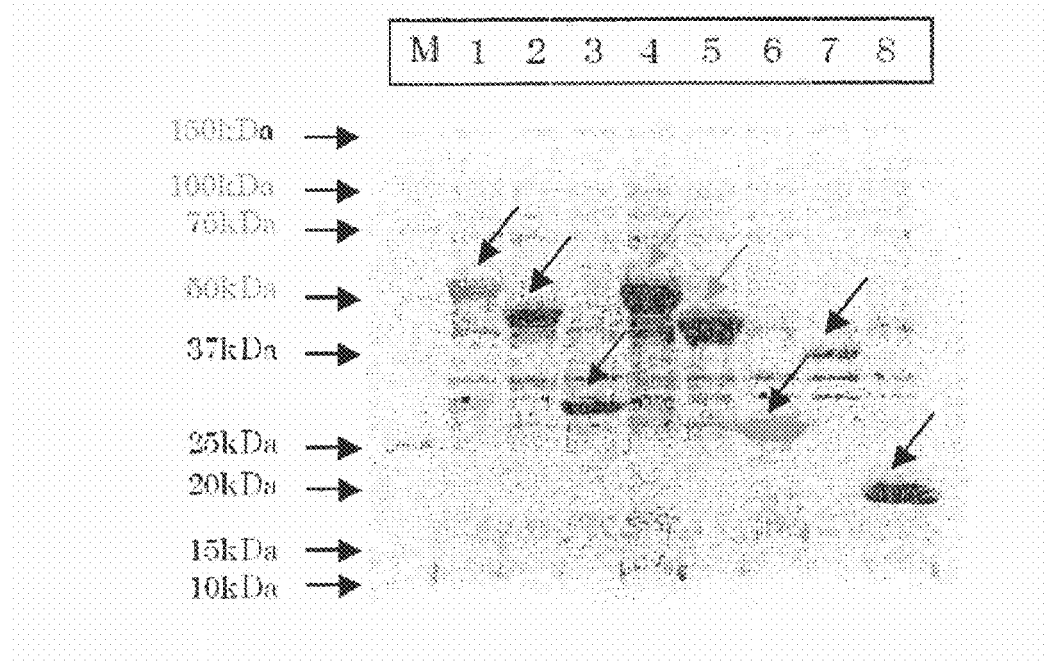

RECOMBINANT AVIAN INFECTIOUS CORYZA VACCINE AND PROCESS FOR PREPARING SAME

CROSS-REFERENCE TO RELATED APPLICATIONS

The present application is a 35 U.S.C. §371 National Stage patent application of International patent application PCT/JP2009/071398, filed on Dec. 24, 2009, which claims priority to Japanese patent application JP 2008-330448, filed on Dec. 25, 2008.

TECHNICAL FIELD

The present invention relates to a recombinant avian infectious coryza vaccine and a process for preparing the same. More particularly, the present invention relates to a recombinant avian infectious coryza vaccine comprising as an active ingredient a fusion peptide consisting of a part of an outer-membrane protein of *Avibacterium paragallinarum* (hereinafter also referred to as "*A.pg*") serotype A and a part of an outer-membrane protein of *A.pg* serotype C and process for preparing the same.

BACKGROUND ART

Avian infectious coryza is one of the most important respiratory diseases caused by infection with *A.pg*. Chicken suffering from avian infectious coryza shows cardinal symptoms of a running nose, swelling of the face and epiphora. Avian infectious coryza brings about a great economical damage since it leads to decrease in the breeding rate of chicken, retarding of egg laying, decrease in egg production or failure of egg laying.

Page et al. classified *A.pg* into three serotypes A, B and C (see e.g. Non-patent reference 1) and Sawata et al. classified *A.pg* into two serotypes 1 and 2 (see e.g. Non-patent reference 2). Thereafter, Kume et al. reported that serotype A by Page et al. corresponds to serotype 1 by Sawata et al. and serotype C by Page et al. corresponds to serotype 2 by Sawata et al. (see e.g. Non-patent references and 4). Today, it is established that main causative agents of avian infectious coryza are *A.pg* serotype A (hereinafter also referred to as "*A.pg*-A") and *A.pg* serotype C (hereinafter also referred to as "*A.pg*-C").

For prevention of avian infectious coryza, an inactivated vaccine has hitherto been used widely which is obtained by inactivating the cells of *A.pg*-A or *A.pg*-C with formalin, thimerosal and the like. However, adverse side effects caused by such an inactivated vaccine have been an issue as it has been reported that local necrotic lesions are formed in the inoculated chicken when the vaccine is administered (see e.g. Non-patent reference 5). Under the circumstances, attempting to develop a safe vaccine, a recombinant vaccine has been investigated comprising a protective antigen against infection prepared by genetic recombination technique.

For instance, Tokunaga et al. isolated and identified a gene coding for an outer-membrane protein of *A.pg*-A (outer-membrane protein gene) and found that a peptide obtained by expressing a part of said gene (HPG3.5 kbp, HPG4.1 kbp) in *E. coli* is useful as a protective antigen against infection for avian infectious coryza. Furthermore, using said DNA fragment as a probe, they obtained an outer-membrane protein gene from *A.pg*-C and compared nucleotide sequences of open reading frame of the outer-membrane protein gene from *A.pg*-A and *A.pg*-C. As a result, they revealed that both nucleotide sequences had homology of about 80% as a whole, that a region of 3.4 kbp at the 5'-end (hereinafter also referred to as "Region 1") and a region of about 1.2 kbp at the 3'-end (hereinafter also referred to as "Region 3") had extremely high homology and that a region of about 1.5 kbp flanked by Region 1 and Region 3 (hereinafter also referred to as "Region 2") had low homology (see Patent reference 1).

It is also reported by Noro et al. that the outer-membrane protein discovered by Tokunaga et al. is important as a protective antigen for avian infectious coryza. Noro et al. immunized chicken with peptides coded by DNA fragments of 4,801 by and 5,157 bp, which are parts of the outer-membrane protein gene from *A.pg*-A, to show that said peptides may induce HI antibody to *A.pg*-A and may have a vaccine effect (see e.g. Patent reference 2) and further reported that peptides coded by DNA fragments of about 5.1 kbp and 5.5 kbp, which are parts of the outer-membrane protein gene from *A.pg*-C, had similar function and effect (see e.g. Patent reference 3).

On the other hand, Yamamoto et al. employed a polypeptide coded by a DNA fragment of 2,016 bp, which comprises most of the outer-membrane protein gene from *A.pg*-A to show usefulness of said polypeptide (see e.g. Patent reference 4) but the nucleotide sequence of about 300 by at the 3' end of the DNA fragment reported by them was extremely different from those shown by Tokunaga et al. and Noro et al.

Patent reference 1: WO98/12331
Patent reference 2: Japanese patent No. 4001117
Patent reference 3: JP 2008-156317
Patent reference 4: JP 2004-57078
Non-patent reference 1: Am. J. Vet. Res., 23:85-95, 1962
Non-patent reference 2: Jpn. J. Vet. Sci., 40:645-652, 1978
Non-patent reference 3: m. J. Vet. Res., 41:757-760, 1980
Non-patent reference 4: Am. J. Vet. Res., 41:1901-1904, 1980
Non-patent reference 5: Avian Dis., 15:109-117, 1971

DISCLOSURE OF THE INVENTION

Technical Problem to be Solved by the Invention

As described above, it has been revealed that the outer-membrane protein or its partial peptide from *A.pg*-A and *A.pg*-C, the main causative agent of avian infectious coryza, is useful as a protective antigen against avian infectious coryza. Thus, by mixing these protective antigens against infection, immunization to avian infectious coryza may efficiently be done. However, an approach by simple mixing necessitates separate production of the two infectious protective antigens and thus is costly. In general, a vaccine for use in an animal, unlike a vaccine for use in human, would not be accepted by a stock farmer unless the vaccine is not only in high quality but also is available at a low cost. Therefore, for a vaccine for use in an animal, a process for the production with less cost for production is desired.

Means for Solving the Problems

The present inventors have assiduously investigated in order to attain the object as described above, and as a result, have revealed that peptide fragments coded by the sequence of about 1.6 kbp comprising Region 2 (the nucleotide sequence of 3,639 by to 5,162 by for *A.pg*-A and the nucleotide sequence of 4,247 by to 5,758 by for *A.pg*-C: see FIGS. 1 and 2) of the outer-membrane protein gene from *A.pg*-A and *A.pg*-C (peptides coded by a DNA sequence of from 3,558 by to 5,192 by for *A.pg*-A and by a DNA sequence of from 4,166 by to 5,788 by for *A.pg*-C: hereinafter also referred to as "AΔ5-1" and CΔ5-1", respectively: see FIGS. 1 and 2) are useful as a protective antigen for avian infectious coryza. The present inventors have found that a fusion peptide (hereinafter also referred to as "ACΔ5-1"), which is obtained by linking together a DNA fragment coding for AΔ5-1 and a DNA fragment coding for CΔ5-1 and expressing the resultant DNA fragment, maintained immunogenicity of the respective antigens even after fusion and that the fusion peptide exhibited infection protective effect to avian infectious coryza equivalent to or more than that of AΔ5-1 or CΔ5-1, each expressed alone. Furthermore, the present inventors have found that CΔ5-1 is expressed in a soluble fraction when expressed alone whereas AΔ5-1 is expressed in an insoluble fraction by forming an inclusion body to thereby complete the present invention.

Accordingly, an object of the present invention is to provide a vaccine for avian infectious coryza comprising as an active ingredient a fusion peptide, obtained by linking to each other a peptide fragment comprising a specific region of the outer-membrane protein from *A.pg*-A and a peptide fragment comprising a specific region of the outer-membrane protein from *A.pg*-C, and a process for preparing the same.

As used herein, the outer-membrane proteins from *A.pg*-A and *A.pg*-C as isolated and identified by Tokunaga et al. (Patent reference 1) are also collectively referred to as "HMTp210 protein" and peptide fragments derived from HMTp210 protein of *A.pg*-A and *A.pg*-C are also referred to as "Peptide A" and "Peptide C", respectively.

Thus, the present invention includes the followings:

[1] A process for preparing a recombinant avian infectious coryza vaccine which comprises step of constructing a host that may produce as an inclusion body a fusion peptide consisting of a peptide fragment (Peptide A) derived from HMTp210 protein of *A.pg*-A and a peptide fragment (Peptide C) derived from HMTp210 protein of *A.pg*-C, step of culturing said host and colleting and purifying a fraction of inclusion body from culture, and step of preparing a preparation comprising said purified fraction of inclusion body.

[2] The process of [1] wherein Peptide A and Peptide C consist of 600 or less amino acid residues.

[3] The process of [1] wherein Peptide A has an amino acid sequence selected from the group consisting of SEQ ID NOs: 1, 27, 28, 29, 30, 31, 32, 33, 34 and 35 whereas Peptide C has an amino acid sequence selected from the group consisting of SEQ ID NOs: 2, 3, 4, 50, 51, 52, 53, 54, 55 and 56.

[4] The process of [3] wherein Peptide A comprises an amino acid sequence shown by SEQ ID NO: 35 whereas Peptide C comprises an amino acid sequence shown by SEQ ID NO: 56.

[5] The process of [3] or [4] wherein Peptide A or Peptide C comprises an amino acid sequence where one or several amino acids are deleted, added or replaced.

[6] The process of any one of [1] to [5] wherein a ratio of Peptide A and Peptide C in the fusion peptide is 1 to 3 of Peptide C to 1 of Peptide A.

[7] The process of any one of [1] to [6] wherein the fusion peptide comprises at least a structure where Peptide C is linked to the C-terminal of Peptide A.

[8] The process of any one of [1] to [7] wherein the fusion peptide has a linker between Peptide A and Peptide A, Peptide C and Peptide C, or Peptide A and Peptide C.

[9] The process of [3] wherein the fusion peptide has an amino acid sequence selected from the group consisting of SEQ ID NOS: 8, 9, 10, 11, 12, 13, 41, 42, 43, 44, 45, 46, 47, 48, 49, 61, 62, 63, 64, 65, 66 and 67.

[10] A recombinant avian infectious coryza vaccine comprising as an active ingredient a fusion peptide consisting of a peptide fragment (Peptide A) derived from HMTp210 protein of *A.pg*-A and a peptide fragment (Peptide C) derived from HMTp210 protein of *A.pg*-C.

[11] The vaccine of [10] wherein the fusion peptide has a property of forming an inclusion body when produced by the host.

[12] The vaccine of [10] wherein Peptide A and Peptide C consist of 600 or less amino acid residues.

[13] The vaccine of [10] wherein Peptide A has an amino acid sequence selected from the group consisting of SEQ ID NOs: 1, 27, 28, 29, 30, 31, 32, 33, 34 and 35 whereas Peptide C has an amino acid sequence selected from the group consisting of SEQ ID NOs: 2, 3, 4, 50, 51, 52, 53, 54, 55 and 56.

[14] The vaccine of [13] wherein Peptide A comprises an amino acid sequence shown by SEQ ID NO: 35 whereas Peptide C comprises an amino acid sequence shown by SEQ ID NO: 56.

[15] The vaccine of [13] or [14] wherein Peptide A or Peptide C comprises an amino acid sequence where one or several amino acids are deleted, added or replaced.

[16] The vaccine of any one of [10] to [15] wherein a ratio of Peptide A and Peptide C in the fusion peptide is 1 to 3 of Peptide C to 1 of Peptide A.

[17] The vaccine of any one of [10] to [16] wherein the fusion peptide comprises at least a structure where Peptide C is linked to the C-terminal of Peptide.

[18] The vaccine of any one of [10] to [17] wherein the fusion peptide has a linker between Peptide A and Peptide A, Peptide C and Peptide C, or Peptide A and Peptide C.

[19] The vaccine of [13] wherein the fusion peptide has an amino acid sequence selected from the group consisting of SEQ ID NOs: 8, 9, 10, 11, 12, 13, 41, 42, 43, 44, 45, 46, 47, 48, 49, 61, 62, 63, 64, 65, 66 and 67.

[20] A recombinant avian infectious coryza vaccine comprising as an active ingredient a peptide consisting of a sequence comprising the amino acid sequence shown by SEQ ID NO: 35, said sequence being within the amino acid sequence shown by SEQ ID NO: 1 with addition of 1 to 200 amino acid residues at the N-terminal and/or C-terminal thereof.

[21] The vaccine of [20] wherein said vaccine comprises as an active ingredient a peptide consisting of the amino acid sequence shown by SEQ ID NO: 1.

[22] A recombinant avian infectious coryza vaccine comprising as an active ingredient a peptide consisting of a sequence comprising the amino acid sequence shown by SEQ ID NO: 56, said sequence being within the amino acid sequence shown by SEQ ID NO: 3 with addition of 1 to 200 amino acid residues at the N-terminal and/or C-terminal thereof.

[23] The vaccine of [22] wherein said vaccine comprises as an active ingredient a peptide consisting of the amino acid sequence shown by SEQ ID NO: 3 or 52.

[24] The vaccine of [21] or [23] wherein said peptide comprises an amino acid sequence where one or several amino acids are deleted, added or replaced.

Effects of the Invention

In accordance with the present invention, provided are an avian infectious coryza vaccine comprising as an active ingredient a fusion peptide consisting of a peptide fragment derived from HMTp210 protein of *A.pg*-A and a peptide fragment derived from HMTp210 protein of *A.pg*-C linked to each other and a process for preparing the same. The avian infectious coryza vaccine of the present invention may simultaneously provide immunization for protection from avian infectious coryza caused by *A.pg*-A and *A.pg*-C.

In accordance with the process of the present invention, it becomes possible to let CΔ5-1, which is expressed in a soluble fraction when expressed alone, form an inclusion body so as to be expressed in an insoluble fraction via expression of its fusion peptide with AΔ5-1. As a result, not only purification of said fusion peptide is facilitated but also production cost is reduced since infection protective antigens to *A.pg*-A and *A.pg*-C may be prepared with a single culture.

BRIEF DESCRIPTION OF DRAWINGS

FIG. 8 is a photograph showing results of SDS-PAGE performed on supernatant and precipitate fractions after centrifugation of cell debris of peptide C-producing *E. coli*. M: marker, Lane 1: CΔ5-1-pQE (supernatant fraction), Lane 2: CΔ5-2-pQE (supernatant fraction), Lane 3: CΔ5-4-pQE (supernatant fraction), Lane 4: CΔ9-O-pQE (supernatant fraction), Lane 5: CΔ9-2-pQE (supernatant fraction), Lane 6: CΔ9-4-pQE (supernatant fraction), Lane 7: CΔ6-2-pQE (precipitate fraction), Lane 8: CΔ6-4-pQE (supernatant fraction). Arrows show fusion peptides as expressed.

BEST MODE FOR CARRYING OUT THE INVENTION

Figure 1:
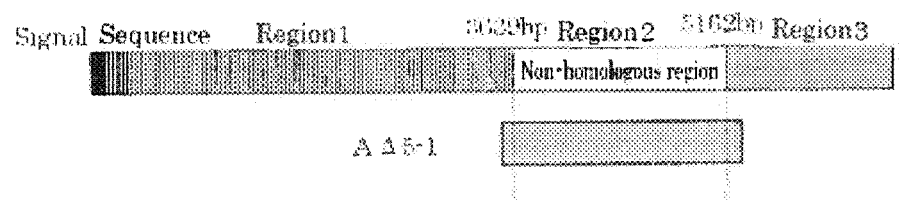
FIG. 1 shows a position of AΔ5-1 fragment in HMTp210 gene of *A.pg*-A (HMTp210A gene) where the indicated nucleotide numbers correspond to those disclosed in Patent reference 1 (Tokunaga et al.).

The present invention is characterized by a process for preparing a recombinant avian infectious coryza vaccine comprising step of preparing an inclusion body-forming fusion peptide consisting of Peptide A derived from HMTp210 protein of *Avibacterium paragarinarum* (hereinafter referred to as "*A.pg*") serotype A and Peptide C derived from HMTp210 protein of *A.pg*-C. More specifically, the present invention is characterized by a process for preparing an avian infectious coryza vaccine which comprises step of constructing a host that may produce as an inclusion body a fusion peptide consisting of a peptide fragment derived from HMTp210 protein of *A.pg*-A and a peptide fragment derived from HMTp210 protein of *A.pg*-C, step of culturing said host and colleting and purifying a fraction of inclusion body from culture, and step of preparing a preparation comprising said purified fraction of inclusion body, and an avian infectious coryza vaccine comprising as an active ingredient said fusion peptide.

A DNA fragment may be obtained as described below that consists of a part of a gene (hereinafter also referred to as "HMTp210A gene") coding for an amino acid sequence of HMTp210 protein (SEQ ID NO: 25) of *A.pg*-A and a gene (hereinafter also referred to as "HMTp210C gene") coding for an amino acid sequence of HMTp210 protein (SEQ ID NO: 26) of *A.pg*-C There are several isolated strains of *A.pg*-A and *A.pg*-C and any of these strains may be used in the present invention without limitation. Hitherto, there have been isolated, for instance, 221, O83 and W strains etc. for *A.pg*-A and 53-47, Modesto and HK-1 strains etc. for *A.pg*-C wherein mutations of substitution, deletion or addition of one or several amino acids are noted. For the present invention, any of these strains or mutants may be used.

For growth of *A.pg*-A and *A.pg*-C, a culture medium may be used that suitably contains polypeptone, glucose, casamino acid, sodium glutamate, yeast extract, sodium chloride, chicken meat infusion, nicotineamide adenine dinucleotide (β-NAD), chicken sera, and the like. A chicken broth supplemented with chicken sera was used herein, containing polypeptone S 5 g, casamino acid 1 g, sodium chloride 5 g, sodium L-glutamate 5 g, glucose 1 g, yeast extract 10 g, chicken meat infusion 175 mL, chicken sera 25 mL, β-NAD 0.025% in 1,000 mL of culture medium, for growth in a small/medium scale. Culture condition may be usually set at the temperature of 37° C. for 16 to 24 hours, which condition may suitably vary depending on purpose of use, a mode of culture, an amount of bacteria inoculated, a scale of culture, and the like.

Cells in culture may be collected by centrifugation (5,800 g, 20 min.) in a precipitate fraction. HMTp210A gene and HMTp210C gene (hereinafter also referred to collectively as "HMTp210 gene" in case that the two genes are not separately referred to) may be prepared from a genomic DNAs extracted from the cells by genetic recombination technique according to Sambrook et al. (Molecular Cloning, A Laboratory Manual Second Edition. Cold Spring Harbor Laboratory Press, N.Y., 1989). A commercially available kit may also be used. For instance, for extraction of chromosomal DNAs, PureGene kit (Gentra Systems), SepaGene kit (Sanko Junyaku Co., Ltd.), ISOPLANT (Wako Pure Chemical Industries, Ltd.), and the like may be used.

More specifically, chromosomal DNAs may be extracted from the cells collected by centrifugation using PureGene kit (Gentra Systems) and the like, and a genome DNA library of the cells may be prepared in accordance with Tokunaga et al. (Patent reference 1). Using the obtained DNA fragments as a template, PCR may be performed to amplify DNA fragments in desired sizes using Prime STAR HS DNA Polymerase (TAKARA BIO Inc.) in accordance with protocol attached thereto. Primers for use in PCR may be designed based on the nucleotide sequences of *A.pg*-A- and *A.pg*-C-derived HMT p210 genes as Tokunaga et al. disclosed (Patent reference 1). Primers for PCR may be readily available if asked to DNA synthesis contractor services (e.g. Sigma Genosys Japan K.K.). When designed, nucleotide sequences of appropriate restriction enzyme cleavage sites may be added at the 5'-end of upstream Primer and at the 5'-end of downstream Primer.

A DNA fragment coding for the fusion peptide of the present invention may be obtained by linking together the DNA fragment coding for HMTp210A gene and the DNA fragment coding for HMTp210C gene, as obtained above, using a DNA synthase directly or after cleavage with a restriction enzyme. A DNA fragment coding for a linker consisting of an amino acid sequence of a suitable size may optionally be added between the DNA fragment coding for HMTp210A gene and the DNA fragment coding for HMTp210C gene. For a linker, an amino acid with a lot of flexibility such as a neutral amino acid, e.g. glycine, serine, and the like may preferably be used. A linker consisting of a single sort of amino acids or two or more sorts of amino acids may be used. A linker may be in general in a size of 5 to 20 amino acids, preferably, in a size of 10 to 15 amino acids.

In accordance with the present invention, a DNA fragment of the HMTp210A gene and the HMTp210C gene coding for a fusion peptide may be used that may protect from infection of *A.pg*-A and *A.pg*-C and form an inclusion body. Such a DNA fragment includes, for instance, a DNA fragment coding for a peptide of Region 2 of an outer-membrane protein, a DNA fragment coding for a peptide of Region 2 with addition of an amino acid sequence at N-terminal and/or C-terminal thereof, DNA fragment coding for a peptide of Region 2 with addition of an amino acid sequence at N-terminal or C-terminal thereof and with deletion of an amino acid sequence at the remaining N-terminal or C-terminal thereof, and a DNA fragment coding for a peptide of Region 2 with deletion of an amino acid sequence at N-terminal and/or C-terminal thereof. The amino acid sequence to be added or deleted may be of 1 to 200, preferably 30 to 150 amino acids in length.

Preferable is a DNA fragment coding for a peptide derived from HMTp210 protein of *A.pg*-A having an amino acid sequence selected from the group consisting of SEQ ID NOs: 1, 27, 28, 29, 30, 31, 32, 33, 34 and 35 and a peptide derived from HMTp210 protein of *A.pg*-C having an amino acid sequence selected from the group consisting of SEQ ID NOs: 2, 3, 4, 5, 6, 7, 50, 51, 52, 53, 54, 55 and 56. A DNA fragment coding for a mutant of the above peptide may also be used wherein one or several amino acids are deleted, added or replaced. A "mutant of the above peptide wherein one or several amino acids are deleted, added or replaced" as used herein refers to a mutant of the above peptide wherein 1, 2, 3, 4 or 5 amino acids are deleted, added or replaced. A DNA fragment coding for such a mutant peptide may be obtained by hybridization with a DNA fragment having a nucleotide sequence complementary to the nucleotide sequence of the DNA fragment coding for the above peptide under stringent condition or a method for introducing mutation such as site directed mutagenesis. These may be done by using kits commercially available.

Any combination of a DNA fragment derived from the HMTp210A gene and a DNA fragment derived from the HMTp210C gene may be used as far as a resulting peptide may form an inclusion body. For instance, a DNA fragment coding for a fusion peptide may be a DNA fragment derived from the HMTp210A gene downstream of which a DNA fragment derived from the HMTp210C gene is bound or vice versa. DNA fragments coding for a fusion peptide may also be combined to each other in tandem. Also, two or more DNA fragments derived from the HMTp210A gene may be bound to each other and downstream thereof two or more DNA fragments derived from the HMTp210C gene may further be bound. A DNA coding for fusion peptide may consists of a DNA fragment derived from the HMTp210A gene and a DNA fragment derived from the HMTp210C gene at a ratio of 1 of the former to 1 to 3 of the latter. Preferably, said ratio is 1:1. A nucleotide sequence of the obtained DNA fragment, after cloning into pBluescript II SK+ (Stratagne) or pCR2.1-TOPO (Invitrogen), may be determined with a DNA sequencer (ABI Prism 377 Applied Biosystems).

The thus obtained DNA fragments of *A.pg*-A and *A.pg*-C or the DNA fragment coding for a fusion peptide may be incorporated into an appropriate expression vector, which may then be introduced into a host for expression of each of the DNA fragments. For expression of a heterologous protein or peptide, bacteria, yeasts, animal cells, plant cells, insect cells, and the like may ordinarily be used, among which any host may be used as far as an inclusion body may be produced. For transformation of a host cell, methods known in the art may be used. For instance, calcium phosphate, DEAE dextran, approach using liposome such as lipofectin, polyethylene glycol fusion of protoplast, electroporation, heat shock, and the like may be used, as appropriately selected depending on a host cell as used. Preferably, *E. coli* may be used which allows for expression in a large amount.

For expression in *E. coli*, various expression vectors having trp promoter, T7 promoter, cspA promoter, and the like have been developed and commercially available and may be used as appropriate. Such an expression vector includes, for instance, pET-11d (Merck) and pQE30 (Quiagen). Depending on an expression vector, suitable *E. coli* such as BL21, HMS174, DH5a, HB101, JM109, and the like may be selected as a host. Transformation of *E. coli* may be conducted using commercially available competent cells in accordance with protocol attached thereto. Thus, recombinant *E. coli* producing the desired polypeptide may be obtained. For culture medium (e.g. LB, SOC, SOB, and the like) used for culture of *E. coli*, reagents used for selection of transformant (e.g. ampicillin) and reagents used for induced expression (e.g. indole acetic acid (IAA), isopropylthio-β-D-galactoside (IPTG), and the like), commercially available ones may be used. A pH of a culture medium may be within a range suitable for growth of *E. coli* (pH 6 to 8).

Screening of recombinant *E. coli* expressing a desired peptide (the object) may be carried out as described below. Cells cultured and grown in the presence of an expression inducer (IPTG was used in an expression system in the present invention) are collected by centrifugation (9,100 g, 5 minutes), suspended in a fixed volume of distilled water or PBS, disrupted by sonication or a homogenizer such as French press or Manton Golin and subject to centrifugation (e.g. 17,800 g, 15 minutes) for separation and recovery in precipitate and supernatant. To distilled water may appropriately be added a surfactant (e.g. Triton X-100), a chelating agent (e.g. EDTA), lisozyme, and the like. A fixed amount of supernatant and precipitate recovered may be subject to SDS-polyacrylamide gel electrophoresis, and after staining with Coomassie Brilliant Blue, expression of the object may be confirmed by a molecular size and stained image. For confirmation (or detection) of the object, approach based on an antigen-antibody reaction such as ELISA, Western blot, dot blot, and the like may also be used other than approach based on a molecular size as described above. All of these approaches are commonly used for detecting a heterologous protein or polypeptide expressed in E. coli and may be selected as appropriate. Thus, clones recovered in the precipitate, i.e. clones producing a fusion peptide that may form an inclusion body, may be selected.

Recovery of an inclusion body from the clones producing a fusion peptide may be carried out as described below. First, cells may be collected using centrifugation or MF membrane of a suitable size (Asahi Kasei Corporation). The collected cells may be disrupted in an appropriate manner so as to release inclusion bodies consisting of a fusion peptide out of the cells. Disruption of cells may be done by any known methods including, for instance, dissolution with a chemical substance, a surfactant, an enzyme, or physical treatment such as French press or sonication. By combining several of these, cells may be disrupted more effectively.

For instance, after the cells collected with MF membrane were diluted and concentrated with deionized water to remove the remaining culture components and the cellular metabolites, an appropriate buffer and lysozyme may be added and the resulting mixture may be left at a low temperature (4 to 15° C.) overnight to thereby dissolve the cellular membrane of the cells. The treated solution of the cells may be subject to French press (or Manton Golin) at 500 to 600 $kg/cm^2$ to disrupt the cells. A buffer may be of any kind as far as it has a buffering ability at a pH range of 7.5 to 9 at which lysozyme is active, such as Tris buffer. The buffer may be used at a concentration as commonly used as a buffer (10 to 50 mM). Lysozyme may be used at a concentration of 0.3 to 1.0 g/L. For instance, 20 mM Tris buffer at pH 8.5 may be added, lysozyme (0.6 g/L) may be added and the mixture may be left to stand at 4° C. overnight to dissolve the cell wall of the cells. After disrupting the cells with French press, dilution and concentration with a buffer or deionized water and MF membrane may be repeated to remove most of cellular components. Optionally, a surfactant such as Triton-X100 may be added. Inclusion bodies may be recovered by centrifugation of a concentrated solution containing inclusion bodies as precipitate.

The recovered inclusion bodies may be dissolved in a solution containing a denaturing agent. A denaturing agent to be used includes urea, guanidine hydrochloride, and the like with urea being preferable. Such urea and guanidine hydrochloride may be used in a range of concentration of 4 to 8 M and 2 to 6 M, respectively. For the present invention, 8M urea may preferably be used. For dissolving a denaturing agent and a reducing agent, a buffer at pH 6 to 9, preferably at pH 7 to 8, may be used. Any buffer that has a buffering ability at the above pH range may be used such as phosphate buffer, Tris buffer, glycine buffer, carbonate buffer, and the like. Dissolution may be performed at a temperature of 40° C. or less. Dissolution time may be set while observing dissolution of inclusion bodies, and usually 30 minutes to 1 hour.

Next, refolding, i.e. reconstruction of a normal steric structure, of a fusion peptide may be carried out by adding 10 to 20-fold volume of a buffer to the solution of inclusion bodies or by dialyzing the solution against a buffer. For refolding, the same kind, temperature and pH of a buffer as those used for dissolution of inclusion bodies may be employed. Refolding may be carried out at room temperature or less and by being left to stand for 1 to 7 days, preferably, for 3 to 4 days.

The solution containing fusion peptide may further be subject to purification procedure as occasion demands. For such purification procedure, a combination of the methods commonly used in the field of protein chemistry may be used such as e.g. centrifugation, salting-out, ultrafiltration, isoelectric focusing, electrophoresis, ion exchange chromatography, gel filtration chromatography, affinity chromatography, hydrophobic chromatography, hydroxyapatite chromatography, and the like. An amount of the obtained protein or polypeptide may be measured with a reagent for protein measurement such as BCA Protein Assay Reagent Kit (Pierce Biotechnology, Inc), Protein Assay Kit (BIO-RAD, Inc), and the like.

Usefulness of the fusion peptide of present invention as an avian infectious coryza vaccine may be demonstrated by immunizing chicken with a solution containing said fusion peptide and determining an antibody titer to *A.pg*-A and *A.pg*-C in sera obtained from the chicken or by challenging said immunized chicken with virulent bacteria and observing survival of the chicken and clinical symptoms such as a running nose, swelling of the face and epiphora. For immunization of chicken, an immune enhancing agent (adjuvant), as used for ordinary pharmaceutical preparation, may optionally be added. A mode of administration is not particularly restricted and administration may be done, for instance, subcutaneously, intradermally, intraperitoneally, or intranasally, oridinarily once to thrice every 2 to 4 weeks.

For preparing a pharmaceutical preparation containing the fusion peptide of the present invention as a vaccine, a solution containing said fusion peptide may be sterile filtered through membrane filter and to the filtrate may be added, as occasion demands, an immune enhancing agent (adjuvant) such as aluminum hydroxide, aluminum phosphate, mineral oil or non-mineral oil, a stabilizing agent such as Polysorbate 80, amino acids, and sugars, e.g. lactose and sucrose, and a preservative agent such as formalin, thimerosal, 2-phenoxyethanol, benzyl alcohol, benzethonium chloride and benzalkonium chloride. Also, by adding sugars effective as an excipient such as lactose or sucrose, a lyophilized preparation may be prepared. Thus, a vaccine comprising as an active ingredient the fusion peptide of the present invention may be prepared.

The obtained vaccine may be used alone as an avian infectious coryza vaccine or alternatively used as a mixed vaccine in combination with at least one vaccine selected from the group consisting of vaccines against other viruses such as avian infectious bronchitis virus, avian infectious bursal disease virus, avian encephalomyelitis virus, and egg drop syndrome virus, vaccinesropagainst bacteria such as *Salmonella typhimurium, Salmonella enteritidis*, and *Salmonella pollorum* and vaccines against protozoa such as *Leucocytozoon caulleryi, Eimeria tenera*, and *Eimeria maxima*.

The present invention is explained in more detail by means of the following Examples but is not construed to be limited thereto.

Example 1

Construction of Plasmids for Expression of Fusion Peptides

Genome DNA libraries of *A.pg*-A 221 strain and *A.pg*-C 53-47 strain were prepared in accordance with Tokunaga et al. (Patent reference 1). Briefly, genomic DNAs were extracted using PureGene kit (Gentra Systems) from cells collected by centrifugation (Tomy, RD-20PIV, 4,400 g, 20 min.). Using the obtained DNAs as a template, PCR was performed with Prime STAR HS DNA Polymerase (TAKARA BIO Inc.) to amplify DNA fragments of HMTp210 protein genes of A.pg-A and A.pg-C. PCR conditions were as follows: after reaction at 98° C. for 1 minute, denaturation (98° C. for seconds), annealing (55° C. for 15 seconds), and elongation reaction (72° C. for 120 seconds) for 15 cycles, followed by termination reaction (72° C. for 7 minutes).

Figure 2:
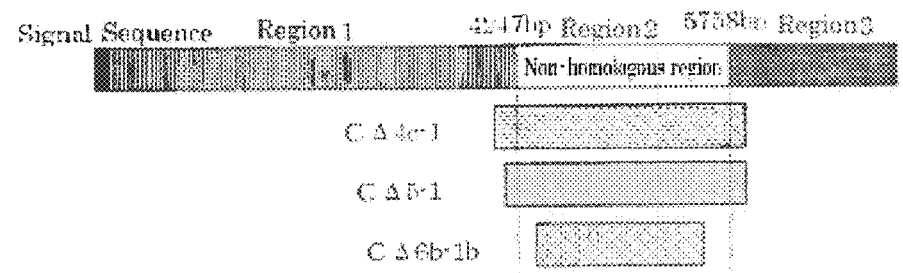
FIG. 2 shows a position of CΔ4c-1, CΔ5-1 and CΔ6b-1b fragments in HMTp210 gene of *A.pg*-C (HMTp210C gene) where the indicated nucleotide numbers correspond to those disclosed in Patent reference 1 (Tokunaga et al.).

Table 1 shows names and Sequence ID NOs of the respective DNA fragments and PCR primers used in the amplification reaction. NcoI recognition sequence was added to the 5'-primer and BamHI recognition sequence was added to the 3'-primer used for amplification of the DNA fragments of A.pg-A and BamHI recognition sequence was added to both the 5'-primer and the 3'-primer used for amplification of the DNA fragments of A.pg-C. FIGS. 1 and 2 show relative position of the respective DNA fragments. In Table, SEQ ID NOs indicated in the column of DNA fragments denote amino acid sequences coded by the respective DNA fragments.

TABLE 1

| DNA fragment | 5'-primer | 3'-primer |
| --- | --- | --- |
| AΔ5-1 (SEQ ID NO: 1) | AΔ5-1-P5 (SEQ ID NO: 14) | AΔ5-1-P3 (SEQ ID NO: 15) |
| CΔ4c-1 (SEQ ID NO: 2) | CΔ4c-1-P5 (SEQ ID NO: 16) | CΔ4-5-P3 (SEQ ID NO: 17) |
| CΔ5-1 (SEQ ID NO: 3) | CΔ5-1-P5 (SEQ ID NO: 18) | CΔ4-5-P3 (SEQ ID NO: 17) |
| CΔ6b-1b (SEQ ID NO: 4) | CΔ6b-1b-P5 (SEQ ID NO: 19) | CΔ6b-1b-P3 (SEQ ID NO: 20) |

Expression plasmids were prepared as described below. First, AΔ5-1 was digested with NcoI and BamHI and, after separation by 0.8% agarose gel electrophoresis, the DNA fragments were eluted and recovered using Wizard SV Gel and PCR Clean-Up System (Promega). The obtained fragments were linked to an expression vector pET-11d (Merck) digested previously with NcoI and BamHI and the resulting plasmid was used to transform E. coli BL21(DE3) strain (Merck). From this transformant, expression plasmid (pET-11d-AΔ5-1) was extracted using Wizard Plus SV Minipreps DNA Purification System (Promega).

Next, CΔ4c-1, CΔ5-1 and CΔ6b-1b were digested with BamHI and, after separation by 0.8% agarose gel electrophoresis, the DNA fragments were eluted and recovered using Wizard SV Gel and PCR Clean-Up System (Promega). The obtained fragments were linked in a forward orientation to pET-11d-AΔ5-1 digested previously with BamHI and the resulting plasmid was used to transform E. coli BL21(DE3) strain (Merck) to give expression plasmids pET-11d-AΔ5-1-CΔ4c-1, pET-11d-AΔ5-1-CΔ5-1 and pET-11d-AΔ5-1-CΔ6b-1b. In each of the constructed expression plasmids, CΔ4c-1, CΔ5-1 and CΔ6b-1b were inserted directly downstream of AΔ5-1 in a forward orientation which produce the fusion peptides as shown in Table 2.

TABLE 2

| Plasmid | Fusion peptide |
| --- | --- |
| pET-11d-AΔ5-1-CΔ4c-1 | AΔ5-1/CΔ4c-1 (SEQ ID NO: 8) |
| pET-11d-AΔ5-1-CΔ5-1 | ACΔ5-1 (SEQ ID NO: 9) |
| pET-11d-AΔ5-1-CΔ6b-1b | AΔ5-1/CΔ6b-1b (SEQ ID NO: 10) |

Example 2

Construction of Plasmids for Expression of Fusion Peptides with Addition of Linker For addition of a linker sequence, DNA fragments of HMTp210 protein gene of A.pg were amplified as described in Example 1. Table 3 shows names and Sequence ID NOs of the respective DNA fragments and PCR primers used in the amplification reaction. The 5'-primer was added with XbaI recognition sequence and the 3'-primer was added with BamHI recognition sequence. In Table, SEQ ID NOs indicated in the column of DNA fragments denote amino acid sequences coded by the respective DNA fragments.

TABLE 3

| DNA fragment | 5'-primer | 3'-primer |
| --- | --- | --- |
| AΔ5-1 (SEQ ID NO: 1) | AΔ5-1-P5 (SEQ ID NO: 14) | AΔ5-1-P3 (SEQ ID NO: 15) |
| L-CΔ4c-1 (SEQ ID NO: 5) | CΔ4c-1-L-P5 (SEQ ID NO: 21) | CΔ4-5-P3 (SEQ ID NO: 17) |
| L-CΔ5-1 (SEQ ID NO: 6) | CΔ5-1-L-P5 (SEQ ID NO: 22) | CΔ4-5-P3 (SEQ ID NO: 17) |
| L-CΔ6b-1b (SEQ ID NO: 7) | CΔ6b-1b-L-P5 (SEQ ID NO: 23) | CΔ6b-1b-P3 (SEQ ID NO: 20) |

Expression plasmids where a linker is linked directly downstream of AΔ5-1 were prepared as described below. First, AΔ5-1 obtained in Example 1 was digested with NcoI and BamHI and, after separation by 0.8% agarose gel electrophoresis, the DNA fragments were eluted and recovered using Wizard SV Gel and PCR Clean-Up System (Promega). Next, to the C-terminal of the obtained fragments was added with a DNA synthetase a linker sequence consisting of a nucleotide sequence (SEQ ID NO: 24) coding for ten glycine residues (Gly Linker: SEQ ID NO: 68) to give a DNA fragment (AΔ5-1-L). As a consequence of addition of the linker sequence, Bam HI recognition sequence at the C-terminal of AΔ5-1 is lost and instead thereof. XbaI recognition sequence is generated.

Next, CΔ4c-1, CΔ5-1 and CΔ6b-1b were digested with XbaI and BamHI and, after separation by 0.8% agarose gel electrophoresis, the DNA fragments were eluted and recovered using Wizard SV Gel and PCR Clean-Up System (Promega). The obtained fragments were ligated with AΔ5-1 and then digested with BamHI. After separation by 0.8% agarose gel electrophoresis, the DNA fragments were eluted and recovered using Wizard SV Gel and PCR Clean-Up System (Promega). Further, the obtained fragments were inserted into an expression vector pET-11d (Merck) previously digested with NcoI and BamHI. The resulting expression plasmid was used to transform E. coli BL21(DE3) strain (Merck) to give expression plasmids pET-11d-AΔ5-1-L-CΔ4c-1, pET-11d-AΔ5-1-L-CΔ5-1 and pET-11d-AΔ5-1-L-CΔ6b-1b. In each of the constructed expression plasmids, CΔ4c-1, CΔ5-1 and CΔ6b-1b were inserted directly downstream of the linker sequence in a forward orientation which produce the fusion peptides via glycine derived from the linker sequence as shown in Table 4.

TABLE 4

| Plasmid | Fusion peptide |
| --- | --- |
| pET-11d-AΔ5-1-L-CΔ4c-1 | AΔ5-1/L-CΔ4c-1 (SEQ ID NO: 11) |
| pET-11d-AΔ5-1-L-CΔ5-1 | ACΔ5-1-L (SEQ ID NO: 12) |
| pET-11d-AΔ5-1-L-CΔ6b-1b | AΔ5-1/L-CΔ6b-1b (SEQ ID NO: 13) |

Example 3

Construction of Plasmids for Expression of Shortened Fusion Peptides (1)

Figure 4:
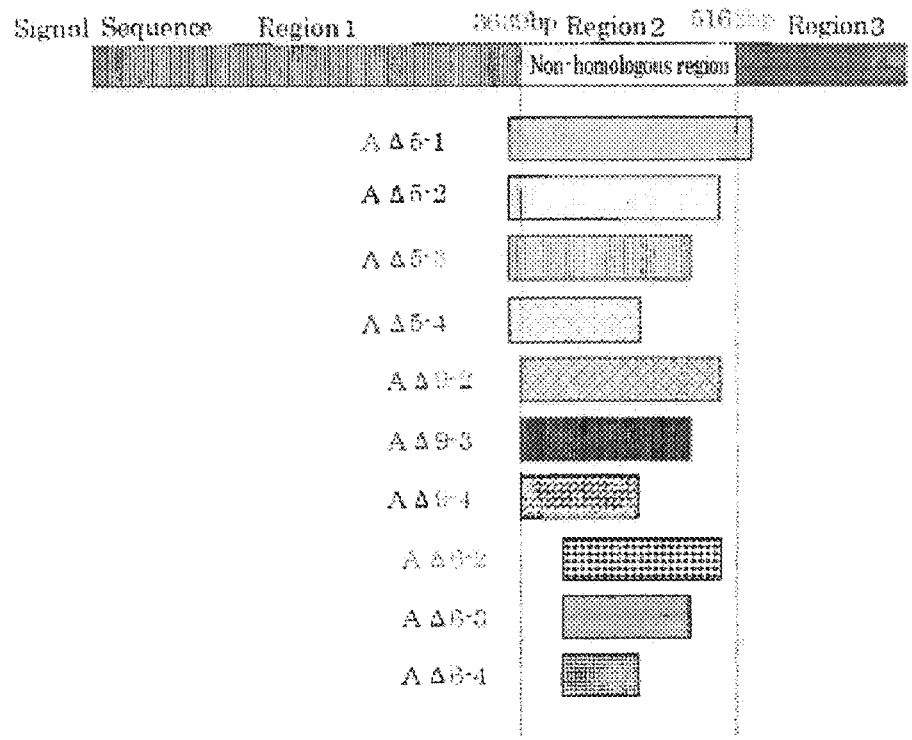
FIG. 4 shows a position of AΔ5-1, AΔ5-2, AΔ5-3, AΔ5-4, AΔ9-2, AΔ9-3, AΔ9-4, AΔ6-2, AΔ6-3 and AΔ6-4 fragments in HMTp210 gene of *A.pg*-A (HMTp210A gene) where the indicated nucleotide numbers correspond to those disclosed in Patent reference 1 (Tokunaga et al.).

Genome DNA libraries of *A.pg*-A 221 strain were prepared as described in Example 1. PCR was performed to amplify the DNA fragments shown in Table 5. PCR conditions were as follows: after reaction at 98° C. for 1 minute, denaturation (98° C. for 10 seconds), annealing and elongation reactions (70° C. for 120 seconds) for 15 cycles, followed by termination reaction (72° C. for 7 minutes). Expression plasmids containing these fragments, pET-11d-AΔ5-1, pET-11d-AΔ5-2, pET-11d-AΔ5-3, pET-11d-AΔ5-4, pET-11d-AΔ9-2, pET-11d-AΔ9-3, pET-11d-AΔ9-4, pET-11d-AΔ6-2, pET-11d-AΔ6-3 and pET-11d-AΔ6-4, were extracted. Table 5 shows names and Sequence ID NOs of the respective DNA fragments and PCR primers used in the amplification reaction. The 5'-primer was added with NcoI recognition sequence and the 3'-primer was added with BamHI recognition sequence. FIG. 4 shows relative position of the respective DNA fragments. In Table, SEQ ID NOs indicated in the column of DNA fragments denote amino acid sequences coded by the respective DNA fragments.

TABLE 5

| DNA fragment | 5'-primer | 3'-primer |
| --- | --- | --- |
| AΔ5-1 (SEQ ID NO: 1) | AΔ5-1-P5 (SEQ ID NO: 14) | AΔ5-1-P3 (SEQ ID NO: 15) |
| AΔ5-2 (SEQ ID NO: 27) | AΔ5-1-P5 (SEQ ID NO: 14) | AΔ2-P3 (SEQ ID NO: 38) |
| AΔ5-3 (SEQ ID NO: 28) | AΔ5-1-P5 (SEQ ID NO: 14) | AΔ3-P3 (SEQ ID NO: 39) |
| AΔ5-4 (SEQ ID NO: 29) | AΔ5-1-P5 (SEQ ID NO: 14) | AΔ4-P3 (SEQ ID NO: 40) |
| AΔ9-2 (SEQ ID NO: 30) | AΔ9-P5 (SEQ ID NO: 36) | AΔ2-P3 (SEQ ID NO: 38) |
| AΔ9-3 (SEQ ID NO: 31) | AΔ9-P5 (SEQ ID NO: 36) | AΔ3-P3 (SEQ ID NO: 39) |
| AΔ9-4 (SEQ ID NO: 32) | AΔ9-P5 (SEQ ID NO: 36) | AΔ4-P3 (SEQ ID NO: 40) |
| AΔ6-2 (SEQ ID NO: 33) | AΔ6-P5 (SEQ ID NO: 37) | AΔ2-P3 (SEQ ID NO: 38) |
| AΔ6-3 (SEQ ID NO: 34) | AΔ6-P5 (SEQ ID NO: 37) | AΔ3-P3 (SEQ ID NO: 39) |
| AΔ6-4 (SEQ ID NO: 35) | AΔ6-P5 (SEQ ID NO: 37) | AΔ4-P3 (SEQ ID NO: 40) |

Next, CΔ5-1 obtained in Example 1 was digested with BamHI and, after separation by 0.8% agarose gel electrophoresis, the DNA fragments were eluted and recovered using Wizard SV Gel and PCR Clean-Up System (Promega). Further, the obtained fragments were linked in a forward orientation to pET-11d-AΔ5-1, pET-11d-AΔ5-2, pET-11d-AΔ5-3, pET-11d-AΔ5-4, pET-11d-AΔ9-2, pET-11d-AΔ9-3, pET-11d-AΔ9-4, pET-11d-AΔ6-2, pET-11d-AΔ6-3 and pET-11d-AΔ6-4 previously digested with BamHI. The resulting expression plasmids were used to transform *E. coli* BL21 (DE3) strain (Merck) to give expression plasmids pET-11d-AΔ5-1-CΔ5-1, pET-11d-AΔ5-2-CΔ5-1, pET-11d-AΔ5-3-CΔ5-1, pET-11d-AΔ5-4-CΔ5-1, pET-11d-AΔ9-2-CΔ5-1, pET-11d-AΔ9-3-CΔ5-1, pET-11d-AΔ9-4-CΔ5-1, pET-11d-AΔ6-2-CΔ5-1, pET-11d-AΔ6-3-CΔ5-1 and pET-11d-AΔ6-4-CΔ5-1. In each of the constructed expression plasmids, CΔ5-1 was inserted directly downstream of the Peptide A expression gene in a forward orientation which produce the fusion peptides as shown in Table 6.

TABLE 6

| Plasmid | Fusion peptide |
| --- | --- |
| pET-11d-AΔ5-1-CΔ5-1 | ACΔ5-1 (SEQ ID NO: 9) |
| pET-11d-AΔ5-2-CΔ5-1 | AΔ5-2/CΔ5-1 (SEQ ID NO: 41) |
| pET-11d-AΔ5-3-CΔ5-1 | AΔ5-3/CΔ5-1 (SEQ ID NO: 42) |
| pET-11d-AΔ5-4-CΔ5-1 | AΔ5-4/CΔ5-1 (SEQ ID NO: 43) |
| pET-11d-AΔ9-2-CΔ5-1 | AΔ9-2/CΔ5-1 (SEQ ID NO: 44) |
| pET-11d-AΔ9-3-CΔ5-1 | AΔ9-3/CΔ5-1 (SEQ ID NO: 45) |
| pET-11d-AΔ9-4-CΔ5-1 | AΔ9-4/CΔ5-1 (SEQ ID NO: 46) |
| pET-11d-AΔ6-2-CΔ5-1 | AΔ6-2/CΔ5-1 (SEQ ID NO: 47) |
| pET-11d-AΔ6-3-CΔ5-1 | AΔ6-3/CΔ5-1 (SEQ ID NO: 48) |
| pET-11d-AΔ6-4-CΔ5-1 | AΔ6-4/CΔ5-1 (SEQ ID NO: 49) |

Example 4

Construction of Plasmids for Expression of Shortened Fusion Peptides (2)

Figure 5:
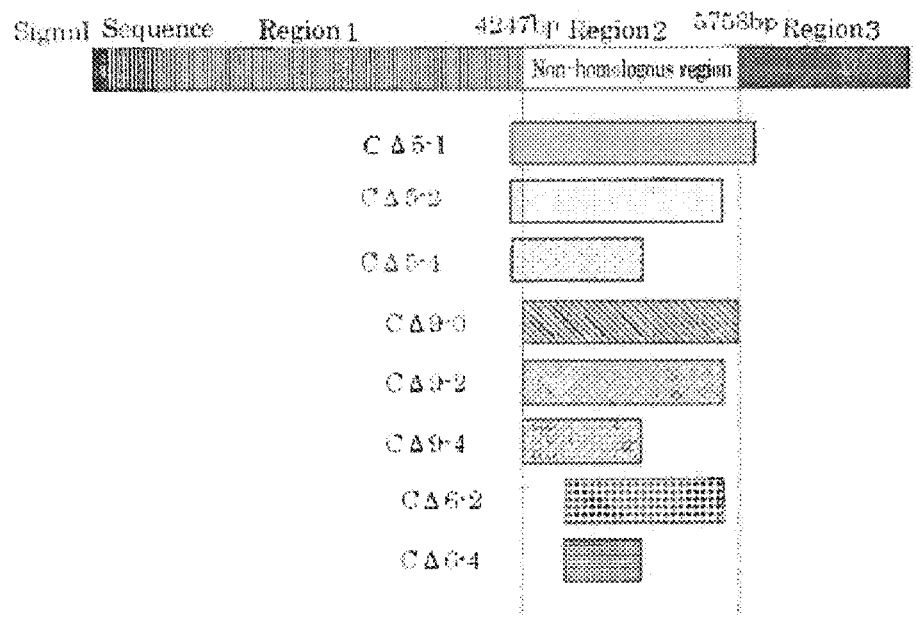
FIG. 5 shows a position of CΔ5-1, CΔ5-2, CΔ5-4, CΔ9-0, CΔ9-2, CΔ9-4, CΔ6-2 and CΔ6-4 fragments in HMTp210 gene of *A.pg*-C (HMTp210C gene) where the indicated nucleotide numbers correspond to those disclosed in Patent reference 1 (Tokunaga et al.).

Genome DNA libraries of *A.pg*-C 53-47 strain were prepared as described in Example 1 to give the DNA fragments shown in Table 7. PCR conditions were as described in Example 3. Table 7 shows names and Sequence ID NOs of the respective DNA fragments and PCR primers used in the amplification reaction. Both the 5'-primer and the 3'-primer were added with BamHI recognition sequence. FIG. 5 shows relative position of the respective DNA fragments. In Table, SEQ ID NOs indicated in the column of DNA fragments denote amino acid sequences coded by the respective DNA fragments.

TABLE 7

| DNA fragment | 5'-primer | 3'-primer |
| --- | --- | --- |
| CΔ5-1 (SEQ ID NO: 3) | CΔ5-1-P5 (SEQ ID NO: 18) | CΔ4-5-P3 (SEQ ID NO: 17) |
| CΔ5-2 (SEQ ID NO: 50) | CΔ5-1-P5 (SEQ ID NO: 18) | CΔ2-P3 (SEQ ID NO: 58) |
| CΔ5-4 (SEQ ID NO: 51) | CΔ5-1-P5 (SEQ ID NO: 18) | CΔ4-P3 (SEQ ID NO: 59) |
| CΔ9-0 (SEQ ID NO: 52) | CΔ9-P5 (SEQ ID NO: 57) | CΔ0-P3 (SEQ ID NO: 60) |
| CΔ9-2 (SEQ ID NO: 53) | CΔ9-P5 (SEQ ID NO: 57) | CΔ2-P3 (SEQ ID NO: 58) |
| CΔ9-4 (SEQ ID NO: 54) | CΔ9-P5 (SEQ ID NO: 57) | CΔ4-P3 (SEQ ID NO: 59) |
| CΔ6-2 (SEQ ID NO: 55) | CΔ6b-1b-P5 (SEQ ID NO: 19) | CΔ2-P3 (SEQ ID NO: 58) |
| CΔ6-4 (SEQ ID NO: 56) | CΔ6b-1b-P5 (SEQ ID NO: 19) | CΔ4-P3 (SEQ ID NO: 59) |

Next, as described in Example 1, CΔ5-1, CΔ5-2, CΔ5-4, CΔ9-0, CΔ9-2, CΔ9-4, CΔ6-2 and CΔ6-4 were digested with BamHI and, after separation by 0.8% agarose gel electrophoresis, the DNA fragments were eluted and recovered using Wizard SV Gel and PCR Clean-Up System (Promega). The obtained fragments were linked in a forward orientation to pET-11d-AΔ5-1 previously digested with BamHI to give expression plasmids pET-11d-AΔ5-1-CΔ5-1, pET-11d-AΔ5-1-CΔ5-2, pET-11d-AΔ5-1-CΔ5-4, pET-11d-AΔ5-1-CΔ9-0, pET-11d-AΔ5-1-CΔ9-2, pET-11d-AΔ5-1-CΔ9-4, pET-11d-AΔ5-1-CΔ6-2 and pET-11d-AΔ5-1-CΔ6-4. In each of the constructed expression plasmids, CΔ5-1, CΔ5-2, CΔ5-4, CΔ9-0, CΔ9-2, CΔ9-4, CΔ6-2 and CΔ6-4 were inserted directly downstream of AΔ5-1 in a forward orientation which produce the fusion peptides as shown in Table 8.

TABLE 8

| Plasmid | Fusion peptide |
|---|---|
| pET-11d-AΔ5-1-CΔ5-1 | ACΔ5-1 (SEQ ID NO: 12) |
| pET-11d-AΔ5-1-CΔ5-2 | AΔ5-1/CΔ5-2 (SEQ ID NO: 61) |
| pET-11d-AΔ5-1-CΔ5-4 | AΔ5-1/CΔ5-4 (SEQ ID NO: 62) |
| pET-11d-AΔ5-1-CΔ9-0 | AΔ5-1/CΔ9-0 (SEQ ID NO: 63) |
| pET-11d-AΔ5-1-CΔ9-2 | AΔ5-1/CΔ9-2 (SEQ ID NO: 64) |
| pET-11d-AΔ5-1-CΔ9-4 | AΔ5-1/CΔ9-4 (SEQ ID NO: 65) |
| pET-11d-AΔ5-1-CΔ6-2 | AΔ5-1/CΔ6-2 (SEQ ID NO: 66) |
| pET-11d-AΔ5-1-CΔ6-4 | AΔ5-1/CΔ6-4 (SEQ ID NO: 67) |

Example 5

Construction of Plasmids for Expression of Peptide C

Genome DNA libraries of *A.pg*-C 53-47 strain were prepared as described in Example 1 to give DNA fragments similar to those shown in Table 7. PCR conditions were as described in Example 3. Names and Sequence ID NOs of the respective DNA fragments and PCR primers used in the amplification reaction were the same as in Table 7 with exception that a restriction enzyme recognition sequence in the 3'-primer was changed from BamHI recognition sequence to HindIII recognition sequence so that the amplified fragments may be inserted into expression vector pQE30 (QIAGEN) more efficiently.

Next, CΔ5-1, CΔ5-2, CΔ5-4, CΔ9-O, CΔ9-2, CΔ9-4, CΔ6-2 and CΔ6-4 were digested with BamHI and HindIII and, after separation by 0.8% agarose gel electrophoresis, the DNA fragments were eluted and recovered using Wizard SV Gel and PCR Clean-Up System (Promega). The obtained fragments were linked to expression vector pQE30 digested with BamHI and HindIII. The resulting expression plasmids were used to transform *E. coli* JM109 strain (QIAGEN) to give plasmids expressing CΔ5-1, CΔ5-2, CΔ5-4, CΔ9-O, CΔ9-2, CΔ9-4, CΔ6-2 and CΔ6-4. The amino acid sequences of peptides obtained from these expression plasmids are those coded by the respective DNA fragments shown in Table 7 with addition at their N-terminal of histidine tag sequence (MRGSHHHHHHGS (SEQ ID NO: 69)) derived from the vectors.

Example 6

Expression of Fusion Peptide (1)

Figure 3:
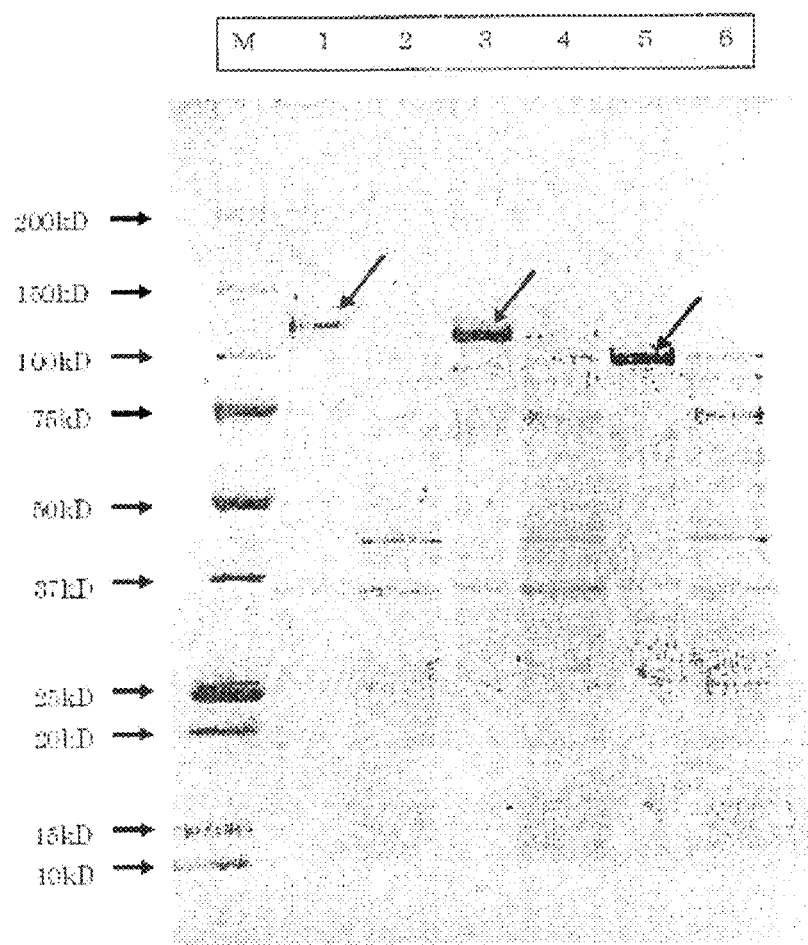
FIG. 3 is a photograph showing results of SDS-PAGE performed on supernatant and precipitate fractions after centrifugation of cell debris of fusion peptide-producing *E. coli*. M: marker, Lane 1: AΔ5-1/CΔ4c-1 (precipitate fraction), Lane 2: AΔ5-1/CΔ4c-1 (supernatant fraction), Lane 3: ACΔ5-1 (precipitate fraction), Lane 4: ACΔ5-1 (supernatant fraction), Lane 5: AΔ5-1/CΔ6b-1b (precipitate fraction), Lane 6: AΔ5-1/CΔ6b-1b (supernatant fraction). Arrows show fusion peptides as expressed.

*E. coli* BL21 (DE3) strain (Merck) possessing the respective expression plasmids obtained in Examples 1 and 2 were inoculated to 1 to 5 mL of LB medium containing 50 μg/mL ampicillin and shake cultured while shaking at 30 to 37° C. until $OD_{600}$ of the culture fluid reached 0.5. IPTG was then added at a final concentration of 1 mM and culture was continued for 3 hours. After centrifugation (Tomy, MX-300, 9,100 g, 5 minutes), supernatant was discarded, a washing buffer (PBS) was added at an amount equivalent to the amount of the initial culture fluid and the cells were suspended to uniformity. The suspension was subject to sonication under ice cooling using handy sonicater (Tomy, UR-20P) at power 10 for 10 seconds for ten times and centrifuged at 17,800 g for 15 minutes. The supernatant was isolated and to the precipitate was added, a washing buffer at an amount equivalent to the amount of the sonicated solution before centrifugation and the precipitate was suspended to uniformity. To each of the isolated supernatant and the precipitate was added an equivalent amount of a sample buffer (2×SDS) and, after heating in boiled water for 5 minutes, SDS-PAGE and staining with Coomassie Brilliant Blue were performed in the conventional manner. When the fusion peptides were observed in the precipitate suspension, it was judged that said fusion peptides formed an inclusion body. FIG. 3 shows the respective expression patterns.

When expressed alone, CΔ4c-1 was expressed in a soluble fraction and fraction of CΔ5-1 expression was not constant whereas all the fusion peptides were stably expressed as an inclusion body. Regarding an expression level, it was somewhat low for AΔ5-1/CΔ4c-1 and was almost equal to each other for the remaining two fusion peptides ACΔ5-1 and AΔ5-1/CL6b-1b with good expression. The fusion peptides with addition of linker showed an expression level equivalent to that of the fusion peptides without addition of linker.

Example 7

Immunogenicity of Fusion Peptide (1)

To confirm the vaccine efficacy of the fusion peptides, a challenge test was carried out using homologous virulent strain. The inclusion bodies in the precipitate suspension of ACΔ5-1 and ACΔ5-1-L obtained in Example 6 were solubilized with 8M urea and the buffer was replaced with PBS (pH 7.4) using a dialysis membrane. A vaccine prepared by emulsifying ACΔ5-1 at the amount of antigen shown in Table 9 in 0.5 mL per dose with oil adjuvant was once administered intramuscularly to the leg of SPF chickens of 8 weeks old for immunization. As a control, group administered with commercially available oil-adjuvanted vaccine with inactivated cells (OILVAX $NB_2AC$, Juridical Foundation The Chemo-Sero-Therapeutic Research Institute) and group with no administration were set. Four weeks after immunization, 0.2 mL of a solution containing *A.pg*-A 221 strain ($1.0 \times 10^{10}$ CFU/mL) or *A.pg*-C 53-47 strain ($3.0 \times 10^9$ CFU/mL) was administered intranasally and clinical symptoms of a running nose, swelling of the face and epiphora were observed for a week.

As a result, as shown in Table 9, chicken administered with the fusion peptides exhibited excellent protective efficacy against challenge from *A.pg*-A 221 strain and *A.pg*-C 53-47 strain and even at 0.06 μg/dose, the vaccine efficacy was more than that of 1/1,000 amount of the commercially available oil adjuvant vaccine. The peptides with addition of linker also exhibited the same protective efficacy. Thus, the fusion peptides proved to be useful as a vaccine.

TABLE 9

| Vaccine | Amount of antigen | Protective rate to challenging strain | |
|---|---|---|---|
| | | A.pg-A 221 | A.gp-C 53-47 |
| ACΔ5-1 | 6 μg/dose | 100% | 100% |
| | 0.6 μg/dose | 100% | 100% |
| | 0.06 μg/dose | 100% | 100% |
| ACΔ5-1-L (with linker addition) | 6 μg/dose | 100% | 100% |
| | 0.6 μg/dose | 100% | 100% |
| | 0.06 μg/dose | 100% | 100% |
| OILVAX $NB_2AC$ | 1/10-fold | 100% | 100% |
| | 1/100-fold | 100% | 100% |
| | 1/1,000-fold | 40% | 20% |
| No immunized control | — | 0% | 0% |

Example 8

Efficacy of Fusion Peptide to Heterologous Strain

To confirm the vaccine efficacy of the fusion peptides to the other strains (heterologous strains) than *A.pg*-A 221 strain and *A.pg*-C 53-47 strain used for preparing the fusion peptide, the challenge test was carried out as in Example 7. The procedures of Example 7 were repeated except that a different amount of antigen for immunization and different virulent strains, i.e. *A.pg*-A 083 strain ($1.0 \times 10^9$ CFU/mL), *A.pg*-A W strain ($4.1 \times 10^9$ CFU/mL) and *A.pg*-C Modesto strain ($2.8 \times 10^9$ CFU/mL), for challenge were used.

As a result, as shown in Table 10, chicken administered with the fusion peptides exhibited excellent protective efficacy against challenge from all the strains of *A.pg*-A 083, *A.pg*-A W and *A.pg*-C Modesto. Thus, the fusion peptides proved to be useful as a vaccine to other virulent strains from which the fusion peptides were not derived.

TABLE 10

| Vaccine | Challenging strain | Amount of antigen | Protection rate |
|---|---|---|---|
| Peptide A (AΔ5-1) | A.pg-A 083 | 3 µg/dose | 100% |
| | | 0.3 µg/dose | 100% |
| | | 0.03 µg/dose | 40% |
| | A.pg-A W | 3 µg/dose | 100% |
| | | 0.3 µg/dose | 100% |
| | | 0.03 µg/dose | 40% |
| Fusion peptide (ACΔ5-1) | A.pg-C Modesto | 6 µg/dose | 100% |
| | | 0.6 µg/dose | 100% |
| | | 0.06 µg/dose | 100% |
| OILVAX NB$_2$AC | A.pg-A 083 | 1/10-fold | 100% |
| | | 1/100-fold | 100% |
| | | 1/1,000-fold | 20% |
| | A.pg-A W | 1/10-fold | 100% |
| | | 1/100-fold | 80% |
| | | 1/1,000-fold | 0% |
| | A.pg-C Modesto | 1/10-fold | 100% |
| | | 1/100-fold | 80% |
| | | 1/1,000-fold | 20% |
| No immunized control | A.pg-A 083 | — | 0% |
| | A.pg-A W | — | 0% |
| | A.pg-C Modesto | — | 0% |

The respective strains used in the challenge test were analyzed for their nucleotide sequence of region 2. As a result, for *A.pg*-A, complete identity between 083 strain and W strain and 1 nucleotide mutation (A/G: glutamic acid at No. 1227 of SEQ ID NO: 25 is replaced with glycine) between 221 strain and 083 strain and between 221 strain and W strain were observed. For *A.pg*-C, deletion of 3 nucleotides AAG (glutamic acid at No. 1144 of SEQ ID NO: 26) was observed in Modesto strain as compared to 53-47 strain.

Example 9

Comparison of Efficacy Between Fusion Peptide ACΔ5-1 and Respective Peptides To compare the vaccine efficacy between the fusion peptide AC45-1 and Peptide A or Peptide C before fusion, an immunization test was carried out. The vaccines were prepared as described in Example 7. A vaccine prepared by emulsifying ACΔ5-1, Peptide A or Peptide C at the amount of antigen shown in Table 11 in 0.5 mL per dose with oil adjuvant was once administered intramuscularly to the leg of SPF chickens of 4 weeks old for immunization. As a control, group with no administration was set. Four weeks after immunization, an antibody titer was determined as described by Ushijima et al. (Japanese patent application No. 2008-29589). Specifically, antibody measurement was carried out by ELISA.

The different peptides within Region 2 of *A.pg*-A and *A.pg*-C were diluted with 50 mM bicarbonate buffer to 1 µg/mL and each 50 µL of the solution was added to 96-well plate for immobilization. After adsorption at 4° C. overnight, the solution was discarded, and the plate was washed with 300 µL of PBS-T (8.1 mM disodium hydrogenphosphate, 1.5 mM potassium dihydrogenphosphate, 137 mM sodium chloride, 2.7 mM potassium chloride, 0.1% Tween 20) and added with 300 µL of PBS-T supplemented with 5% skim milk for blocking. The blocking solution was discarded. Serum was diluted with PBS-T supplemented with 10% skim milk to 100-fold and each 50 µL of the solution was added for reaction at room temperature for 1 hour. After removing the reaction solution, the plate was washed with PBS-T three times. An anti-chicken IgG-HRP-labeled antibody was diluted with PBS-T supplemented with 5% skim milk to 20,000-fold and each 50 µL of the solution was added to each well for reaction at room temperature for 30 minutes in the dark. After removing the reaction solution, the plate was washed with PBS-T three times. Each 100 µL of a substrate solution (TMB substrate-chromogen: DAKO) was added for reaction at room temperature for 15 minutes. Each 100 µL of 3M sulfuric acid was added to stop the reaction. Absorbance at the wavelength of 450 nm was measured with 96-well plate reader (Molecular Devices Japan).

As a result, as shown in Table 11, the chicken immunized with the fusion peptide ACΔ5-1 exhibited a high antibody titer at 0.6 µg/dose and 100% of a positive conversion rate for both *A.pg*-A and *A.pg*-C. At 0.06 µg/dose of the fusion peptide, 80% and 40% of a positive conversion rate were observed for both *A.pg*-A and *A.pg*-C, respectively. However, at 0.03 pg/dose of Peptide A or Peptide C, a positive conversion rate was 60% and 0% for *A.pg*-A and *A.pg*-C, respectively. Thus, it proved that the fusion peptide ACΔ5-1 had higher efficacy than Peptide A or Peptide C before fusion.

TABLE 11

| Vaccine | Amount of antigen | Mean antibody titer (positive conversion rate) | |
|---|---|---|---|
| | | A.pg-A | A.pg-C |
| Fusion peptide (ACΔ5-1) | 6 µg/dose | 2.152 (100%) | 1.649 (100%) |
| | 0.6 µg/dose | 1.924 (100%) | 1.177 (100%) |
| | 0.06 µg/dose | 1.175 (80%) | 0.565 (40%) |
| | 0.006 µg/dose | 0.514 (60%) | 0.112 (0%) |
| Peptide A (AΔ5-1) | 3 µg/dose | 2.051 (100%) | 0.163 (0%) |
| | 0.3 µg/dose | 2.197 (100%) | 0.146 (0%) |
| | 0.03 µg/dose | 1.209 (60%) | 0.086 (0%) |
| | 0.003 µg/dose | 0.080 (0%) | 0.127 (0%) |
| Peptide C (CΔ5-1) | 3 µg/dose | 0.153 (0%) | 1.749 (100%) |
| | 0.3 µg/dose | 0.176 (0%) | 1.865 (100%) |
| | 0.03 µg/dose | 0.072 (0%) | 0.089 (0%) |
| | 0.003 µg/dose | 0.072 (0%) | 0.084 (0%) |
| No immunized control | — | 0.092 (0%) | 0.099 (0%) |

Example 10

Expression of Fusion Peptide (2)

Figure 6:
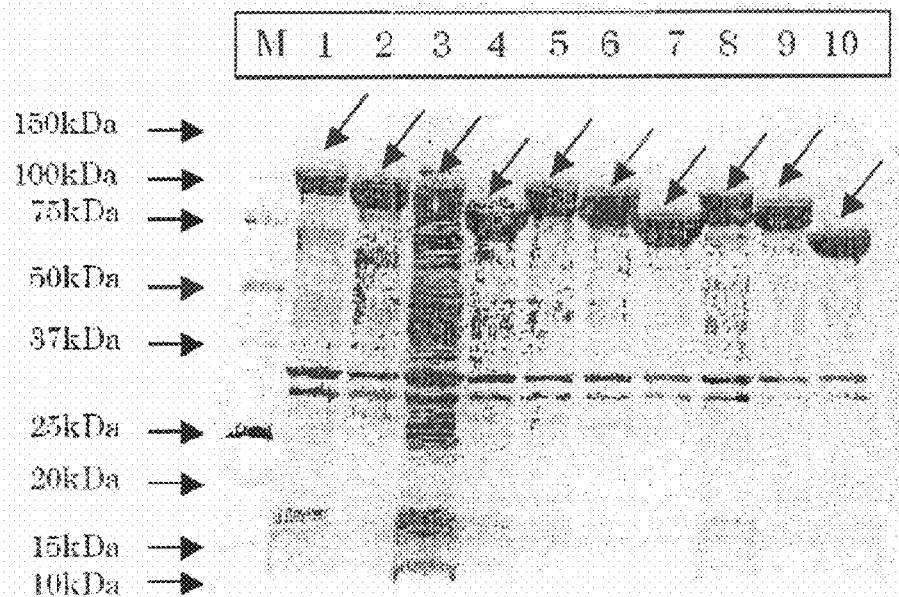
FIG. 6 is a photograph showing results of SDS-PAGE performed on precipitate fractions after centrifugation of cell debris of fusion peptide-producing *E. coli*. M: marker, Lane 1: ACΔ5-1 (precipitate fraction), Lane 2: AΔ5-2/CΔ5-1 (precipitate fraction), Lane 3: AΔ5-3/CΔ5-1 (precipitate fraction), Lane 4: AΔ5-4/CΔ5-1 (precipitate fraction), Lane 5: AΔ9-2/CΔ5-1 (precipitate fraction), Lane 6: AΔ9-3/CΔ5-1 (precipitate fraction), Lane 7: AΔ9-4/CΔ5-1 (precipitate fraction), Lane 8: AΔ6-2/CΔ5-1 (precipitate fraction), Lane 9: AΔ6-3/CΔ5-1 (precipitate fraction), Lane 10: AΔ6-4/CΔ5-1 (precipitate fraction), Arrows show fusion peptides as expressed.
Figure 7:
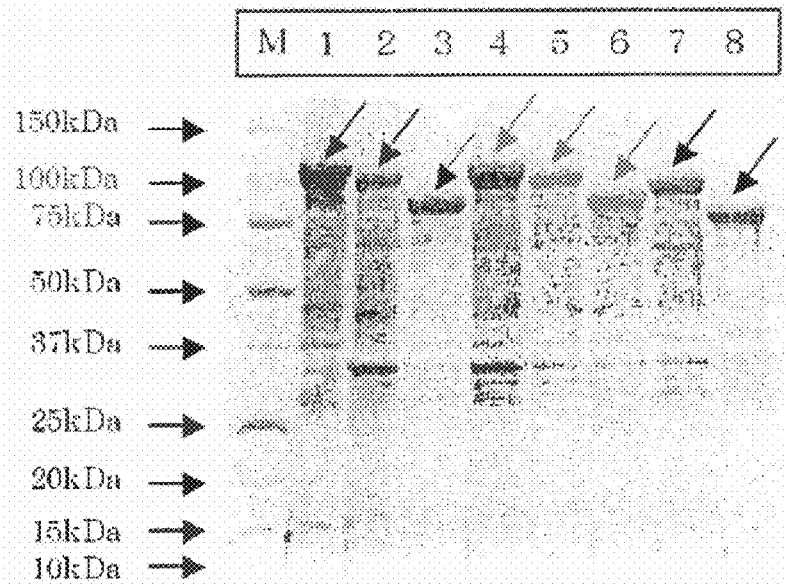
FIG. 7 is a photograph showing results of SDS-PAGE performed on precipitate fractions after centrifugation of cell debris of fusion peptide-producing *E. coli*. M: marker, Lane 1: ACΔ5-1 (precipitate fraction), Lane 2: AΔ5-1/CΔ5-2 (precipitate fraction), Lane 3: AΔ5-1/CΔ5-4 (precipitate fraction), Lane 4: AΔ5-1/CΔ9-0 (precipitate fraction), Lane 5: AΔ5-1/CΔ9-2 (precipitate fraction), Lane 6: AΔ5-1/CΔ9-4 (precipitate fraction), Lane 7: AΔ5-1/CΔ6-2 (precipitate fraction), Lane 8: AΔ5-1/CΔ6-4 (precipitate fraction), Arrows show fusion peptides as expressed.

*E. coli* BL21 (DE3) strain (Merck) possessing the respective expression plasmids obtained in Examples 3 and 4 were subject to expression as described in Example 6 and an expression level was determined. FIGS. 6 and 7 show the respective expression patterns. For Peptide A, AΔ5-4, AΔ9-2, AΔ9-4, AΔ6-2 and AΔ6-4, when expressed alone, were expressed in a soluble fraction but, upon fusion with CΔ5-1, the resulting fusion peptides stably formed an inclusion body except for AΔ6-4. AΔ6-4/CΔ5-1, though principally formed an inclusion body, may sometimes be expressed in a soluble fraction and hence its expression was instable. All the fusion peptides had the same and excellent expression level. On the other hand, Peptide C, when expressed alone, was expressed in a soluble fraction except for CΔ6-2 but, upon fusion with AΔ5-1, the resulting fusion peptides stably formed an inclusion body. All the fusion peptides had the same and excellent expression level.

Example 11

Immunogenicity of Fusion Peptide (2)

To confirm the vaccine efficacy of the fusion peptides obtained in Example 10, a challenge test was carried out using homologous virulent strain (A.pg-A 221 strain) as described in Example 7. The procedures of Example 7 were repeated except that a different amount of antigen for immunization and different number of cells of virulent strain, i.e. A.pg-A 221 strain, $1.2 \times 10^9$ CFU/mL, for challenge were used. As a result, as shown in Table 12, chicken immunized with the respective fusion peptides exhibited excellent protective effects against challenge from A.pg-A 221 strain where 80% protection for AΔ6-4/CΔ5-1 and $100\%$6 protection for the longer fusion peptides were confirmed.

TABLE 12

| Vaccine | Amount of antigen | Protection rate |
| --- | --- | --- |
| ACΔ5-1 | 6 μg/dose | 100% |
| AΔ5-2/CΔ5-1 | 6 μg/dose | 100% |
| AΔ5-3/CΔ5-1 | 6 μg/dose | 100% |
| AΔ5-4/CΔ5-1 | 6 μg/dose | 100% |
| AΔ9-2/CΔ5-1 | 6 μg/dose | 100% |
| AΔ9-3/CΔ5-1 | 6 μg/dose | 100% |
| AΔ9-4/CΔ5-1 | 6 μg/dose | 100% |
| AΔ6-2/CΔ5-1 | 6 μg/dose | 100% |
| AΔ6-3/CΔ5-1 | 6 μg/dose | 100% |
| AΔ6-4/CΔ5-1 | 6 μg/dose | 80% |
| No immunized control | — | 0% |

Example 12

Expression of Peptide C

E. coli JM109 (QIAGEN) possessing the respective expression plasmids obtained in Example 5 were subject to expression as described in Example 6 and an expression level for the respective cells was determined by SDS-PAGE (FIG. 8). The thus obtained peptides were named as CΔ5-1-pQE, CΔ5-2-pQE, CΔ5-4-pQE, CΔ9-0-pQE, CΔ9-2-pQE, CΔ9-4-pQE, CΔ6-2-pQ and CΔ6-4-pQE. All the peptides except for CΔ6-2-pQE were expressed in a soluble fraction with an excellent expression level.

Example 13

Confirmation of Protective Effect of Peptide C

To confirm the vaccine effect of Peptides C obtained in Example 12, a challenge test was carried out as described in Example 7. A vaccine prepared by emulsifying Peptide C at the amount of antigen shown in Table 13 with oil adjuvant was once administered intramuscularly to the leg of SPF chickens of 4 weeks old for immunization. Four weeks after immunization, 0.2 mL of a solution containing A.pg-C 53-47 strain ($5.2 \times 10^9$ CFU/mL) was administered intranasally and clinical symptoms of a running nose, swelling of the face and epiphora were observed for a week.

As a result, as shown in Table 13, chicken administered with CΔ5-1-pQE and CΔ9-0-pQE exhibited excellent protective effects at 3 μg/dose. The protective effect of 60% was observed for the shortest CΔ6-4-pQE. From these results, it is expected that, for the protective effects to A.pg-C, a sequence at the C-terminal of non-homologous region (Region 2) in relation to A.pg-A is important and it was proved that a comparatively high protective effects were exhibited if the peptide includes at least the region of CΔ6-4. Furthermore, as shown in Example 9, it is expected that immunogenicity may be improved upon expression in fusion than expressed alone.

TABLE 13

| Vaccine | Amount of antigen | Protection rate |
| --- | --- | --- |
| CΔ5-1-pQE | 3 μg/dose | 100% |
| CΔ9-0-pQE | 3 μg/dose | 100% |
| CΔ9-2-pQE | 3 μg/dose | 60% |
| CΔ6-4-pQE | 3 μg/dose | 60% |
| No immunized control | — | 0% |

INDUSTRIAL APPLICABILITY

By using the present invention, a vaccine of avian infectious coryza caused by Avibacterium paragarinarum serotypes A and C may be provided.

The invention claimed is:

1. A process for preparing a recombinant avian infectious coryza vaccine, comprising: constructing a host that can produce as an inclusion body a fusion peptide comprising a peptide fragment (Peptide A) derived from HMTp210 protein of A.pg-A, wherein peptide A comprises the amino acid sequence of SEQ ID NO:35, and a peptide fragment (Peptide C) derived from HMTp210 protein of A.pg-C, wherein Peptide C comprises the amino acid sequence of SEQ ID NO:56; culturing the host and collecting and purifying a fraction of inclusion body from culture, to obtain a purified fraction of inclusion body; and preparing a preparation comprising the purified fraction of inclusion body, wherein Peptide A and Peptide C consist of 600 or less amino acid residues.

2. The process of claim 1, wherein Peptide A or Peptide C comprises an amino acid sequence where one or several amino acids are deleted, added, or replaced.

3. The process of claim 1, wherein a ratio of Peptide A and Peptide C in the fusion peptide is 1 to 3 of Peptide C to 1 of Peptide A.

4. The process of claim 1, wherein the fusion peptide comprises at least a structure where Peptide C is linked to the C-terminal of Peptide.

5. The process of claim 1, wherein the fusion peptide comprises a linker between Peptide A and Peptide A, Peptide C and Peptide C, or Peptide A and Peptide C.

6. The process of claim 1, wherein the fusion peptide comprises the amino acid sequence of SEQ ID NO:9.

7. A recombinant avian infectious coryza vaccine, comprising as an active ingredient a fusion peptide comprising a peptide fragment (Peptide A) derived from HMTp210 protein of *A.pg*-A, wherein peptide A comprises the amino acid sequence of SEQ ID NO:35, and a peptide fragment (Peptide C) derived from HMTp210 protein of *A.pg*-C, wherein Peptide C comprises the amino acid sequence of SEQ ID NO:56, wherein Peptide A and Peptide C consist of 600 or less amino acid residues.

8. The vaccine of claim 7, wherein Peptide A or Peptide C comprises an amino acid sequence where one or several amino acids are deleted, added, or replaced.

9. The vaccine of claim 7, wherein a ratio of Peptide A and Peptide C in the fusion peptide is 1 to 3 of Peptide C to 1 of Peptide A.

10. The vaccine of claim 7, wherein the fusion peptide comprises at least a structure where Peptide C is linked to the C-terminal of Peptide.

11. The vaccine of claim 7, wherein the fusion peptide has a linker between Peptide A and Peptide A, Peptide C and Peptide C, or Peptide A and Peptide C.

12. The vaccine of claim 7, wherein the fusion peptide comprises the amino acid sequence of SEQ ID NO:9.

13. A recombinant avian infectious coryza vaccine, comprising as an active ingredient a peptide that consists of an amino acid sequence within the amino acid sequence of SEQ ID NO:1 and comprises the amino acid sequence of SEQ ID NO: 35 with addition of 1 to 200 amino acid residues at at least one selected from the group consisting of the N-terminal and the C-terminal thereof.

14. The vaccine of claim 13, further comprising as an active ingredient, a peptide consisting of the amino acid sequence of SEQ ID NO: 1.

15. A recombinant avian infectious coryza vaccine, comprising as an active ingredient a peptide that consists of an amino acid sequence within the amino acid sequence of SEQ ID NO:3 and comprises the amino acid sequence of SEQ ID NO: 56, with addition of 1 to 200 amino acid residues at at least one selected from the group consisting of the N-terminal and the C-terminal thereof.

16. The vaccine of claim 15, further comprising, as an active ingredient, a peptide consisting of the amino acid sequence of SEQ ID NO: 3 or 52.

17. The vaccine of claim 14 or 16, wherein the peptide comprises an amino acid sequence wherein one or several amino acids are deleted, added, or replaced.

18. The process of claim 1, wherein the fusion peptide is either (1) or (2) as follows:

(1) a fusion peptide comprising a combination of Peptide A consisting of the amino acid sequence of SEQ ID NO: 1 and Peptide C consisting of the amino acid sequence selected from the group consisting of SEQ ID NOs: 2, 3, 4, 5, 6, 7, 50, 51, 52, 53, 54, and 56; or (2) a fusion peptide comprising a combination of Peptide C consisting of the amino acid sequence of SEQ ID NO: 3 and Peptide A consisting of the amino acid sequence of SEQ ID NO:35.

19. The process of claim 1, wherein the fusion peptide has the amino acid sequence of SEQ ID NO:49.

20. The process of claim 1, wherein the fusion peptide has the amino acid sequence of SEQ ID NO: 12.

21. The vaccine of claim 7, wherein the fusion peptide is either (1) or (2) as follows:

(1) a fusion peptide comprising a combination of Peptide A consisting of the amino acid sequence of SEQ ID NO: 1 and Peptide C consisting of the amino acid sequence selected from the group consisting of SEQ ID NOs: 2, 3, 4, 5, 6, 7, 50, 51, 52, 53, 54, and 56; or (2) a fusion peptide comprising a combination of Peptide C consisting of the amino acid sequence of SEQ ID NO: 3 and Peptide A consisting of the amino acid sequence of SEQ ID NO:35.

22. The vaccine of claim 7, wherein the fusion peptide comprises the amino acid sequence of SEQ ID NO:49.

23. The vaccine of claim 7, wherein the fusion peptide comprises the amino acid sequence of SEQ ID NO: 12.

* * * * *

SEQUENCE LISTING

<160> NUMBER OF SEQ ID NOS: 69

<210> SEQ ID NO 1
<211> LENGTH: 549
<212> TYPE: PRT
<213> ORGANISM: Avibacterium paragallinarum
<220> FEATURE:
<223> OTHER INFORMATION: type A

<400> SEQUENCE: 1

```
Met Asp Gly Thr Ile Thr Phe Thr Asn Ile Gly Gly Thr Gln Ala
1               5                   10                  15

Thr Ile His Asp Ala Ile Asn Asn Val Leu Thr Lys Gly Ile Tyr Leu
            20                  25                  30

Lys Ala Asp Gln Asn Asp Pro Thr Gly Asn Gln Gly Lys Val Glu
            35                  40                  45

Leu Gly Asn Ala Ile Thr Leu Ser Ala Thr Asn Gln Trp Ala Asn Asn
50                      55                  60

Gly Val Asn Tyr Lys Thr Asn Asn Leu Thr Thr Tyr Asn Ser Gln Asn
65                  70                  75                  80

Gly Thr Ile Leu Phe Gly Met Arg Glu Asp Pro Ser Val Lys Gln Ile
                85                  90                  95

Thr Ala Gly Thr Tyr Asn Thr Thr Gly Asp Ala Asn Asn Lys Asn Gln
                100                 105                 110

Leu Asn Asn Thr Leu Gln Gln Thr Thr Leu Glu Ala Thr Gly Ile Thr
            115                 120                 125

Ser Ser Val Gly Ser Thr Asn Tyr Ala Gly Phe Ser Leu Gly Ala Asp
            130                 135                 140

Ser Val Thr Phe Ser Lys Gly Ala Gly Thr Val Lys Leu Ser Gly
145                 150                 155                 160

Val Ser Asp Ala Thr Ala Asp Thr Asp Ala Ala Thr Leu Lys Gln Val
                165                 170                 175

Lys Glu Tyr Arg Thr Thr Leu Val Gly Asp Asn Asp Ile Thr Ala Ala
                180                 185                 190

Asp Arg Ser Gly Gly Thr Ser Asn Gly Ile Thr Tyr Asn Leu Ser Leu
            195                 200                 205

Asn Lys Gly Thr Val Ser Ala Thr Glu Glu Lys Val Val Ser Gly Lys
            210                 215                 220

Thr Val Tyr Glu Ala Ile Arg Asn Ala Ile Thr Gly Asn Ile Phe Thr
225                 230                 235                 240

Ile Gly Leu Asp Asp Thr Thr Leu Asn Lys Ile Asn Asn Pro Ala Asp
                245                 250                 255

Gln Asp Leu Ser Asn Leu Ser Glu Ser Gly Lys Asn Ala Ile Thr Gly
                260                 265                 270

Leu Val Asp Val Val Lys Lys Thr Asn Ser Pro Ile Thr Val Glu Pro
            275                 280                 285

Ser Thr Asp Ser Asn Lys Lys Lys Thr Phe Thr Val Gly Val Asp Phe
            290                 295                 300

Thr Asp Thr Ile Thr Glu Gly Asp Ala Thr Asp Lys Lys Leu Thr
305                 310                 315                 320

Thr Ser Lys Ser Val Glu Ser Tyr Val Thr Asn Lys Leu Ala Asn Phe
                325                 330                 335

Ser Thr Asp Ile Leu Leu Ser Asp Gly Arg Ser Gly Asn Ala Thr Thr
            340                 345                 350

Ala Asn Asp Gly Val Gly Lys Arg Arg Leu Ser Asp Gly Phe Thr Ile
            355                 360                 365

Lys Ser Glu Asn Phe Thr Leu Gly Ser Lys Gln Tyr Asn Gly Ser Asp
370                 375                 380

Ser Leu Gly Val Met Tyr Asp Asp Gln Asn Gly Val Phe Lys Leu Ser
385                 390                 395                 400

Leu Asn Met Thr Ala Leu Thr Thr Ser Leu Ala Asn Thr Phe Ala Lys
                405                 410                 415

Leu Asp Ala Ser Asn Leu Thr Asp Asp Ser Asn Lys Glu Lys Trp Arg
```

```
                  420                 425                 430
Thr Ala Leu Asn Val Tyr Ser Lys Thr Glu Val Asp Ala Glu Ile Gln
            435                 440                 445
Lys Ser Lys Val Thr Leu Thr Pro Asp Ser Gly Leu Ile Phe Ala Thr
450                 455                 460
Lys Gln Ala Gly Ser Gly Asn Asn Ala Gly Ile Asp Ala Gly Asn Lys
465                 470                 475                 480
Lys Ile Ser Asn Val Ala Asp Gly Asp Ile Ser Pro Thr Ser Gly Asp
                485                 490                 495
Val Val Thr Gly Arg Gln Leu Tyr Ala Leu Met Gln Lys Gly Ile Arg
            500                 505                 510
Val Tyr Gly Asp Glu Val Ser Pro Thr Lys Thr Gln Thr Thr Ala Pro
        515                 520                 525
Thr Asn Ala Asn Pro Thr Ala Thr Thr Ala Pro Thr Ala Ser Ser Thr
    530                 535                 540
Gln Gly Gly Ser Ala
545

<210> SEQ ID NO 2
<211> LENGTH: 574
<212> TYPE: PRT
<213> ORGANISM: Avibacterium paragallinarum
<220> FEATURE:
<223> OTHER INFORMATION: type C

<400> SEQUENCE: 2

Arg Gly Ser Gly Ser Gln Leu Tyr Ala Thr Asn Phe Met Leu Asn Lys
1               5                   10                  15
Leu Ala Gln Ser Val Lys Thr Asn Phe Gly Gly Asn Ala Asn Leu Ala
            20                  25                  30
Thr Asp Gly Thr Ile Thr Phe Thr Asn Ile Gly Gly Thr Gly Gln Asp
        35                  40                  45
Thr Ile His Asp Ala Ile Asn Asn Val Leu Thr Lys Leu Ile Ser Leu
    50                  55                  60
Ser Ala Thr Glu Glu Glu Val Val Ser Gly Glu Ala Val Tyr Asp
65                  70                  75                  80
Ala Leu Lys Gly Ala Lys Pro Thr Val Ser Ala Glu Ala Asn Lys Gly
                85                  90                  95
Ile Thr Gly Leu Val Asp Val Val Lys Lys Ala Asn Ser Pro Ile Thr
            100                 105                 110
Val Glu Pro Ser Thr Asp Asn Lys Lys Thr Phe Thr Val Gly
        115                 120                 125
Leu Met Lys Asp Ile Glu Gly Val Asn Ser Ile Thr Phe Asp Lys Ser
    130                 135                 140
Gly Gln Asp Leu Asn Gln Val Thr Gly Arg Met Ser Ser Ala Gly Leu
145                 150                 155                 160
Thr Phe Lys Lys Gly Asp Thr Thr Asn Gly Ser Thr Thr Thr Phe Ala
                165                 170                 175
Glu Asp Gly Leu Thr Ile Asp Ser Thr Thr Asn Ser Ala Gln Thr Asn
            180                 185                 190
Leu Val Lys Val Ser Arg Asp Gly Phe Ser Val Lys Asn Gly Ser Asp
        195                 200                 205
Glu Ser Lys Leu Ala Ser Thr Lys Leu Ser Ile Gly Ala Glu Asn Ala
    210                 215                 220
Glu His Val Glu Val Thr Lys Ser Gly Ile Ala Leu Lys Ala Asp Asn
225                 230                 235                 240
```

Thr Ser Asp Lys Ser Ser Ile Thr Leu Ala Gln Asp Ala Ile Thr Leu
            245                 250                 255

Ala Gly Asn Ala Thr Gly Thr Ala Ile Lys Leu Thr Gly Val Ala Asp
        260                 265                 270

Gly Asn Ile Thr Val Asn Ser Lys Asp Ala Val Asn Gly Gly Gln Leu
            275                 280                 285

Arg Thr Leu Leu Gly Val Asp Ser Gly Ala Lys Ile Gly Gly Thr Glu
290                 295                 300

Lys Thr Thr Ile Ser Glu Ala Ile Ser Asp Val Lys Gln Ala Leu Thr
305                 310                 315                 320

Asp Ala Thr Leu Ala Tyr Lys Ala Asp Lys Asn Gly Lys Thr Val
                325                 330                 335

Lys Leu Thr Asp Gly Leu Asn Phe Thr Ser Thr Thr Asn Ile Asp Ala
            340                 345                 350

Ser Val Glu Asp Asn Gly Val Val Lys Phe Thr Leu Lys Asp Lys Leu
        355                 360                 365

Thr Gly Leu Lys Thr Ile Ala Thr Glu Ser Leu Asn Ala Ser Gln Asn
    370                 375                 380

Ile Ile Ala Gly Gly Thr Val Thr Val Gly Glu Thr Glu Gly Ile
385                 390                 395                 400

Val Leu Thr Lys Ser Gly Ser Gly Asn Asp Arg Thr Leu Ser Leu Ser
            405                 410                 415

Gly Ala Gly Asn Ala Ala Thr Asp Gly Ile Lys Val Ser Gly Val Lys
        420                 425                 430

Ala Gly Thr Ala Asp Thr Asp Ala Val Asn Lys Gly Gln Leu Asp Lys
    435                 440                 445

Leu Phe Lys Ala Ile Asn Asp Ala Leu Gly Thr Thr Asp Leu Ala Val
    450                 455                 460

Thr Lys Asn Pro Asn Gln Thr Ser Ile Phe Asn Pro Ile Asn Gly Thr
465                 470                 475                 480

Ala Pro Thr Thr Phe Lys Asp Ala Val Asp Lys Leu Thr Thr Ala Val
            485                 490                 495

Asn Thr Gly Trp Gly Ser Lys Val Gly Ile Leu Ala Thr Gly Ile Asp
        500                 505                 510

Gly Ile Asp Ala Gly Asn Lys Lys Ile Ser Asn Val Ala Asp Gly Asp
    515                 520                 525

Ile Ser Pro Thr Ser Gly Asp Val Val Thr Gly Arg Gln Leu Tyr Ala
    530                 535                 540

Leu Met Gln Lys Gly Ile Arg Val Tyr Gly Asp Glu Val Ser Pro Thr
545                 550                 555                 560

Lys Thr Gln Thr Thr Ala Pro Thr Ala Ser Ser Thr Gln Gly
            565                 570

<210> SEQ ID NO 3
<211> LENGTH: 545
<212> TYPE: PRT
<213> ORGANISM: Avibacterium paragallinarum
<220> FEATURE:
<223> OTHER INFORMATION: type C

<400> SEQUENCE: 3

Arg Arg Gly Ser Asp Gly Thr Ile Thr Phe Thr Asn Ile Gly Gly Thr
1               5                   10                  15

Gly Gln Asp Thr Ile His Asp Ala Ile Asn Asn Val Leu Thr Lys Leu
            20                  25                  30

-continued

```
Ile Ser Leu Ser Ala Thr Glu Glu Glu Val Val Ser Gly Glu Ala
         35                  40                  45
Val Tyr Asp Ala Leu Lys Gly Ala Lys Pro Thr Val Ser Ala Glu Ala
 50                  55                  60
Asn Lys Gly Ile Thr Gly Leu Val Asp Val Val Lys Lys Ala Asn Ser
 65                  70                  75                  80
Pro Ile Thr Val Glu Pro Ser Thr Asp Asn Lys Lys Lys Thr Phe
                 85                  90                  95
Thr Val Gly Leu Met Lys Asp Ile Glu Gly Val Asn Ser Ile Thr Phe
                100                 105                 110
Asp Lys Ser Gly Gln Asp Leu Asn Gln Val Thr Gly Arg Met Ser Ser
                115                 120                 125
Ala Gly Leu Thr Phe Lys Lys Gly Asp Thr Thr Asn Gly Ser Thr Thr
            130                 135                 140
Thr Phe Ala Glu Asp Gly Leu Thr Ile Asp Ser Thr Thr Asn Ser Ala
145                 150                 155                 160
Gln Thr Asn Leu Val Lys Val Ser Arg Asp Gly Phe Ser Val Lys Asn
                165                 170                 175
Gly Ser Asp Glu Ser Lys Leu Ala Ser Thr Lys Leu Ser Ile Gly Ala
            180                 185                 190
Glu Asn Ala Glu His Val Glu Val Thr Lys Ser Gly Ile Ala Leu Lys
        195                 200                 205
Ala Asp Asn Thr Ser Asp Lys Ser Ser Ile Thr Leu Ala Gln Asp Ala
    210                 215                 220
Ile Thr Leu Ala Gly Asn Ala Thr Gly Thr Ala Ile Lys Leu Thr Gly
225                 230                 235                 240
Val Ala Asp Gly Asn Ile Thr Val Asn Ser Lys Asp Ala Val Asn Gly
                245                 250                 255
Gly Gln Leu Arg Thr Leu Leu Gly Val Asp Ser Gly Ala Lys Ile Gly
            260                 265                 270
Gly Thr Glu Lys Thr Thr Ile Ser Glu Ala Ile Ser Asp Val Lys Gln
        275                 280                 285
Ala Leu Thr Asp Ala Thr Leu Ala Tyr Lys Ala Asp Asn Lys Asn Gly
    290                 295                 300
Lys Thr Val Lys Leu Thr Asp Gly Leu Asn Phe Thr Ser Thr Thr Asn
305                 310                 315                 320
Ile Asp Ala Ser Val Glu Asp Asn Gly Val Val Lys Phe Thr Leu Lys
                325                 330                 335
Asp Lys Leu Thr Gly Leu Lys Thr Ile Ala Thr Glu Ser Leu Asn Ala
            340                 345                 350
Ser Gln Asn Ile Ile Ala Gly Gly Thr Val Thr Val Gly Gly Glu Thr
        355                 360                 365
Glu Gly Ile Val Leu Thr Lys Ser Gly Ser Gly Asn Asp Arg Thr Leu
    370                 375                 380
Ser Leu Ser Gly Ala Gly Asn Ala Ala Thr Asp Gly Ile Lys Val Ser
385                 390                 395                 400
Gly Val Lys Ala Gly Thr Ala Asp Thr Asp Ala Val Asn Lys Gly Gln
                405                 410                 415
Leu Asp Lys Leu Phe Lys Ala Ile Asn Asp Ala Leu Gly Thr Thr Asp
            420                 425                 430
Leu Ala Val Thr Lys Asn Pro Asn Gln Thr Ser Ile Phe Asn Pro Ile
        435                 440                 445
Asn Gly Thr Ala Pro Thr Thr Phe Lys Asp Ala Val Asp Lys Leu Thr
    450                 455                 460
```

```
Thr Ala Val Asn Thr Gly Trp Gly Ser Lys Val Gly Ile Leu Ala Thr
465                 470                 475                 480

Gly Ile Asp Gly Ile Asp Ala Gly Asn Lys Lys Ile Ser Asn Val Ala
                485                 490                 495

Asp Gly Asp Ile Ser Pro Thr Ser Gly Asp Val Val Thr Gly Arg Gln
            500                 505                 510

Leu Tyr Ala Leu Met Gln Lys Gly Ile Arg Val Tyr Gly Asp Glu Val
        515                 520                 525

Ser Pro Thr Lys Thr Gln Thr Thr Ala Pro Thr Ala Ser Ser Thr Gln
    530                 535                 540

Gly
545

<210> SEQ ID NO 4
<211> LENGTH: 387
<212> TYPE: PRT
<213> ORGANISM: Avibacterium paragallinarum
<220> FEATURE:
<223> OTHER INFORMATION: type C

<400> SEQUENCE: 4

Arg Gly Ser Gly Leu Met Lys Asp Ile Glu Gly Val Asn Ser Ile Thr
1               5                   10                  15

Phe Asp Lys Ser Gly Gln Asp Leu Asn Gln Val Thr Gly Arg Met Ser
            20                  25                  30

Ser Ala Gly Leu Thr Phe Lys Lys Gly Asp Thr Thr Asn Gly Ser Thr
        35                  40                  45

Thr Thr Phe Ala Glu Asp Gly Leu Thr Ile Asp Ser Thr Thr Asn Ser
    50                  55                  60

Ala Gln Thr Asn Leu Val Lys Val Ser Arg Asp Gly Phe Ser Val Lys
65                  70                  75                  80

Asn Gly Ser Asp Glu Ser Lys Leu Ala Ser Thr Lys Leu Ser Ile Gly
                85                  90                  95

Ala Glu Asn Ala Glu His Val Glu Val Thr Lys Ser Gly Ile Ala Leu
            100                 105                 110

Lys Ala Asp Asn Thr Ser Asp Lys Ser Ser Ile Thr Leu Ala Gln Asp
        115                 120                 125

Ala Ile Thr Leu Ala Gly Asn Ala Thr Gly Thr Ala Ile Lys Leu Thr
    130                 135                 140

Gly Val Ala Asp Gly Asn Ile Thr Val Asn Ser Lys Asp Ala Val Asn
145                 150                 155                 160

Gly Gly Gln Leu Arg Thr Leu Leu Gly Val Asp Ser Gly Ala Lys Ile
                165                 170                 175

Gly Gly Thr Glu Lys Thr Thr Ile Ser Glu Ala Ile Ser Asp Val Lys
            180                 185                 190

Gln Ala Leu Thr Asp Ala Thr Leu Ala Tyr Lys Ala Asp Asn Lys Asn
        195                 200                 205

Gly Lys Thr Val Lys Leu Thr Asp Gly Leu Asn Phe Thr Ser Thr Thr
    210                 215                 220

Asn Ile Asp Ala Ser Val Glu Asp Asn Gly Val Val Lys Phe Thr Leu
225                 230                 235                 240

Lys Asp Lys Leu Thr Gly Leu Lys Thr Ile Ala Thr Glu Ser Leu Asn
                245                 250                 255

Ala Ser Gln Asn Ile Ile Ala Gly Gly Thr Val Thr Val Gly Gly Glu
            260                 265                 270
```

```
Thr Glu Gly Ile Val Leu Thr Lys Ser Gly Ser Gly Asn Asp Arg Thr
        275                 280                 285

Leu Ser Leu Ser Gly Ala Gly Asn Ala Ala Thr Asp Gly Ile Lys Val
290                 295                 300

Ser Gly Val Lys Ala Gly Thr Ala Asp Thr Asp Ala Val Asn Lys Gly
305                 310                 315                 320

Gln Leu Asp Lys Leu Phe Lys Ala Ile Asn Asp Ala Leu Gly Thr Thr
                325                 330                 335

Asp Leu Ala Val Thr Lys Asn Pro Asn Gln Thr Ser Ile Phe Asn Pro
                340                 345                 350

Ile Asn Gly Thr Ala Pro Thr Thr Phe Lys Asp Ala Val Asp Lys Leu
                355                 360                 365

Thr Thr Ala Val Asn Thr Gly Trp Gly Ser Lys Val Gly Ile Leu Ala
370                 375                 380

Thr Gly Ile
385

<210> SEQ ID NO 5
<211> LENGTH: 573
<212> TYPE: PRT
<213> ORGANISM: Avibacterium paragallinarum
<220> FEATURE:
<223> OTHER INFORMATION: type C

<400> SEQUENCE: 5

Ser Arg Gly Ser Gln Leu Tyr Ala Thr Asn Phe Met Leu Asn Lys Leu
1               5                   10                  15

Ala Gln Ser Val Lys Thr Asn Phe Gly Gly Asn Ala Asn Leu Ala Thr
                20                  25                  30

Asp Gly Thr Ile Thr Phe Thr Asn Ile Gly Gly Thr Gly Gln Asp Thr
            35                  40                  45

Ile His Asp Ala Ile Asn Asn Val Leu Thr Lys Leu Ile Ser Leu Ser
        50                  55                  60

Ala Thr Glu Glu Glu Val Val Ser Gly Glu Ala Val Tyr Asp Ala
65                  70                  75                  80

Leu Lys Gly Ala Lys Pro Thr Val Ser Ala Glu Ala Asn Lys Gly Ile
                85                  90                  95

Thr Gly Leu Val Asp Val Val Lys Lys Ala Asn Ser Pro Ile Thr Val
            100                 105                 110

Glu Pro Ser Thr Asp Asn Asn Lys Lys Thr Phe Thr Val Gly Leu
        115                 120                 125

Met Lys Asp Ile Glu Gly Val Asn Ser Ile Thr Phe Asp Lys Ser Gly
130                 135                 140

Gln Asp Leu Asn Gln Val Thr Gly Arg Met Ser Ser Ala Gly Leu Thr
145                 150                 155                 160

Phe Lys Lys Gly Asp Thr Thr Asn Gly Ser Thr Thr Phe Ala Glu
                165                 170                 175

Asp Gly Leu Thr Ile Asp Ser Thr Thr Asn Ser Ala Gln Thr Asn Leu
            180                 185                 190

Val Lys Val Ser Arg Asp Gly Phe Ser Val Lys Asn Gly Ser Asp Glu
        195                 200                 205

Ser Lys Leu Ala Ser Thr Lys Leu Ser Ile Gly Ala Glu Asn Ala Glu
    210                 215                 220

His Val Glu Val Thr Lys Ser Gly Ile Ala Leu Lys Ala Asp Asn Thr
225                 230                 235                 240

Ser Asp Lys Ser Ser Ile Thr Leu Ala Gln Asp Ala Ile Thr Leu Ala
```

```
                245                 250                 255
Gly Asn Ala Thr Gly Thr Ala Ile Lys Leu Thr Gly Val Ala Asp Gly
            260                 265                 270

Asn Ile Thr Val Asn Ser Lys Asp Ala Val Asn Gly Gly Gln Leu Arg
        275                 280                 285

Thr Leu Leu Gly Val Asp Ser Gly Ala Lys Ile Gly Gly Thr Glu Lys
    290                 295                 300

Thr Thr Ile Ser Glu Ala Ile Ser Asp Val Lys Gln Ala Leu Thr Asp
305                 310                 315                 320

Ala Thr Leu Ala Tyr Lys Ala Asp Asn Lys Asn Gly Lys Thr Val Lys
                325                 330                 335

Leu Thr Asp Gly Leu Asn Phe Thr Ser Thr Thr Asn Ile Asp Ala Ser
            340                 345                 350

Val Glu Asp Asn Gly Val Val Lys Phe Thr Leu Lys Asp Lys Leu Thr
        355                 360                 365

Gly Leu Lys Thr Ile Ala Thr Glu Ser Leu Asn Ala Ser Gln Asn Ile
    370                 375                 380

Ile Ala Gly Gly Thr Val Thr Val Gly Gly Glu Thr Glu Gly Ile Val
385                 390                 395                 400

Leu Thr Lys Ser Gly Ser Gly Asn Asp Arg Thr Leu Ser Leu Ser Gly
                405                 410                 415

Ala Gly Asn Ala Ala Thr Asp Gly Ile Lys Val Ser Gly Val Lys Ala
            420                 425                 430

Gly Thr Ala Asp Thr Asp Ala Val Asn Lys Gly Gln Leu Asp Lys Leu
        435                 440                 445

Phe Lys Ala Ile Asn Asp Ala Leu Gly Thr Thr Asp Leu Ala Val Thr
    450                 455                 460

Lys Asn Pro Asn Gln Thr Ser Ile Phe Asn Pro Ile Asn Gly Thr Ala
465                 470                 475                 480

Pro Thr Thr Phe Lys Asp Ala Val Asp Lys Leu Thr Thr Ala Val Asn
                485                 490                 495

Thr Gly Trp Gly Ser Lys Val Gly Ile Leu Ala Thr Gly Ile Asp Gly
            500                 505                 510

Ile Asp Ala Gly Asn Lys Lys Ile Ser Asn Val Ala Asp Gly Asp Ile
        515                 520                 525

Ser Pro Thr Ser Gly Asp Val Val Thr Gly Arg Gln Leu Tyr Ala Leu
    530                 535                 540

Met Gln Lys Gly Ile Arg Val Tyr Gly Asp Glu Val Ser Pro Thr Lys
545                 550                 555                 560

Thr Gln Thr Thr Ala Pro Thr Ala Ser Ser Thr Gln Gly
                565                 570

<210> SEQ ID NO 6
<211> LENGTH: 543
<212> TYPE: PRT
<213> ORGANISM: Avibacterium paragallinarum
<220> FEATURE:
<223> OTHER INFORMATION: type C

<400> SEQUENCE: 6

Ser Arg Asp Gly Thr Ile Thr Phe Thr Asn Ile Gly Gly Thr Gly Gln
1               5                   10                  15

Asp Thr Ile His Asp Ala Ile Asn Asn Val Leu Thr Lys Leu Ile Ser
            20                  25                  30

Leu Ser Ala Thr Glu Glu Glu Glu Val Val Ser Gly Glu Ala Val Tyr
        35                  40                  45
```

```
Asp Ala Leu Lys Gly Ala Lys Pro Thr Val Ser Ala Glu Ala Asn Lys
    50                  55                  60

Gly Ile Thr Gly Leu Val Asp Val Val Lys Lys Ala Asn Ser Pro Ile
65                  70                  75                  80

Thr Val Glu Pro Ser Thr Asp Asn Asn Lys Lys Thr Phe Thr Val
                85                  90                  95

Gly Leu Met Lys Asp Ile Glu Gly Val Asn Ser Ile Thr Phe Asp Lys
                100                 105                 110

Ser Gly Gln Asp Leu Asn Gln Val Thr Gly Arg Met Ser Ser Ala Gly
                115                 120                 125

Leu Thr Phe Lys Lys Gly Asp Thr Asn Gly Ser Thr Thr Thr Phe
    130                 135                 140

Ala Glu Asp Gly Leu Thr Ile Asp Ser Thr Thr Asn Ser Ala Gln Thr
145                 150                 155                 160

Asn Leu Val Lys Val Ser Arg Asp Gly Phe Ser Val Lys Asn Gly Ser
                165                 170                 175

Asp Glu Ser Lys Leu Ala Ser Thr Lys Leu Ser Ile Gly Ala Glu Asn
                180                 185                 190

Ala Glu His Val Glu Val Thr Lys Ser Gly Ile Ala Leu Lys Ala Asp
                195                 200                 205

Asn Thr Ser Asp Lys Ser Ser Ile Thr Leu Ala Gln Asp Ala Ile Thr
    210                 215                 220

Leu Ala Gly Asn Ala Thr Gly Thr Ala Ile Lys Leu Thr Gly Val Ala
225                 230                 235                 240

Asp Gly Asn Ile Thr Val Asn Ser Lys Asp Ala Val Asn Gly Gln
                245                 250                 255

Leu Arg Thr Leu Leu Gly Val Asp Ser Gly Ala Lys Ile Gly Gly Thr
                260                 265                 270

Glu Lys Thr Thr Ile Ser Glu Ala Ile Ser Asp Val Lys Gln Ala Leu
                275                 280                 285

Thr Asp Ala Thr Leu Ala Tyr Lys Ala Asp Asn Lys Asn Gly Lys Thr
    290                 295                 300

Val Lys Leu Thr Asp Gly Leu Asn Phe Thr Ser Thr Asn Ile Asp
305                 310                 315                 320

Ala Ser Val Glu Asp Asn Gly Val Val Lys Phe Thr Leu Lys Asp Lys
                325                 330                 335

Leu Thr Gly Leu Lys Thr Ile Ala Thr Glu Ser Leu Asn Ala Ser Gln
                340                 345                 350

Asn Ile Ile Ala Gly Gly Thr Val Thr Val Gly Gly Glu Thr Glu Gly
    355                 360                 365

Ile Val Leu Thr Lys Ser Gly Ser Gly Asn Asp Arg Thr Leu Ser Leu
    370                 375                 380

Ser Gly Ala Gly Asn Ala Ala Thr Asp Gly Ile Lys Val Ser Gly Val
385                 390                 395                 400

Lys Ala Gly Thr Ala Asp Thr Asp Ala Val Asn Lys Gly Gln Leu Asp
                405                 410                 415

Lys Leu Phe Lys Ala Ile Asn Asp Ala Leu Gly Thr Thr Asp Leu Ala
                420                 425                 430

Val Thr Lys Asn Pro Asn Gln Thr Ser Ile Phe Asn Pro Ile Asn Gly
                435                 440                 445

Thr Ala Pro Thr Thr Phe Lys Asp Ala Val Asp Lys Leu Thr Thr Ala
    450                 455                 460

Val Asn Thr Gly Trp Gly Ser Lys Val Gly Ile Leu Ala Thr Gly Ile
```

```
465                 470                 475                 480

Asp Gly Ile Asp Ala Gly Asn Lys Lys Ile Ser Asn Val Ala Asp Gly
                485                 490                 495

Asp Ile Ser Pro Thr Ser Gly Asp Val Val Thr Gly Arg Gln Leu Tyr
            500                 505                 510

Ala Leu Met Gln Lys Gly Ile Arg Val Tyr Gly Asp Glu Val Ser Pro
        515                 520                 525

Thr Lys Thr Gln Thr Thr Ala Pro Thr Ala Ser Ser Thr Gln Gly
    530                 535                 540

<210> SEQ ID NO 7
<211> LENGTH: 386
<212> TYPE: PRT
<213> ORGANISM: Avibacterium paragallinarum
<220> FEATURE:
<223> OTHER INFORMATION: type C

<400> SEQUENCE: 7

Ser Arg Gly Leu Met Lys Asp Ile Glu Gly Val Asn Ser Ile Thr Phe
1               5                   10                  15

Asp Lys Ser Gly Gln Asp Leu Asn Gln Val Thr Gly Arg Met Ser Ser
            20                  25                  30

Ala Gly Leu Thr Phe Lys Lys Gly Asp Thr Thr Asn Gly Ser Thr Thr
        35                  40                  45

Thr Phe Ala Glu Asp Gly Leu Thr Ile Asp Ser Thr Thr Asn Ser Ala
    50                  55                  60

Gln Thr Asn Leu Val Lys Val Ser Arg Asp Gly Phe Ser Val Lys Asn
65                  70                  75                  80

Gly Ser Asp Glu Ser Lys Leu Ala Ser Thr Lys Leu Ser Ile Gly Ala
                85                  90                  95

Glu Asn Ala Glu His Val Glu Val Thr Lys Ser Gly Ile Ala Leu Lys
            100                 105                 110

Ala Asp Asn Thr Ser Asp Lys Ser Ser Ile Thr Leu Ala Gln Asp Ala
        115                 120                 125

Ile Thr Leu Ala Gly Asn Ala Thr Gly Thr Ala Ile Lys Leu Thr Gly
    130                 135                 140

Val Ala Asp Gly Asn Ile Thr Val Asn Ser Lys Asp Ala Val Asn Gly
145                 150                 155                 160

Gly Gln Leu Arg Thr Leu Leu Gly Val Asp Ser Gly Ala Lys Ile Gly
                165                 170                 175

Gly Thr Glu Lys Thr Thr Ile Ser Glu Ala Ile Ser Asp Val Lys Gln
            180                 185                 190

Ala Leu Thr Asp Ala Thr Leu Ala Tyr Lys Ala Asp Asn Lys Asn Gly
        195                 200                 205

Lys Thr Val Lys Leu Thr Asp Gly Leu Asn Phe Thr Ser Thr Thr Asn
    210                 215                 220

Ile Asp Ala Ser Val Glu Asp Asn Gly Val Val Lys Phe Thr Leu Lys
225                 230                 235                 240

Asp Lys Leu Thr Gly Leu Lys Thr Ile Ala Thr Glu Ser Leu Asn Ala
                245                 250                 255

Ser Gln Asn Ile Ile Ala Gly Gly Thr Val Thr Val Gly Gly Glu Thr
            260                 265                 270

Glu Gly Ile Val Leu Thr Lys Ser Gly Ser Gly Asn Asp Arg Thr Leu
        275                 280                 285

Ser Leu Ser Gly Ala Gly Asn Ala Ala Thr Asp Gly Ile Lys Val Ser
    290                 295                 300
```

```
Gly Val Lys Ala Gly Thr Ala Asp Thr Asp Ala Val Asn Lys Gly Gln
305                 310                 315                 320

Leu Asp Lys Leu Phe Lys Ala Ile Asn Asp Ala Leu Gly Thr Thr Asp
                325                 330                 335

Leu Ala Val Thr Lys Asn Pro Asn Gln Thr Ser Ile Phe Asn Pro Ile
            340                 345                 350

Asn Gly Thr Ala Pro Thr Thr Phe Lys Asp Ala Val Asp Lys Leu Thr
        355                 360                 365

Thr Ala Val Asn Thr Gly Trp Gly Ser Lys Val Gly Ile Leu Ala Thr
370                 375                 380

Gly Ile
385

<210> SEQ ID NO 8
<211> LENGTH: 1119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: A fusion peptide consisting of membrane protein
      sections from each of Avibacterium paragallinarum types A and C

<400> SEQUENCE: 8

Met Asp Gly Thr Ile Thr Phe Thr Asn Ile Gly Gly Thr Gly Gln Ala
1               5                   10                  15

Thr Ile His Asp Ala Ile Asn Asn Val Leu Thr Lys Gly Ile Tyr Leu
            20                  25                  30

Lys Ala Asp Gln Asn Asp Pro Thr Gly Asn Gln Gly Gln Lys Val Glu
        35                  40                  45

Leu Gly Asn Ala Ile Thr Leu Ser Ala Thr Asn Gln Trp Ala Asn Asn
    50                  55                  60

Gly Val Asn Tyr Lys Thr Asn Asn Leu Thr Thr Tyr Asn Ser Gln Asn
65                  70                  75                  80

Gly Thr Ile Leu Phe Gly Met Arg Glu Asp Pro Ser Val Lys Gln Ile
                85                  90                  95

Thr Ala Gly Thr Tyr Asn Thr Thr Gly Asp Ala Asn Asn Lys Asn Gln
            100                 105                 110

Leu Asn Asn Thr Leu Gln Gln Thr Leu Glu Ala Thr Gly Ile Thr
        115                 120                 125

Ser Ser Val Gly Ser Thr Asn Tyr Ala Gly Phe Ser Leu Gly Ala Asp
    130                 135                 140

Ser Val Thr Phe Ser Lys Gly Ala Gly Thr Val Lys Leu Ser Gly
145                 150                 155                 160

Val Ser Asp Ala Thr Ala Asp Thr Asp Ala Ala Thr Leu Lys Gln Val
                165                 170                 175

Lys Glu Tyr Arg Thr Thr Leu Val Gly Asp Asn Asp Ile Thr Ala Ala
            180                 185                 190

Asp Arg Ser Gly Gly Thr Ser Asn Gly Ile Thr Tyr Asn Leu Ser Leu
        195                 200                 205

Asn Lys Gly Thr Val Ser Ala Thr Glu Glu Lys Val Val Ser Gly Lys
    210                 215                 220

Thr Val Tyr Glu Ala Ile Arg Asn Ala Ile Thr Gly Asn Ile Phe Thr
225                 230                 235                 240

Ile Gly Leu Asp Asp Thr Thr Leu Asn Lys Ile Asn Asn Pro Ala Asp
                245                 250                 255
```

```
Gln Asp Leu Ser Asn Leu Ser Glu Ser Gly Lys Asn Ala Ile Thr Gly
            260                 265                 270

Leu Val Asp Val Val Lys Lys Thr Asn Ser Pro Ile Thr Val Glu Pro
        275                 280                 285

Ser Thr Asp Ser Asn Lys Lys Lys Thr Phe Thr Val Gly Val Asp Phe
290                 295                 300

Thr Asp Thr Ile Thr Glu Gly Asp Ala Thr Asp Lys Lys Leu Thr
305                 310                 315                 320

Thr Ser Lys Ser Val Glu Ser Tyr Val Thr Asn Lys Leu Ala Asn Phe
            325                 330                 335

Ser Thr Asp Ile Leu Leu Ser Asp Gly Arg Ser Gly Asn Ala Thr Thr
        340                 345                 350

Ala Asn Asp Gly Val Gly Lys Arg Arg Leu Ser Asp Gly Phe Thr Ile
            355                 360                 365

Lys Ser Glu Asn Phe Thr Leu Gly Ser Lys Gln Tyr Asn Gly Ser Asp
    370                 375                 380

Ser Leu Gly Val Met Tyr Asp Asp Gln Asn Gly Val Phe Lys Leu Ser
385                 390                 395                 400

Leu Asn Met Thr Ala Leu Thr Thr Ser Leu Ala Asn Thr Phe Ala Lys
                405                 410                 415

Leu Asp Ala Ser Asn Leu Thr Asp Ser Asn Lys Glu Lys Trp Arg
        420                 425                 430

Thr Ala Leu Asn Val Tyr Ser Lys Thr Glu Val Asp Ala Glu Ile Gln
            435                 440                 445

Lys Ser Lys Val Thr Leu Thr Pro Asp Ser Gly Leu Ile Phe Ala Thr
    450                 455                 460

Lys Gln Ala Gly Ser Gly Asn Asn Ala Gly Ile Asp Ala Gly Asn Lys
465                 470                 475                 480

Lys Ile Ser Asn Val Ala Asp Gly Asp Ile Ser Pro Thr Ser Gly Asp
                485                 490                 495

Val Val Thr Gly Arg Gln Leu Tyr Ala Leu Met Gln Lys Gly Ile Arg
        500                 505                 510

Val Tyr Gly Asp Glu Val Ser Pro Thr Lys Thr Gln Thr Thr Ala Pro
            515                 520                 525

Thr Asn Ala Asn Pro Thr Ala Thr Thr Ala Pro Thr Ala Ser Ser Thr
    530                 535                 540

Gln Gly Gly Ser Gly Ser Gln Leu Tyr Ala Thr Asn Phe Met Leu Asn
545                 550                 555                 560

Lys Leu Ala Gln Ser Val Lys Thr Asn Phe Gly Gly Asn Ala Asn Leu
                565                 570                 575

Ala Thr Asp Gly Thr Ile Thr Phe Thr Asn Ile Gly Thr Gly Gln
        580                 585                 590

Asp Thr Ile His Asp Ala Ile Asn Asn Val Leu Thr Lys Leu Ile Ser
            595                 600                 605

Leu Ser Ala Thr Glu Glu Glu Val Val Ser Gly Glu Ala Val Tyr
    610                 615                 620

Asp Ala Leu Lys Gly Ala Lys Pro Thr Val Ser Ala Glu Ala Asn Lys
625                 630                 635                 640

Gly Ile Thr Gly Leu Val Asp Val Val Lys Lys Ala Asn Ser Pro Ile
                645                 650                 655

Thr Val Glu Pro Ser Thr Asp Asn Asn Lys Lys Lys Thr Phe Thr Val
        660                 665                 670

Gly Leu Met Lys Asp Ile Glu Gly Val Asn Ser Ile Thr Phe Asp Lys
```

-continued

```
              675                 680                 685
        Ser Gly Gln Asp Leu Asn Gln Val Thr Gly Arg Met Ser Ser Ala Gly
        690                 695                 700

Leu Thr Phe Lys Lys Gly Asp Thr Thr Asn Gly Ser Thr Thr Thr Phe
705                 710                 715                 720

Ala Glu Asp Gly Leu Thr Ile Asp Ser Thr Thr Asn Ser Ala Gln Thr
                    725                 730                 735

Asn Leu Val Lys Val Ser Arg Asp Gly Phe Ser Val Lys Asn Gly Ser
                740                 745                 750

Asp Glu Ser Lys Leu Ala Ser Thr Lys Leu Ser Ile Gly Ala Glu Asn
        755                 760                 765

Ala Glu His Val Glu Val Thr Lys Ser Gly Ile Ala Leu Lys Ala Asp
        770                 775                 780

Asn Thr Ser Asp Lys Ser Ser Ile Thr Leu Ala Gln Asp Ala Ile Thr
785                 790                 795                 800

Leu Ala Gly Asn Ala Thr Gly Thr Ala Ile Lys Leu Thr Gly Val Ala
                    805                 810                 815

Asp Gly Asn Ile Thr Val Asn Ser Lys Asp Ala Val Asn Gly Gly Gln
                820                 825                 830

Leu Arg Thr Leu Leu Gly Val Asp Ser Gly Ala Lys Ile Gly Gly Thr
        835                 840                 845

Glu Lys Thr Thr Ile Ser Glu Ala Ile Ser Asp Val Lys Gln Ala Leu
        850                 855                 860

Thr Asp Ala Thr Leu Ala Tyr Lys Ala Asp Asn Lys Asn Gly Lys Thr
865                 870                 875                 880

Val Lys Leu Thr Asp Gly Leu Asn Phe Thr Ser Thr Thr Asn Ile Asp
                    885                 890                 895

Ala Ser Val Glu Asp Asn Gly Val Val Lys Phe Thr Leu Lys Asp Lys
                900                 905                 910

Leu Thr Gly Leu Lys Thr Ile Ala Thr Glu Ser Leu Asn Ala Ser Gln
        915                 920                 925

Asn Ile Ile Ala Gly Gly Thr Val Thr Val Gly Gly Glu Thr Glu Gly
        930                 935                 940

Ile Val Leu Thr Lys Ser Gly Ser Gly Asn Asp Arg Thr Leu Ser Leu
945                 950                 955                 960

Ser Gly Ala Gly Asn Ala Ala Thr Asp Gly Ile Lys Val Ser Gly Val
                    965                 970                 975

Lys Ala Gly Thr Ala Asp Thr Asp Ala Val Asn Lys Gly Gln Leu Asp
                980                 985                 990

Lys Leu Phe Lys Ala Ile Asn Asp Ala Leu Gly Thr Thr Asp Leu Ala
        995                 1000                1005

Val Thr Lys Asn Pro Asn Gln Thr Ser Ile Phe Asn Pro Ile Asn
        1010                1015                1020

Gly Thr Ala Pro Thr Thr Phe Lys Asp Ala Val Asp Lys Leu Thr
        1025                1030                1035

Thr Ala Val Asn Thr Gly Trp Gly Ser Lys Val Gly Ile Leu Ala
        1040                1045                1050

Thr Gly Ile Asp Gly Ile Asp Ala Gly Asn Lys Lys Ile Ser Asn
        1055                1060                1065

Val Ala Asp Gly Asp Ile Ser Pro Thr Ser Gly Asp Val Val Thr
        1070                1075                1080

Gly Arg Gln Leu Tyr Ala Leu Met Gln Lys Gly Ile Arg Val Tyr
        1085                1090                1095
```

```
Gly Asp Glu Val Ser Pro Thr Lys Thr Gln Thr Thr Ala Pro Thr
    1100                1105                1110

Ala Ser Ser Thr Gln Gly
    1115

<210> SEQ ID NO 9
<211> LENGTH: 1089
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: A fusion peptide consisting of membrane protein
      sections from each of Avibacterium paragallinarum types A and C

<400> SEQUENCE: 9

Met Asp Gly Thr Ile Thr Phe Thr Asn Ile Gly Gly Thr Gly Gln Ala
1               5                   10                  15

Thr Ile His Asp Ala Ile Asn Asn Val Leu Thr Lys Gly Ile Tyr Leu
            20                  25                  30

Lys Ala Asp Gln Asn Asp Pro Thr Gly Asn Gln Gly Gln Lys Val Glu
        35                  40                  45

Leu Gly Asn Ala Ile Thr Leu Ser Ala Thr Asn Gln Trp Ala Asn Asn
    50                  55                  60

Gly Val Asn Tyr Lys Thr Asn Asn Leu Thr Thr Tyr Asn Ser Gln Asn
65                  70                  75                  80

Gly Thr Ile Leu Phe Gly Met Arg Glu Asp Pro Ser Val Lys Gln Ile
                85                  90                  95

Thr Ala Gly Thr Tyr Asn Thr Thr Gly Asp Ala Asn Asn Lys Asn Gln
            100                 105                 110

Leu Asn Asn Thr Leu Gln Gln Thr Leu Glu Ala Thr Gly Ile Thr
        115                 120                 125

Ser Ser Val Gly Ser Thr Asn Tyr Ala Gly Phe Ser Leu Gly Ala Asp
    130                 135                 140

Ser Val Thr Phe Ser Lys Gly Ala Gly Thr Val Lys Leu Ser Gly
145                 150                 155                 160

Val Ser Asp Ala Thr Ala Asp Thr Asp Ala Ala Thr Leu Lys Gln Val
                165                 170                 175

Lys Glu Tyr Arg Thr Thr Leu Val Gly Asp Asn Asp Ile Thr Ala Ala
            180                 185                 190

Asp Arg Ser Gly Gly Thr Ser Asn Gly Ile Thr Tyr Asn Leu Ser Leu
        195                 200                 205

Asn Lys Gly Thr Val Ser Ala Thr Glu Glu Lys Val Val Ser Gly Lys
    210                 215                 220

Thr Val Tyr Glu Ala Ile Arg Asn Ala Ile Thr Gly Asn Ile Phe Thr
225                 230                 235                 240

Ile Gly Leu Asp Asp Thr Thr Leu Asn Lys Ile Asn Asn Pro Ala Asp
                245                 250                 255

Gln Asp Leu Ser Asn Leu Ser Glu Ser Gly Lys Asn Ala Ile Thr Gly
            260                 265                 270

Leu Val Asp Val Val Lys Lys Thr Asn Ser Pro Ile Thr Val Glu Pro
        275                 280                 285

Ser Thr Asp Ser Asn Lys Lys Lys Thr Phe Thr Val Gly Val Asp Phe
    290                 295                 300

Thr Asp Thr Ile Thr Glu Gly Asp Ala Thr Asp Lys Lys Leu Thr
305                 310                 315                 320
```

```
Thr Ser Lys Ser Val Glu Ser Tyr Val Thr Asn Lys Leu Ala Asn Phe
                325                 330                 335

Ser Thr Asp Ile Leu Leu Ser Asp Gly Arg Ser Gly Asn Ala Thr Thr
            340                 345                 350

Ala Asn Asp Gly Val Gly Lys Arg Arg Leu Ser Asp Gly Phe Thr Ile
        355                 360                 365

Lys Ser Glu Asn Phe Thr Leu Gly Ser Lys Gln Tyr Asn Gly Ser Asp
    370                 375                 380

Ser Leu Gly Val Met Tyr Asp Asp Gln Asn Gly Val Phe Lys Leu Ser
385                 390                 395                 400

Leu Asn Met Thr Ala Leu Thr Thr Ser Leu Ala Asn Thr Phe Ala Lys
                405                 410                 415

Leu Asp Ala Ser Asn Leu Thr Asp Asp Ser Asn Lys Glu Lys Trp Arg
            420                 425                 430

Thr Ala Leu Asn Val Tyr Ser Lys Thr Glu Val Asp Ala Glu Ile Gln
        435                 440                 445

Lys Ser Lys Val Thr Leu Thr Pro Asp Ser Gly Leu Ile Phe Ala Thr
    450                 455                 460

Lys Gln Ala Gly Ser Gly Asn Asn Ala Gly Ile Asp Ala Gly Asn Lys
465                 470                 475                 480

Lys Ile Ser Asn Val Ala Asp Gly Asp Ile Ser Pro Thr Ser Gly Asp
                485                 490                 495

Val Val Thr Gly Arg Gln Leu Tyr Ala Leu Met Gln Lys Gly Ile Arg
            500                 505                 510

Val Tyr Gly Asp Glu Val Ser Pro Thr Lys Thr Gln Thr Thr Ala Pro
        515                 520                 525

Thr Asn Ala Asn Pro Thr Ala Thr Thr Ala Pro Thr Ala Ser Ser Thr
    530                 535                 540

Gln Gly Gly Ser Asp Gly Thr Ile Thr Phe Thr Asn Ile Gly Gly Thr
545                 550                 555                 560

Gly Gln Asp Thr Ile His Asp Ala Ile Asn Asn Val Leu Thr Lys Leu
                565                 570                 575

Ile Ser Leu Ser Ala Thr Glu Glu Glu Val Val Ser Gly Glu Ala
            580                 585                 590

Val Tyr Asp Ala Leu Lys Gly Ala Lys Pro Thr Val Ser Ala Glu Ala
        595                 600                 605

Asn Lys Gly Ile Thr Gly Leu Val Asp Val Lys Lys Ala Asn Ser
    610                 615                 620

Pro Ile Thr Val Glu Pro Ser Thr Asp Asn Lys Lys Lys Thr Phe
625                 630                 635                 640

Thr Val Gly Leu Met Lys Asp Ile Glu Gly Val Asn Ser Ile Thr Phe
                645                 650                 655

Asp Lys Ser Gly Gln Asp Leu Asn Gln Val Thr Gly Arg Met Ser Ser
            660                 665                 670

Ala Gly Leu Thr Phe Lys Lys Gly Asp Thr Thr Asn Gly Ser Thr Thr
        675                 680                 685

Thr Phe Ala Glu Asp Gly Leu Thr Ile Asp Ser Thr Thr Asn Ser Ala
    690                 695                 700

Gln Thr Asn Leu Val Lys Val Ser Arg Asp Gly Phe Ser Val Lys Asn
705                 710                 715                 720

Gly Ser Asp Glu Ser Lys Leu Ala Ser Thr Lys Leu Ser Ile Gly Ala
                725                 730                 735

Glu Asn Ala Glu His Val Glu Val Thr Lys Ser Gly Ile Ala Leu Lys
            740                 745                 750
```

```
Ala Asp Asn Thr Ser Asp Lys Ser Ile Thr Leu Ala Gln Asp Ala
        755                 760                 765

Ile Thr Leu Ala Gly Asn Ala Thr Gly Thr Ala Ile Lys Leu Thr Gly
770                 775                 780

Val Ala Asp Gly Asn Ile Thr Val Asn Ser Lys Asp Ala Val Asn Gly
785                 790                 795                 800

Gly Gln Leu Arg Thr Leu Gly Val Asp Ser Gly Ala Lys Ile Gly
            805                 810                 815

Gly Thr Glu Lys Thr Thr Ile Ser Glu Ala Ile Ser Asp Val Lys Gln
            820                 825                 830

Ala Leu Thr Asp Ala Thr Leu Ala Tyr Lys Ala Asp Asn Lys Asn Gly
        835                 840                 845

Lys Thr Val Lys Leu Thr Asp Gly Leu Asn Phe Thr Ser Thr Thr Asn
850                 855                 860

Ile Asp Ala Ser Val Glu Asp Asn Gly Val Val Lys Phe Thr Leu Lys
865                 870                 875                 880

Asp Lys Leu Thr Gly Leu Lys Thr Ile Ala Thr Glu Ser Leu Asn Ala
            885                 890                 895

Ser Gln Asn Ile Ile Ala Gly Gly Thr Val Thr Val Gly Gly Glu Thr
            900                 905                 910

Glu Gly Ile Val Leu Thr Lys Ser Gly Ser Gly Asn Asp Arg Thr Leu
            915                 920                 925

Ser Leu Ser Gly Ala Gly Asn Ala Ala Thr Asp Gly Ile Lys Val Ser
930                 935                 940

Gly Val Lys Ala Gly Thr Ala Asp Thr Asp Ala Val Asn Lys Gly Gln
945                 950                 955                 960

Leu Asp Lys Leu Phe Lys Ala Ile Asn Asp Ala Leu Gly Thr Thr Asp
            965                 970                 975

Leu Ala Val Thr Lys Asn Pro Asn Gln Thr Ser Ile Phe Asn Pro Ile
            980                 985                 990

Asn Gly Thr Ala Pro Thr Thr Phe Lys Asp Ala Val Asp Lys Leu Thr
            995                 1000                1005

Thr Ala Val Asn Thr Gly Trp Gly Ser Lys Val Gly Ile Leu Ala
        1010                1015                1020

Thr Gly Ile Asp Gly Ile Asp Ala Gly Asn Lys Lys Ile Ser Asn
        1025                1030                1035

Val Ala Asp Gly Asp Ile Ser Pro Thr Ser Gly Asp Val Val Thr
        1040                1045                1050

Gly Arg Gln Leu Tyr Ala Leu Met Gln Lys Gly Ile Arg Val Tyr
        1055                1060                1065

Gly Asp Glu Val Ser Pro Thr Lys Thr Gln Thr Thr Ala Pro Thr
        1070                1075                1080

Ala Ser Ser Thr Gln Gly
        1085

<210> SEQ ID NO 10
<211> LENGTH: 932
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: A fusion peptide consisting of a section of the
      membrane proteins from each of Avibacterium paragallinarum types A
      and C
```

<400> SEQUENCE: 10

```
Met Asp Gly Thr Ile Thr Phe Thr Asn Ile Gly Gly Thr Gly Gln Ala
1               5                   10                  15

Thr Ile His Asp Ala Ile Asn Asn Val Leu Thr Lys Gly Ile Tyr Leu
            20                  25                  30

Lys Ala Asp Gln Asn Asp Pro Thr Gly Asn Gln Gly Gln Lys Val Glu
        35                  40                  45

Leu Gly Asn Ala Ile Thr Leu Ser Ala Thr Asn Gln Trp Ala Asn Asn
    50                  55                  60

Gly Val Asn Tyr Lys Thr Asn Asn Leu Thr Thr Tyr Asn Ser Gln Asn
65                  70                  75                  80

Gly Thr Ile Leu Phe Gly Met Arg Glu Asp Pro Ser Val Lys Gln Ile
                85                  90                  95

Thr Ala Gly Thr Tyr Asn Thr Thr Gly Asp Ala Asn Asn Lys Asn Gln
            100                 105                 110

Leu Asn Asn Thr Leu Gln Gln Thr Thr Leu Glu Ala Thr Gly Ile Thr
        115                 120                 125

Ser Ser Val Gly Ser Thr Asn Tyr Ala Gly Phe Ser Leu Gly Ala Asp
    130                 135                 140

Ser Val Thr Phe Ser Lys Gly Ala Gly Thr Val Lys Leu Ser Gly
145                 150                 155                 160

Val Ser Asp Ala Thr Ala Asp Thr Asp Ala Ala Thr Leu Lys Gln Val
                165                 170                 175

Lys Glu Tyr Arg Thr Thr Leu Val Gly Asp Asn Asp Ile Thr Ala Ala
            180                 185                 190

Asp Arg Ser Gly Gly Thr Ser Asn Gly Ile Thr Tyr Asn Leu Ser Leu
        195                 200                 205

Asn Lys Gly Thr Val Ser Ala Thr Glu Glu Lys Val Val Ser Gly Lys
    210                 215                 220

Thr Val Tyr Glu Ala Ile Arg Asn Ala Ile Thr Gly Asn Ile Phe Thr
225                 230                 235                 240

Ile Gly Leu Asp Asp Thr Thr Leu Asn Lys Ile Asn Asn Pro Ala Asp
                245                 250                 255

Gln Asp Leu Ser Asn Leu Ser Glu Ser Gly Lys Asn Ala Ile Thr Gly
            260                 265                 270

Leu Val Asp Val Val Lys Lys Thr Asn Ser Pro Ile Thr Val Glu Pro
        275                 280                 285

Ser Thr Asp Ser Asn Lys Lys Lys Thr Phe Thr Val Gly Val Asp Phe
    290                 295                 300

Thr Asp Thr Ile Thr Glu Gly Asp Ala Thr Asp Lys Lys Leu Thr
305                 310                 315                 320

Thr Ser Lys Ser Val Glu Ser Tyr Val Thr Asn Lys Leu Ala Asn Phe
                325                 330                 335

Ser Thr Asp Ile Leu Leu Ser Asp Gly Arg Ser Gly Asn Ala Thr Thr
            340                 345                 350

Ala Asn Asp Gly Val Gly Lys Arg Arg Leu Ser Asp Gly Phe Thr Ile
        355                 360                 365

Lys Ser Glu Asn Phe Thr Leu Gly Ser Lys Gln Tyr Asn Gly Ser Asp
    370                 375                 380

Ser Leu Gly Val Met Tyr Asp Asp Gln Asn Gly Val Phe Lys Leu Ser
385                 390                 395                 400

Leu Asn Met Thr Ala Leu Thr Thr Ser Leu Ala Asn Thr Phe Ala Lys
                405                 410                 415
```

-continued

```
Leu Asp Ala Ser Asn Leu Thr Asp Asp Ser Asn Lys Glu Lys Trp Arg
            420                 425                 430

Thr Ala Leu Asn Val Tyr Ser Lys Thr Glu Val Asp Ala Glu Ile Gln
            435                 440                 445

Lys Ser Lys Val Thr Leu Thr Pro Asp Ser Gly Leu Ile Phe Ala Thr
450                 455                 460

Lys Gln Ala Gly Ser Gly Asn Asn Ala Gly Ile Asp Ala Gly Asn Lys
465                 470                 475                 480

Lys Ile Ser Asn Val Ala Asp Gly Asp Ile Ser Pro Thr Ser Gly Asp
                485                 490                 495

Val Val Thr Gly Arg Gln Leu Tyr Ala Leu Met Gln Lys Gly Ile Arg
            500                 505                 510

Val Tyr Gly Asp Glu Val Ser Pro Thr Lys Thr Gln Thr Thr Ala Pro
            515                 520                 525

Thr Asn Ala Asn Pro Thr Ala Thr Ala Pro Thr Ala Ser Ser Thr
            530                 535                 540

Gln Gly Gly Ser Gly Leu Met Lys Asp Ile Glu Gly Val Asn Ser Ile
545                 550                 555                 560

Thr Phe Asp Lys Ser Gly Gln Asp Leu Asn Gln Val Thr Gly Arg Met
                565                 570                 575

Ser Ser Ala Gly Leu Thr Phe Lys Lys Gly Asp Thr Thr Asn Gly Ser
            580                 585                 590

Thr Thr Thr Phe Ala Glu Asp Gly Leu Thr Ile Asp Ser Thr Thr Asn
            595                 600                 605

Ser Ala Gln Thr Asn Leu Val Lys Val Ser Arg Asp Gly Phe Ser Val
            610                 615                 620

Lys Asn Gly Ser Asp Glu Ser Lys Leu Ala Ser Thr Lys Leu Ser Ile
625                 630                 635                 640

Gly Ala Glu Asn Ala Glu His Val Glu Val Thr Lys Ser Gly Ile Ala
                645                 650                 655

Leu Lys Ala Asp Asn Thr Ser Asp Lys Ser Ser Ile Thr Leu Ala Gln
            660                 665                 670

Asp Ala Ile Thr Leu Ala Gly Asn Ala Thr Gly Thr Ala Ile Lys Leu
            675                 680                 685

Thr Gly Val Ala Asp Gly Asn Ile Thr Val Asn Ser Lys Asp Ala Val
            690                 695                 700

Asn Gly Gly Gln Leu Arg Thr Leu Leu Gly Val Asp Ser Gly Ala Lys
705                 710                 715                 720

Ile Gly Gly Thr Glu Lys Thr Thr Ile Ser Glu Ala Ile Ser Asp Val
                725                 730                 735

Lys Gln Ala Leu Thr Asp Ala Thr Leu Ala Tyr Lys Ala Asp Asn Lys
            740                 745                 750

Asn Gly Lys Thr Val Lys Leu Thr Asp Gly Leu Asn Phe Thr Ser Thr
            755                 760                 765

Thr Asn Ile Asp Ala Ser Val Glu Asp Asn Gly Val Val Lys Phe Thr
            770                 775                 780

Leu Lys Asp Lys Leu Thr Gly Leu Lys Thr Ile Ala Thr Glu Ser Leu
785                 790                 795                 800

Asn Ala Ser Gln Asn Ile Ile Ala Gly Gly Thr Val Thr Val Gly Gly
                805                 810                 815

Glu Thr Glu Gly Ile Val Leu Thr Lys Ser Gly Ser Gly Asn Asp Arg
            820                 825                 830

Thr Leu Ser Leu Ser Gly Ala Gly Asn Ala Ala Thr Asp Gly Ile Lys
            835                 840                 845
```

-continued

```
Val Ser Gly Val Lys Ala Gly Thr Ala Asp Thr Asp Ala Val Asn Lys
    850                 855                 860

Gly Gln Leu Asp Lys Leu Phe Lys Ala Ile Asn Asp Ala Leu Gly Thr
865                 870                 875                 880

Thr Asp Leu Ala Val Thr Lys Asn Pro Asn Gln Thr Ser Ile Phe Asn
            885                 890                 895

Pro Ile Asn Gly Thr Ala Pro Thr Thr Phe Lys Asp Ala Val Asp Lys
        900                 905                 910

Leu Thr Thr Ala Val Asn Thr Gly Trp Gly Ser Lys Val Gly Ile Leu
            915                 920                 925

Ala Thr Gly Ile
        930

<210> SEQ ID NO 11
<211> LENGTH: 1131
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: A fusion peptide consisting of membrane protein
      sections from each of Avibacterium paragallinarum types A and C
      with a linker between the two sections

<400> SEQUENCE: 11

Met Asp Gly Thr Ile Thr Phe Thr Asn Ile Gly Gly Thr Gly Gln Ala
1               5                   10                  15

Thr Ile His Asp Ala Ile Asn Asn Val Leu Thr Lys Gly Ile Tyr Leu
            20                  25                  30

Lys Ala Asp Gln Asn Asp Pro Thr Gly Asn Gln Gly Gln Lys Val Glu
        35                  40                  45

Leu Gly Asn Ala Ile Thr Leu Ser Ala Thr Asn Gln Trp Ala Asn Asn
50                  55                  60

Gly Val Asn Tyr Lys Thr Asn Asn Leu Thr Thr Tyr Asn Ser Gln Asn
65                  70                  75                  80

Gly Thr Ile Leu Phe Gly Met Arg Glu Asp Pro Ser Val Lys Gln Ile
            85                  90                  95

Thr Ala Gly Thr Tyr Asn Thr Thr Gly Asp Ala Asn Asn Lys Asn Gln
        100                 105                 110

Leu Asn Asn Thr Leu Gln Gln Thr Thr Leu Glu Ala Thr Gly Ile Thr
    115                 120                 125

Ser Ser Val Gly Ser Thr Asn Tyr Ala Gly Phe Ser Leu Gly Ala Asp
130                 135                 140

Ser Val Thr Phe Ser Lys Gly Gly Ala Gly Thr Val Lys Leu Ser Gly
145                 150                 155                 160

Val Ser Asp Ala Thr Ala Asp Thr Asp Ala Ala Thr Leu Lys Gln Val
            165                 170                 175

Lys Glu Tyr Arg Thr Thr Leu Val Gly Asp Asn Asp Ile Thr Ala Ala
        180                 185                 190

Asp Arg Ser Gly Gly Thr Ser Asn Gly Ile Thr Tyr Asn Leu Ser Leu
    195                 200                 205

Asn Lys Gly Thr Val Ser Ala Thr Glu Glu Lys Val Val Ser Gly Lys
        210                 215                 220

Thr Val Tyr Glu Ala Ile Arg Asn Ala Ile Thr Gly Asn Ile Phe Thr
225                 230                 235                 240

Ile Gly Leu Asp Asp Thr Thr Leu Asn Lys Ile Asn Asn Pro Ala Asp
```

```
                    245                 250                 255
Gln Asp Leu Ser Asn Leu Ser Glu Ser Gly Lys Asn Ala Ile Thr Gly
                260                 265                 270

Leu Val Asp Val Val Lys Lys Thr Asn Ser Pro Ile Thr Val Glu Pro
            275                 280                 285

Ser Thr Asp Ser Asn Lys Lys Lys Thr Phe Thr Val Gly Val Asp Phe
        290                 295                 300

Thr Asp Thr Ile Thr Glu Gly Asp Ala Thr Asp Lys Lys Leu Thr
305                 310                 315                 320

Thr Ser Lys Ser Val Glu Ser Tyr Val Thr Asn Lys Leu Ala Asn Phe
                325                 330                 335

Ser Thr Asp Ile Leu Leu Ser Asp Gly Arg Ser Gly Asn Ala Thr Thr
            340                 345                 350

Ala Asn Asp Gly Val Gly Lys Arg Arg Leu Ser Asp Gly Phe Thr Ile
        355                 360                 365

Lys Ser Glu Asn Phe Thr Leu Gly Ser Lys Gln Tyr Asn Gly Ser Asp
    370                 375                 380

Ser Leu Gly Val Met Tyr Asp Asp Gln Asn Gly Val Phe Lys Leu Ser
385                 390                 395                 400

Leu Asn Met Thr Ala Leu Thr Thr Ser Leu Ala Asn Thr Phe Ala Lys
                405                 410                 415

Leu Asp Ala Ser Asn Leu Thr Asp Ser Asn Lys Glu Lys Trp Arg
            420                 425                 430

Thr Ala Leu Asn Val Tyr Ser Lys Thr Glu Val Asp Ala Glu Ile Gln
        435                 440                 445

Lys Ser Lys Val Thr Leu Thr Pro Asp Ser Gly Leu Ile Phe Ala Thr
    450                 455                 460

Lys Gln Ala Gly Ser Gly Asn Asn Ala Gly Ile Asp Ala Gly Asn Lys
465                 470                 475                 480

Lys Ile Ser Asn Val Ala Asp Gly Asp Ile Ser Pro Thr Ser Gly Asp
                485                 490                 495

Val Val Thr Gly Arg Gln Leu Tyr Ala Leu Met Gln Lys Gly Ile Arg
            500                 505                 510

Val Tyr Gly Asp Glu Val Ser Pro Thr Lys Thr Gln Thr Thr Ala Pro
        515                 520                 525

Thr Asn Ala Asn Pro Thr Ala Thr Thr Ala Pro Thr Ala Ser Ser Thr
    530                 535                 540

Gln Gly Gly Ser Gly Gly Gly Gly Gly Gly Gly Gly Gly Gly Ser Arg
545                 550                 555                 560

Gly Ser Gln Leu Tyr Ala Thr Asn Phe Met Leu Asn Lys Leu Ala Gln
                565                 570                 575

Ser Val Lys Thr Asn Phe Gly Gly Asn Ala Asn Leu Ala Thr Asp Gly
            580                 585                 590

Thr Ile Thr Phe Thr Asn Ile Gly Gly Thr Gly Gln Asp Thr Ile His
        595                 600                 605

Asp Ala Ile Asn Asn Val Leu Thr Lys Leu Ile Ser Leu Ser Ala Thr
    610                 615                 620

Glu Glu Glu Glu Val Val Ser Gly Glu Ala Val Tyr Asp Ala Leu Lys
625                 630                 635                 640

Gly Ala Lys Pro Thr Val Ser Ala Glu Ala Asn Lys Gly Ile Thr Gly
                645                 650                 655

Leu Val Asp Val Val Lys Lys Ala Asn Ser Pro Ile Thr Val Glu Pro
            660                 665                 670
```

-continued

Ser Thr Asp Asn Asn Lys Lys Lys Thr Phe Thr Val Gly Leu Met Lys
    675                 680                 685

Asp Ile Glu Gly Val Asn Ser Ile Thr Phe Asp Lys Ser Gly Gln Asp
690                 695                 700

Leu Asn Gln Val Thr Gly Arg Met Ser Ser Ala Gly Leu Thr Phe Lys
705                 710                 715                 720

Lys Gly Asp Thr Thr Asn Gly Ser Thr Thr Thr Phe Ala Glu Asp Gly
            725                 730                 735

Leu Thr Ile Asp Ser Thr Thr Asn Ser Ala Gln Thr Asn Leu Val Lys
            740                 745                 750

Val Ser Arg Asp Gly Phe Ser Val Lys Asn Gly Ser Asp Glu Ser Lys
            755                 760                 765

Leu Ala Ser Thr Lys Leu Ser Ile Gly Ala Glu Asn Ala Glu His Val
    770                 775                 780

Glu Val Thr Lys Ser Gly Ile Ala Leu Lys Ala Asp Asn Thr Ser Asp
785                 790                 795                 800

Lys Ser Ser Ile Thr Leu Ala Gln Asp Ala Ile Thr Leu Ala Gly Asn
            805                 810                 815

Ala Thr Gly Thr Ala Ile Lys Leu Thr Gly Val Ala Asp Gly Asn Ile
            820                 825                 830

Thr Val Asn Ser Lys Asp Ala Val Asn Gly Gly Gln Leu Arg Thr Leu
835                 840                 845

Leu Gly Val Asp Ser Gly Ala Lys Ile Gly Thr Glu Lys Thr Thr
    850                 855                 860

Ile Ser Glu Ala Ile Ser Asp Val Lys Gln Ala Leu Thr Asp Ala Thr
865                 870                 875                 880

Leu Ala Tyr Lys Ala Asp Asn Lys Asn Gly Lys Thr Val Lys Leu Thr
            885                 890                 895

Asp Gly Leu Asn Phe Thr Ser Thr Thr Asn Ile Asp Ala Ser Val Glu
            900                 905                 910

Asp Asn Gly Val Val Lys Phe Thr Leu Lys Asp Lys Leu Thr Gly Leu
            915                 920                 925

Lys Thr Ile Ala Thr Glu Ser Leu Asn Ala Ser Gln Asn Ile Ile Ala
930                 935                 940

Gly Gly Thr Val Thr Val Gly Gly Glu Thr Glu Gly Ile Val Leu Thr
945                 950                 955                 960

Lys Ser Gly Ser Gly Asn Asp Arg Thr Leu Ser Leu Ser Gly Ala Gly
            965                 970                 975

Asn Ala Ala Thr Asp Gly Ile Lys Val Ser Gly Val Lys Ala Gly Thr
            980                 985                 990

Ala Asp Thr Asp Ala Val Asn Lys Gly Gln Leu Asp Lys Leu Phe Lys
            995                 1000                1005

Ala Ile Asn Asp Ala Leu Gly Thr Thr Asp Leu Ala Val Thr Lys
    1010                1015                1020

Asn Pro Asn Gln Thr Ser Ile Phe Asn Pro Ile Asn Gly Thr Ala
    1025                1030                1035

Pro Thr Thr Phe Lys Asp Ala Val Asp Lys Leu Thr Thr Ala Val
    1040                1045                1050

Asn Thr Gly Trp Gly Ser Lys Val Gly Ile Leu Ala Thr Gly Ile
    1055                1060                1065

Asp Gly Ile Asp Ala Gly Asn Lys Lys Ile Ser Asn Val Ala Asp
    1070                1075                1080

Gly Asp Ile Ser Pro Thr Ser Gly Asp Val Val Thr Gly Arg Gln
    1085                1090                1095

```
Leu Tyr Ala Leu Met Gln Lys Gly Ile Arg Val Tyr Gly Asp Glu
    1100            1105                1110

Val Ser Pro Thr Lys Thr Gln Thr Thr Ala Pro Thr Ala Ser Ser
    1115            1120                1125

Thr Gln Gly
    1130

<210> SEQ ID NO 12
<211> LENGTH: 1101
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: A fusion peptide consisting of membrane protein
      sections from each of Avibacterium paragallinarum types A and C
      with a linker between the two sections

<400> SEQUENCE: 12

Met Asp Gly Thr Ile Thr Phe Thr Asn Ile Gly Gly Thr Gly Gln Ala
1               5                   10                  15

Thr Ile His Asp Ala Ile Asn Asn Val Leu Thr Lys Gly Ile Tyr Leu
            20                  25                  30

Lys Ala Asp Gln Asn Asp Pro Thr Gly Asn Gln Gly Gln Lys Val Glu
        35                  40                  45

Leu Gly Asn Ala Ile Thr Leu Ser Ala Thr Asn Gln Trp Ala Asn Asn
    50                  55                  60

Gly Val Asn Tyr Lys Thr Asn Asn Leu Thr Thr Tyr Asn Ser Gln Asn
65                  70                  75                  80

Gly Thr Ile Leu Phe Gly Met Arg Glu Asp Pro Ser Val Lys Gln Ile
                85                  90                  95

Thr Ala Gly Thr Tyr Asn Thr Thr Gly Asp Ala Asn Asn Lys Asn Gln
            100                 105                 110

Leu Asn Asn Thr Leu Gln Gln Thr Leu Glu Ala Thr Gly Ile Thr
        115                 120                 125

Ser Ser Val Gly Ser Thr Asn Tyr Ala Gly Phe Ser Leu Gly Ala Asp
    130                 135                 140

Ser Val Thr Phe Ser Lys Gly Gly Ala Gly Thr Val Lys Leu Ser Gly
145                 150                 155                 160

Val Ser Asp Ala Thr Ala Asp Thr Asp Ala Ala Thr Leu Lys Gln Val
                165                 170                 175

Lys Glu Tyr Arg Thr Thr Leu Val Gly Asp Asn Asp Ile Thr Ala Ala
            180                 185                 190

Asp Arg Ser Gly Gly Thr Ser Asn Gly Ile Thr Tyr Asn Leu Ser Leu
        195                 200                 205

Asn Lys Gly Thr Val Ser Ala Thr Glu Glu Lys Val Val Ser Gly Lys
    210                 215                 220

Thr Val Tyr Glu Ala Ile Arg Asn Ala Ile Thr Gly Asn Ile Phe Thr
225                 230                 235                 240

Ile Gly Leu Asp Asp Thr Thr Leu Asn Lys Ile Asn Asn Pro Ala Asp
                245                 250                 255

Gln Asp Leu Ser Asn Leu Ser Glu Ser Gly Lys Asn Ala Ile Thr Gly
            260                 265                 270

Leu Val Asp Val Val Lys Lys Thr Asn Ser Pro Ile Thr Val Glu Pro
        275                 280                 285

Ser Thr Asp Ser Asn Lys Lys Lys Thr Phe Thr Val Gly Val Asp Phe
```

-continued

```
               290                 295                 300
Thr Asp Thr Ile Thr Glu Gly Asp Ala Thr Asp Lys Lys Leu Thr
305                 310                 315                 320

Thr Ser Lys Ser Val Glu Ser Tyr Val Thr Asn Lys Leu Ala Asn Phe
                325                 330                 335

Ser Thr Asp Ile Leu Leu Ser Asp Gly Arg Ser Gly Asn Ala Thr Thr
                    340                 345                 350

Ala Asn Asp Gly Val Gly Lys Arg Arg Leu Ser Asp Gly Phe Thr Ile
            355                 360                 365

Lys Ser Glu Asn Phe Thr Leu Gly Ser Lys Gln Tyr Asn Gly Ser Asp
370                 375                 380

Ser Leu Gly Val Met Tyr Asp Asp Gln Asn Gly Val Phe Lys Leu Ser
385                 390                 395                 400

Leu Asn Met Thr Ala Leu Thr Ser Leu Ala Asn Thr Phe Ala Lys
                    405                 410                 415

Leu Asp Ala Ser Asn Leu Thr Asp Ser Asn Lys Glu Lys Trp Arg
            420                 425                 430

Thr Ala Leu Asn Val Tyr Ser Lys Thr Glu Val Asp Ala Glu Ile Gln
                435                 440                 445

Lys Ser Lys Val Thr Leu Thr Pro Asp Ser Gly Leu Ile Phe Ala Thr
450                 455                 460

Lys Gln Ala Gly Ser Gly Asn Asn Ala Gly Ile Asp Ala Gly Asn Lys
465                 470                 475                 480

Lys Ile Ser Asn Val Ala Asp Gly Asp Ile Ser Pro Thr Ser Gly Asp
                    485                 490                 495

Val Val Thr Gly Arg Gln Leu Tyr Ala Leu Met Gln Lys Gly Ile Arg
                500                 505                 510

Val Tyr Gly Asp Glu Val Ser Pro Thr Lys Thr Gln Thr Thr Ala Pro
            515                 520                 525

Thr Asn Ala Asn Pro Thr Ala Thr Thr Ala Pro Thr Ala Ser Ser Thr
530                 535                 540

Gln Gly Gly Ser Gly Gly Gly Gly Gly Gly Gly Gly Gly Ser Arg
545                 550                 555                 560

Asp Gly Thr Ile Thr Phe Thr Asn Ile Gly Gly Thr Gly Gln Asp Thr
                    565                 570                 575

Ile His Asp Ala Ile Asn Asn Val Leu Thr Lys Leu Ile Ser Leu Ser
                580                 585                 590

Ala Thr Glu Glu Glu Glu Val Val Ser Gly Glu Ala Val Tyr Asp Ala
            595                 600                 605

Leu Lys Gly Ala Lys Pro Thr Val Ser Ala Glu Ala Asn Lys Gly Ile
610                 615                 620

Thr Gly Leu Val Asp Val Val Lys Lys Ala Asn Ser Pro Ile Thr Val
625                 630                 635                 640

Glu Pro Ser Thr Asp Asn Asn Lys Lys Thr Phe Thr Val Gly Leu
                    645                 650                 655

Met Lys Asp Ile Glu Gly Val Asn Ser Ile Thr Phe Asp Lys Ser Gly
                660                 665                 670

Gln Asp Leu Asn Gln Val Thr Gly Arg Met Ser Ser Ala Gly Leu Thr
            675                 680                 685

Phe Lys Lys Gly Asp Thr Thr Asn Gly Ser Thr Thr Thr Phe Ala Glu
690                 695                 700

Asp Gly Leu Thr Ile Asp Ser Thr Thr Asn Ser Ala Gln Thr Asn Leu
705                 710                 715                 720
```

```
Val Lys Val Ser Arg Asp Gly Phe Ser Val Lys Asn Gly Ser Asp Glu
            725                 730                 735

Ser Lys Leu Ala Ser Thr Lys Leu Ser Ile Gly Ala Glu Asn Ala Glu
        740                 745                 750

His Val Glu Val Thr Lys Ser Gly Ile Ala Leu Lys Ala Asp Asn Thr
        755                 760                 765

Ser Asp Lys Ser Ser Ile Thr Leu Ala Gln Asp Ala Ile Thr Leu Ala
        770                 775                 780

Gly Asn Ala Thr Gly Thr Ala Ile Lys Leu Thr Gly Val Ala Asp Gly
785                 790                 795                 800

Asn Ile Thr Val Asn Ser Lys Asp Ala Val Asn Gly Gly Gln Leu Arg
                805                 810                 815

Thr Leu Leu Gly Val Asp Ser Gly Ala Lys Ile Gly Thr Glu Lys
            820                 825                 830

Thr Thr Ile Ser Glu Ala Ile Ser Asp Val Lys Gln Ala Leu Thr Asp
            835                 840                 845

Ala Thr Leu Ala Tyr Lys Ala Asp Asn Lys Asn Gly Lys Thr Val Lys
    850                 855                 860

Leu Thr Asp Gly Leu Asn Phe Thr Ser Thr Thr Asn Ile Asp Ala Ser
865                 870                 875                 880

Val Glu Asp Asn Gly Val Val Lys Phe Thr Leu Lys Asp Lys Leu Thr
                885                 890                 895

Gly Leu Lys Thr Ile Ala Thr Glu Ser Leu Asn Ala Ser Gln Asn Ile
            900                 905                 910

Ile Ala Gly Gly Thr Val Thr Val Gly Gly Thr Glu Gly Ile Val
            915                 920                 925

Leu Thr Lys Ser Gly Ser Gly Asn Asp Arg Thr Leu Ser Leu Ser Gly
930                 935                 940

Ala Gly Asn Ala Ala Thr Asp Gly Ile Lys Val Ser Gly Val Lys Ala
945                 950                 955                 960

Gly Thr Ala Asp Thr Asp Ala Val Asn Lys Gly Gln Leu Asp Lys Leu
                965                 970                 975

Phe Lys Ala Ile Asn Asp Ala Leu Gly Thr Thr Asp Leu Ala Val Thr
            980                 985                 990

Lys Asn Pro Asn Gln Thr Ser Ile Phe Asn Pro Ile Asn Gly Thr Ala
            995                1000                1005

Pro Thr Thr Phe Lys Asp Ala Val Asp Lys Leu Thr Thr Ala Val
   1010                1015                1020

Asn Thr Gly Trp Gly Ser Lys Val Gly Ile Leu Ala Thr Gly Ile
   1025                1030                1035

Asp Gly Ile Asp Ala Gly Asn Lys Lys Ile Ser Asn Val Ala Asp
   1040                1045                1050

Gly Asp Ile Ser Pro Thr Ser Gly Asp Val Val Thr Gly Arg Gln
   1055                1060                1065

Leu Tyr Ala Leu Met Gln Lys Gly Ile Arg Val Tyr Gly Asp Glu
   1070                1075                1080

Val Ser Pro Thr Lys Thr Gln Thr Thr Ala Pro Thr Ala Ser Ser
   1085                1090                1095

Thr Gln Gly
   1100

<210> SEQ ID NO 13
<211> LENGTH: 944
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: A fusion peptide consisting of membrane protein
      sections from each of Avibacterium paragallinarum types A and C
      with a linker between the two sections

<400> SEQUENCE: 13

Met Asp Gly Thr Ile Thr Phe Thr Asn Ile Gly Gly Thr Gly Gln Ala
1               5                   10                  15

Thr Ile His Asp Ala Ile Asn Asn Val Leu Thr Lys Gly Ile Tyr Leu
            20                  25                  30

Lys Ala Asp Gln Asn Asp Pro Thr Gly Asn Gln Gly Gln Lys Val Glu
        35                  40                  45

Leu Gly Asn Ala Ile Thr Leu Ser Ala Thr Asn Gln Trp Ala Asn Asn
    50                  55                  60

Gly Val Asn Tyr Lys Thr Asn Asn Leu Thr Thr Tyr Asn Ser Gln Asn
65                  70                  75                  80

Gly Thr Ile Leu Phe Gly Met Arg Glu Asp Pro Ser Val Lys Gln Ile
                85                  90                  95

Thr Ala Gly Thr Tyr Asn Thr Thr Gly Asp Ala Asn Asn Lys Asn Gln
            100                 105                 110

Leu Asn Asn Thr Leu Gln Gln Thr Thr Leu Glu Ala Thr Gly Ile Thr
        115                 120                 125

Ser Ser Val Gly Ser Thr Asn Tyr Ala Gly Phe Ser Leu Gly Ala Asp
    130                 135                 140

Ser Val Thr Phe Ser Lys Gly Gly Ala Gly Thr Val Lys Leu Ser Gly
145                 150                 155                 160

Val Ser Asp Ala Thr Ala Asp Thr Asp Ala Ala Thr Leu Lys Gln Val
                165                 170                 175

Lys Glu Tyr Arg Thr Thr Leu Val Gly Asp Asn Asp Ile Thr Ala Ala
            180                 185                 190

Asp Arg Ser Gly Gly Thr Ser Asn Gly Ile Thr Tyr Asn Leu Ser Leu
        195                 200                 205

Asn Lys Gly Thr Val Ser Ala Thr Glu Glu Lys Val Val Ser Gly Lys
    210                 215                 220

Thr Val Tyr Glu Ala Ile Arg Asn Ala Ile Thr Gly Asn Ile Phe Thr
225                 230                 235                 240

Ile Gly Leu Asp Asp Thr Thr Leu Asn Lys Ile Asn Asn Pro Ala Asp
                245                 250                 255

Gln Asp Leu Ser Asn Leu Ser Glu Ser Gly Lys Asn Ala Ile Thr Gly
            260                 265                 270

Leu Val Asp Val Val Lys Lys Thr Asn Ser Pro Ile Thr Val Glu Pro
        275                 280                 285

Ser Thr Asp Ser Asn Lys Lys Lys Thr Phe Thr Val Gly Val Asp Phe
    290                 295                 300

Thr Asp Thr Ile Thr Glu Gly Asp Ala Thr Asp Lys Lys Leu Thr
305                 310                 315                 320

Thr Ser Lys Ser Val Glu Ser Tyr Val Thr Asn Lys Leu Ala Asn Phe
                325                 330                 335

Ser Thr Asp Ile Leu Leu Ser Asp Gly Arg Ser Gly Asn Ala Thr Thr
            340                 345                 350

Ala Asn Asp Gly Val Gly Lys Arg Arg Leu Ser Asp Gly Phe Thr Ile
        355                 360                 365

Lys Ser Glu Asn Phe Thr Leu Gly Ser Lys Gln Tyr Asn Gly Ser Asp
```

```
                370                 375                 380
Ser Leu Gly Val Met Tyr Asp Asp Gln Asn Gly Val Phe Lys Leu Ser
385                 390                 395                 400

Leu Asn Met Thr Ala Leu Thr Thr Ser Leu Ala Asn Thr Phe Ala Lys
                405                 410                 415

Leu Asp Ala Ser Asn Leu Thr Asp Asp Ser Asn Lys Glu Lys Trp Arg
                420                 425                 430

Thr Ala Leu Asn Val Tyr Ser Lys Thr Glu Val Asp Ala Glu Ile Gln
                435                 440                 445

Lys Ser Lys Val Thr Leu Thr Pro Asp Ser Gly Leu Ile Phe Ala Thr
450                 455                 460

Lys Gln Ala Gly Ser Gly Asn Asn Ala Gly Ile Asp Ala Gly Asn Lys
465                 470                 475                 480

Lys Ile Ser Asn Val Ala Asp Gly Asp Ile Ser Pro Thr Ser Gly Asp
                485                 490                 495

Val Val Thr Gly Arg Gln Leu Tyr Ala Leu Met Gln Lys Gly Ile Arg
                500                 505                 510

Val Tyr Gly Asp Glu Val Ser Pro Thr Lys Thr Gln Thr Thr Ala Pro
                515                 520                 525

Thr Asn Ala Asn Pro Thr Ala Thr Ala Pro Thr Ala Ser Ser Thr
                530                 535                 540

Gln Gly Gly Ser Gly Gly Gly Gly Gly Gly Gly Gly Gly Ser Arg
545                 550                 555                 560

Gly Leu Met Lys Asp Ile Glu Gly Val Asn Ser Ile Thr Phe Asp Lys
                565                 570                 575

Ser Gly Gln Asp Leu Asn Gln Val Thr Gly Arg Met Ser Ser Ala Gly
                580                 585                 590

Leu Thr Phe Lys Lys Gly Asp Thr Thr Asn Gly Ser Thr Thr Thr Phe
                595                 600                 605

Ala Glu Asp Gly Leu Thr Ile Asp Ser Thr Thr Asn Ser Ala Gln Thr
                610                 615                 620

Asn Leu Val Lys Val Ser Arg Asp Gly Phe Ser Val Lys Asn Gly Ser
625                 630                 635                 640

Asp Glu Ser Lys Leu Ala Ser Thr Lys Leu Ser Ile Gly Ala Glu Asn
                645                 650                 655

Ala Glu His Val Glu Val Thr Lys Ser Gly Ile Ala Leu Lys Ala Asp
                660                 665                 670

Asn Thr Ser Asp Lys Ser Ser Ile Thr Leu Ala Gln Asp Ala Ile Thr
                675                 680                 685

Leu Ala Gly Asn Ala Thr Gly Thr Ala Ile Lys Leu Thr Gly Val Ala
                690                 695                 700

Asp Gly Asn Ile Thr Val Asn Ser Lys Asp Ala Val Asn Gly Gly Gln
705                 710                 715                 720

Leu Arg Thr Leu Leu Gly Val Asp Ser Gly Ala Lys Ile Gly Gly Thr
                725                 730                 735

Glu Lys Thr Thr Ile Ser Glu Ala Ile Ser Asp Val Lys Gln Ala Leu
                740                 745                 750

Thr Asp Ala Thr Leu Ala Tyr Lys Ala Asp Asn Lys Asn Gly Lys Thr
                755                 760                 765

Val Lys Leu Thr Asp Gly Leu Asn Phe Thr Ser Thr Thr Asn Ile Asp
                770                 775                 780

Ala Ser Val Glu Asp Asn Gly Val Val Lys Phe Thr Leu Lys Asp Lys
785                 790                 795                 800
```

```
Leu Thr Gly Leu Lys Thr Ile Ala Thr Glu Ser Leu Asn Ala Ser Gln
            805                 810                 815

Asn Ile Ile Ala Gly Gly Thr Val Thr Val Gly Gly Glu Thr Glu Gly
        820                 825                 830

Ile Val Leu Thr Lys Ser Gly Ser Gly Asn Asp Arg Thr Leu Ser Leu
            835                 840                 845

Ser Gly Ala Gly Asn Ala Ala Thr Asp Gly Ile Lys Val Ser Gly Val
    850                 855                 860

Lys Ala Gly Thr Ala Asp Thr Asp Ala Val Asn Lys Gly Gln Leu Asp
865                 870                 875                 880

Lys Leu Phe Lys Ala Ile Asn Asp Ala Leu Gly Thr Thr Asp Leu Ala
            885                 890                 895

Val Thr Lys Asn Pro Asn Gln Thr Ser Ile Phe Asn Pro Ile Asn Gly
            900                 905                 910

Thr Ala Pro Thr Thr Phe Lys Asp Ala Val Asp Lys Leu Thr Thr Ala
            915                 920                 925

Val Asn Thr Gly Trp Gly Ser Lys Val Gly Ile Leu Ala Thr Gly Ile
    930                 935                 940

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: A 5'primer for the amplification of the DNA
      fragment from Avibacterium paragallinarum type A

<400> SEQUENCE: 14
catgccatgg atggcacaat tacatttaca                                    30

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: A 3'primer for the amplification of the DNA
      fragment from Avibacterium paragallinarum type A

<400> SEQUENCE: 15
cgcggatcca ccttgagtgc tagatgctgt aggtgc                             36

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: A 5'primer for the amplification of the DNA
      fragment from Avibacterium paragallinarum type C

<400> SEQUENCE: 16
cgcggatccg gctcacagct ttatgcaacg aactttatg                          39

<210> SEQ ID NO 17
<211> LENGTH: 39
<212> TYPE: DNA
<213> ORGANISM: Artificial Sequence
```

```
<220> FEATURE:
<223> OTHER INFORMATION: Description of Artificial Sequence: Synthetic
      primer
<220> FEATURE:
<223> OTHER INFORMATION: A 3'primer for the amplification of the DNA
      fragment from Avibacterium paragallinarum type C

<400> SEQUENCE: 17
cgcggatccc taaccttgag tgctagatgc tgtaggtgc                              39

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: A 5'primer for the amplification of the DNA
      fragment from Avibacterium paragallinarum type C

<400> SEQUENCE: 18
agacgcggat ccgatggcac aattacattt aca                                    33

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: A 5'primer for the amplification of the DNA
      fragment from Avibacterium paragallinarum type C

<400> SEQUENCE: 19
cgcggatccg gcttaatgaa agacattgaa                                        30

<210> SEQ ID NO 20
<211> LENGTH: 42
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: A 3'primer for the amplification of the DNA
      fragment from Avibacterium paragallinarum type C

<400> SEQUENCE: 20
cgcggatccc taaataccctg ttgccaaaat acctaccttt ga                         42

<210> SEQ ID NO 21
<211> LENGTH: 38
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: A 5'primer for the amplification of the DNA
      fragment from Avibacterium paragallinarum type C

<400> SEQUENCE: 21
gctctagagg ctcacagctt tatgcaacga actttatg                               38

<210> SEQ ID NO 22
<211> LENGTH: 35
<212> TYPE: DNA
<213> ORGANISM: Artificial Sequence
```

<220> FEATURE:
<223> OTHER INFORMATION: Description of Artificial Sequence: Synthetic
      primer
<220> FEATURE:
<223> OTHER INFORMATION: A 5'primer for the amplification of the DNA
      fragment from Avibacterium paragallinarum type C

<400> SEQUENCE: 22
gctctagaga tggcacaatt acatttacaa atatt                              35

<210> SEQ ID NO 23
<211> LENGTH: 38
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: A 5'primer for the amplification of the DNA
      fragment from Avibacterium paragallinarum type C

<400> SEQUENCE: 23
gctctagagg cttaatgaaa gacattgaag gggtaaac                           38

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DNA sequence which encodes the linker
      consisting of glycine

<400> SEQUENCE: 24
ggcggaggtg gcggaggtgg cggaggtggc                                    30

<210> SEQ ID NO 25
<211> LENGTH: 2042
<212> TYPE: PRT
<213> ORGANISM: Avibacterium paragallinarum
<220> FEATURE:
<223> OTHER INFORMATION: type A

<400> SEQUENCE: 25

Met Asn Lys Val Phe Lys Ile Lys Tyr Ser Val Val Lys Gln Glu Met
1               5                   10                  15

Ile Val Val Ser Glu Leu Ala Asn Asn Lys Asp Lys Thr Ala Ser Gln
            20                  25                  30

Lys Asn Thr His Asn Thr Ala Phe Phe Gln Pro Leu Phe Thr Lys Cys
        35                  40                  45

Thr Tyr Leu Ala Leu Leu Ile Asn Ile Ala Leu Gly Ala Ser Leu Phe
    50                  55                  60

Pro Gln Leu Ala Asn Ala Lys Trp Leu Glu Val Tyr Ser Ser Ser Val
65                  70                  75                  80

Lys Leu Ser Thr Val Ser Ala Gln Ser Asn Ser Val Asn Leu Asn Pro
                85                  90                  95

Ser Gly Ala Glu Ser Val Gly Thr Asn Ser Pro Gln Gly Val Ala Ile
            100                 105                 110

Gly Tyr Gly Ala Thr Asn Asp Arg Ser Ala Thr Gly Ala Ile Ala Leu
        115                 120                 125

Gly Val Gly Val Lys Asn Glu Thr Leu Ala Lys Asp Ser Ile Ala Ile
    130                 135                 140

```
Gly Tyr Gly Ala Lys Asn Glu Ser Thr Ala Pro Ser Ser Val Thr Ile
145                 150                 155                 160

Gly Lys Gln Ala Ile Asn Arg Phe Glu Lys Ser Ile Val Met Gly Leu
                165                 170                 175

Asn Ala Tyr Thr Gln Leu Asp Pro Arg Gly Thr Ser Lys Glu Thr Arg
            180                 185                 190

Gln Gly Ser Val Val Ile Gly Glu Asn Ala Lys Ser Ala Gly Asn Gln
        195                 200                 205

Ser Val Ser Leu Gly Gln Asn Ser Trp Ser Lys Thr Asn Ser Ile Ser
    210                 215                 220

Ile Gly Ala Gly Thr Phe Ala Glu Gly Lys Ser Ser Ile Ala Ile Gly
225                 230                 235                 240

Thr Asp Lys Ile Ser Gly Thr Lys Tyr Asn Asp Lys Leu Pro Ala Thr
                245                 250                 255

Ala Trp Asn Gly Thr Gly Thr Val Pro Lys Asn Ser Ile Trp Asp Ile
            260                 265                 270

Phe Ser Glu Leu Tyr Met Gly Lys Gln Thr Asn Gly Arg Asp Tyr Asp
        275                 280                 285

Thr Thr Thr Arg Asp Pro Asn Lys Pro Glu Ala Phe Tyr Lys Phe Ser
290                 295                 300

Asp Phe Lys Gly Lys Tyr Val Asn Thr Pro Thr Ala Ser Pro Thr Tyr
305                 310                 315                 320

Ala Gly Lys Leu Gly Ala Ile Ala Leu Gly Ser Arg Thr Ile Ala Ala
                325                 330                 335

Gly Glu Met Ser Thr Ala Val Gly Ser Leu Ala Phe Ala Leu Ala Asp
            340                 345                 350

Arg Ser Thr Ala Met Gly Leu Arg Ser Phe Val Ala Lys Asp Ala Val
        355                 360                 365

Gly Gly Thr Ala Ile Gly Glu Glu Ser Arg Thr Phe Ala Lys Asp Ser
    370                 375                 380

Val Ala Ile Gly Asn Lys Thr Glu Ala Ser Asn Ala Gly Ser Met Ala
385                 390                 395                 400

Tyr Gly Tyr Lys Ala Lys Ala Val Gly Ala Gly Ala Ile Ala Ile Gly
                405                 410                 415

Thr Glu Val Ala Ala Gly Ala Lys Phe Asn Ser His Gln Thr Gly Asn
            420                 425                 430

Leu Leu Gln Asp Asn Asn Ala Tyr Ala Thr Leu Lys Asn Ala Asp Lys
        435                 440                 445

Ser Asp Asp Thr Lys Thr Gly Asn Ala Ile Thr Val Phe Thr Gln Ser
    450                 455                 460

Phe Asp Asn Met Leu Thr Asn Gly Leu Pro Leu Val Ser Glu Asn Glu
465                 470                 475                 480

Thr Tyr Leu Thr Thr Ser Ala Gly Ala Ile Lys Lys Thr Ala Thr Thr
                485                 490                 495

Asp Ser Ser Ala Gly Gly Lys Asn Ala Ile Ala Ile Gly Ser Lys
            500                 505                 510

Thr Phe Ala Ser Lys Ala Asn Ser Val Ala Leu Gly Ser Tyr Ala Leu
        515                 520                 525

Ala Asp Ala Gln Asn Ala Phe Ala Leu Gly Ser Tyr Ser Phe Val Glu
    530                 535                 540

Ser Ser Ala Thr Asn Thr Ile Thr Ile Gly Val Gly Ser Tyr Ala Lys
545                 550                 555                 560

Gly Lys Asn Ser Phe Leu Gly Gly Thr Trp Ala Ser Thr Leu Ser Asp
                565                 570                 575
```

```
Arg Thr Val Val Leu Gly Asn Ser Thr Ser Ile Ser Ser Gly Ser Gln
            580                 585                 590

Asn Ala Leu Ala Ile Gly Val Asn Val Phe Ile Gly Asn Asp Ser Ala
        595                 600                 605

Ser Ser Leu Ala Leu Gly Met Gly Ser Thr Ile Ala Lys Ser Ala Lys
    610                 615                 620

Ser Pro Asp Ser Leu Ala Ile Gly Lys Glu Ala Arg Ile Asp Ala Lys
625                 630                 635                 640

Asp Thr Asp Asn Gly Thr Leu Tyr Gln Pro Gln Val Tyr Asp Glu Thr
            645                 650                 655

Thr Arg Ala Phe Arg Asn Phe Asn Glu Ser Ser Asp Tyr Met Arg Gln
                660                 665                 670

Ala Met Ala Leu Gly Phe Asn Ala Lys Val Ser Arg Gly Val Gly Lys
            675                 680                 685

Met Glu Thr Gly Ile Asn Ser Met Ala Ile Gly Ala Tyr Ala Gln Ala
        690                 695                 700

Thr Leu Gln Asn Ser Thr Ala Leu Gly Val Gly Ser Lys Thr Asp Tyr
705                 710                 715                 720

Thr Trp Glu Gln Leu Glu Thr Asp Pro Trp Val Ser Glu Gly Ala Ile
                725                 730                 735

Ser Ile Pro Thr Ser Gly Lys Thr Gly Val Ile Ser Val Gly Ser Lys
            740                 745                 750

Gly Ser Glu Arg Arg Ile Val Asn Leu Ala Ser Gly Ser Ser Asp Thr
        755                 760                 765

Asp Ala Val Asn Val Ala Gln Leu Lys Thr Val Glu Glu Arg Phe Leu
770                 775                 780

Ser Glu Ile Asn Leu Leu Gln Asn Gly Gly Val Lys Tyr Leu Ser
785                 790                 795                 800

Val Glu Lys Thr Asn Ile Asn Gly Gln Ser Gly Arg Val Ala Ser Gln
                805                 810                 815

Ile Arg Lys Gly Glu Asn Tyr Glu Arg Tyr Val Lys Leu Lys Thr Gln
            820                 825                 830

Leu Leu Tyr Leu Asp Ala Arg Gly Lys Leu Asn Gly Glu Lys Phe Asp
        835                 840                 845

Gln Asn Ser Leu Asn Lys Ile Arg Ala Val Val Gln Glu Leu Glu Ala
850                 855                 860

Glu Tyr Ser Gly Glu Leu Lys Thr Thr Ala Ser Ala Leu Asn Gln Val
865                 870                 875                 880

Ala Thr Gln Leu Glu Gln Glu Val Thr Thr Asn Asn Phe Asp Lys Phe
                885                 890                 895

Asn Gln Tyr Lys Thr Gln Ile Glu Asn Ala Ser Asn Ala Asp Ser Ala
            900                 905                 910

Arg Asn Val Gly Gly Leu Thr Pro Gln Ala Ile Ala Gln Leu Lys Ala
        915                 920                 925

Asn Asn Asn Tyr Leu Asn Asp Gly Ala Lys Gly Gln Asp Ser Ile Ala
930                 935                 940

Phe Gly Trp Gln Ala Lys Thr Ser Gly Ala Asn Asn Gly Leu Ala Gly
945                 950                 955                 960

Lys Gln Ala Ile Ala Ile Gly Phe Gln Ala Asn Ser Ser Ala Glu Asn
                965                 970                 975

Ala Ile Ser Ile Gly Thr Asn Ser Asp Thr Ser Met Thr Gly Ala Val
            980                 985                 990

Ala Ile Gly Lys Gly Ala Thr Val  Thr Ala Gly Gly Lys  Pro Ser Ile
```

-continued

```
              995                 1000                1005
Ala  Leu  Gly  Gln  Asp  Ser  Thr  Val  Ala  Asn  Ser  Ala  Ile  Ser  Arg
         1010                1015                1020

Thr  Ser  Ser  Pro  Met  Ile  Asn  Gly  Leu  Ile  Phe  Asn  Asn  Phe  Ala
         1025                1030                1035

Gly  Ser  Pro  Glu  Thr  Leu  Gly  Val  Leu  Ser  Ile  Gly  Thr  Ala  Gly
         1040                1045                1050

Arg  Glu  Arg  Lys  Ile  Val  Asn  Val  Ala  Ala  Gly  Asp  Val  Ser  Gln
         1055                1060                1065

Ala  Ser  Thr  Glu  Ala  Ile  Asn  Gly  Ser  Gln  Leu  Tyr  Ala  Thr  Asn
         1070                1075                1080

Phe  Met  Leu  Ser  Lys  Val  Ala  Gln  Ser  Val  Lys  Ser  Asn  Phe  Gly
         1085                1090                1095

Gly  Asn  Val  Asn  Leu  Gly  Thr  Asp  Gly  Thr  Ile  Thr  Phe  Thr  Asn
         1100                1105                1110

Ile  Gly  Gly  Thr  Gly  Gln  Ala  Thr  Ile  His  Asp  Ala  Ile  Asn  Asn
         1115                1120                1125

Val  Leu  Thr  Lys  Gly  Ile  Tyr  Leu  Lys  Ala  Asp  Gln  Asn  Asp  Pro
         1130                1135                1140

Thr  Gly  Asn  Gln  Gly  Gln  Lys  Val  Glu  Leu  Gly  Asn  Ala  Ile  Thr
         1145                1150                1155

Leu  Ser  Ala  Thr  Asn  Gln  Trp  Ala  Asn  Asn  Gly  Val  Asn  Tyr  Lys
         1160                1165                1170

Thr  Asn  Asn  Leu  Thr  Thr  Tyr  Asn  Ser  Gln  Asn  Gly  Thr  Ile  Leu
         1175                1180                1185

Phe  Gly  Met  Arg  Glu  Asp  Pro  Ser  Val  Lys  Gln  Ile  Thr  Ala  Gly
         1190                1195                1200

Thr  Tyr  Asn  Thr  Thr  Gly  Asp  Ala  Asn  Asn  Lys  Asn  Gln  Leu  Asn
         1205                1210                1215

Asn  Thr  Leu  Gln  Gln  Thr  Thr  Leu  Glu  Ala  Thr  Gly  Ile  Thr  Ser
         1220                1225                1230

Ser  Val  Gly  Ser  Thr  Asn  Tyr  Ala  Gly  Phe  Ser  Leu  Gly  Ala  Asp
         1235                1240                1245

Ser  Val  Thr  Phe  Ser  Lys  Gly  Gly  Ala  Gly  Thr  Val  Lys  Leu  Ser
         1250                1255                1260

Gly  Val  Ser  Asp  Ala  Thr  Ala  Asp  Thr  Asp  Ala  Ala  Thr  Leu  Lys
         1265                1270                1275

Gln  Val  Lys  Glu  Tyr  Arg  Thr  Leu  Val  Gly  Asp  Asn  Asp  Ile
         1280                1285                1290

Thr  Ala  Ala  Asp  Arg  Ser  Gly  Gly  Thr  Ser  Asn  Gly  Ile  Thr  Tyr
         1295                1300                1305

Asn  Leu  Ser  Leu  Asn  Lys  Gly  Thr  Val  Ser  Ala  Thr  Glu  Glu  Lys
         1310                1315                1320

Val  Val  Ser  Gly  Lys  Thr  Val  Tyr  Glu  Ala  Ile  Arg  Asn  Ala  Ile
         1325                1330                1335

Thr  Gly  Asn  Ile  Phe  Thr  Ile  Gly  Leu  Asp  Asp  Thr  Thr  Leu  Asn
         1340                1345                1350

Lys  Ile  Asn  Asn  Pro  Ala  Asp  Gln  Asp  Leu  Ser  Asn  Leu  Ser  Glu
         1355                1360                1365

Ser  Gly  Lys  Asn  Ala  Ile  Thr  Gly  Leu  Val  Asp  Val  Val  Lys  Lys
         1370                1375                1380

Thr  Asn  Ser  Pro  Ile  Thr  Val  Glu  Pro  Ser  Thr  Asp  Ser  Asn  Lys
         1385                1390                1395
```

```
Lys Lys Thr Phe Thr Val Gly Val Asp Phe Thr Asp Thr Ile Thr
1400                1405                1410

Glu Gly Asp Ala Thr Asp Asp Lys Lys Leu Thr Thr Ser Lys Ser
1415                1420                1425

Val Glu Ser Tyr Val Thr Asn Lys Leu Ala Asn Phe Ser Thr Asp
1430                1435                1440

Ile Leu Leu Ser Asp Gly Arg Ser Gly Asn Ala Thr Thr Ala Asn
1445                1450                1455

Asp Gly Val Gly Lys Arg Arg Leu Ser Asp Gly Phe Thr Ile Lys
1460                1465                1470

Ser Glu Asn Phe Thr Leu Gly Ser Lys Gln Tyr Asn Gly Ser Asp
1475                1480                1485

Ser Leu Gly Val Met Tyr Asp Asp Gln Asn Gly Val Phe Lys Leu
1490                1495                1500

Ser Leu Asn Met Thr Ala Leu Thr Thr Ser Leu Ala Asn Thr Phe
1505                1510                1515

Ala Lys Leu Asp Ala Ser Asn Leu Thr Asp Asp Ser Asn Lys Glu
1520                1525                1530

Lys Trp Arg Thr Ala Leu Asn Val Tyr Ser Lys Thr Glu Val Asp
1535                1540                1545

Ala Glu Ile Gln Lys Ser Lys Val Thr Leu Thr Pro Asp Ser Gly
1550                1555                1560

Leu Ile Phe Ala Thr Lys Gln Ala Gly Ser Gly Asn Asn Ala Gly
1565                1570                1575

Ile Asp Ala Gly Asn Lys Lys Ile Ser Asn Val Ala Asp Gly Asp
1580                1585                1590

Ile Ser Pro Thr Ser Gly Asp Val Val Thr Gly Arg Gln Leu Tyr
1595                1600                1605

Ala Leu Met Gln Lys Gly Ile Arg Val Tyr Gly Asp Glu Val Ser
1610                1615                1620

Pro Thr Lys Thr Gln Thr Thr Ala Pro Thr Asn Ala Asn Pro Thr
1625                1630                1635

Ala Thr Thr Ala Pro Thr Ala Ser Ser Thr Gln Gly Trp Ala Thr
1640                1645                1650

Thr Ala Asn Thr Ala Gly Gly Val Ala Pro Ala Gly Asn Val Ala
1655                1660                1665

Thr Gly Asp Ile Ala Pro Thr Gln Pro Thr Leu Pro Glu Met Asn
1670                1675                1680

Thr Ala Leu Val Asp Asp His Leu Ala Val Pro Leu Gly Gly Ser
1685                1690                1695

Leu Lys Ile His Gly Asp His Asn Val Lys Thr Thr Ile Ser Ala
1700                1705                1710

Asp Asn Gln Val Gly Ile Ser Leu Gln Pro Asn Ile Ser Ile Glu
1715                1720                1725

Asn Asn Leu Val Ile Gly Ser Asn Asp Pro Glu Lys Ala Lys Leu
1730                1735                1740

Ala Ala Gln Glu Gly Asn Ala Leu Val Ile Thr Asn Lys Asp Asp
1745                1750                1755

Gly Asn Ala Ala Met Val Phe Asn Asn Glu Lys Asn Met Leu Val
1760                1765                1770

Leu Ser Asp Lys Glu Ala Lys Pro Arg Val Leu Leu Asp Gly Gln
1775                1780                1785

Asn Gly Ala Leu Thr Leu Val Gly Asn Asp Asp Ser Gln Val Thr
1790                1795                1800
```

```
Leu Ser Ser Lys Lys Gly Lys Asp Ile Asp Gly Asn Asp Leu Ser
    1805            1810                1815

Arg Leu Ser Val Thr Thr Glu Arg Thr Asn Ala Asp Gly Gln Leu
    1820            1825                1830

Glu Lys Val Glu Thr Ser Phe Ala Thr Met Asp Asp Gly Leu Lys
    1835            1840                1845

Phe Lys Ala Asp Gly Asp Lys Val Ile Asn Lys Lys Leu Asn Glu
    1850            1855                1860

Thr Val Glu Ile Val Gly Asp Glu Asn Val Thr Thr Ser Ile Thr
    1865            1870                1875

Asp Asp Asn Lys Val Lys Val Ser Leu Asn Lys Lys Ile Ala Ile
    1880            1885                1890

Asp Glu Val Lys Ile Pro Asn Thr Asp Pro Asp Ala Gln Lys Gly
    1895            1900                1905

Asp Ser Ile Val Ile Asn Asn Gly Gly Ile His Ala Gly Asn Lys
    1910            1915                1920

Val Ile Thr Gly Val Lys Ala Ser Asp Asp Pro Thr Ser Ala Val
    1925            1930                1935

Asn Arg Gly Gln Leu Asn Thr Val Ile Asp Asn Val Gln Asn Asn
    1940            1945                1950

Phe Asn Gln Val Asn Gln Arg Ile Gly Asp Leu Thr Arg Glu Ser
    1955            1960                1965

Arg Ala Gly Ile Ala Gly Ala Met Ala Thr Ala Ser Leu Gln Asn
    1970            1975                1980

Val Ala Leu Pro Gly Lys Thr Thr Ile Ser Val Gly Thr Ala Thr
    1985            1990                1995

Phe Lys Gly Glu Asn Ala Val Ala Ile Gly Met Ser Arg Leu Ser
    2000            2005                2010

Asp Asn Gly Lys Val Gly Ile Arg Leu Ser Gly Met Ser Thr Ser
    2015            2020                2025

Asn Gly Asp Lys Gly Ala Ala Met Ser Val Gly Phe Ser Phe
    2030            2035                2040

<210> SEQ ID NO 26
<211> LENGTH: 2039
<212> TYPE: PRT
<213> ORGANISM: Avibacterium paragallinarum
<220> FEATURE:
<223> OTHER INFORMATION: type C

<400> SEQUENCE: 26

Met Asn Lys Val Phe Lys Ile Lys Tyr Ser Val Val Lys Gln Glu Met
1               5                   10                  15

Ile Val Val Ser Glu Leu Ala Asn Asn Lys Asp Lys Thr Ala Ser Gln
                20                  25                  30

Lys Asn Thr His Asn Thr Ala Phe Phe Gln Pro Leu Thr Lys Cys
            35                  40                  45

Thr Tyr Leu Ala Leu Leu Ile Asn Ile Ala Leu Gly Thr Ser Leu Phe
    50                  55                  60

Pro Gln Leu Ala Asn Ala Lys Phe Leu Glu Val Tyr Asn Ser Ser Val
65              70                  75                  80

Lys Leu Gln His Val Asn Ser Gly Val Pro Ser Asp Ser Val Asn Leu
                85                  90                  95

Asn Pro Ser Gly Gly Glu Asn Val Gly Met Asn Ser Asn Gln Gly Val
            100                 105                 110
```

```
Ala Ile Gly Arg Gly Ala Val Asn Asn Tyr Ser Ala Thr Gly Ser Ile
        115                 120                 125

Ala Ile Gly Gln Gly Ala Lys Asn Asp Asn Trp Ala Thr Arg Ser Ile
    130                 135                 140

Ala Ile Gly Gln Gly Ala Lys Asn Glu Ser Ile Ala Ser Asp Ser Val
145                 150                 155                 160

Ala Ile Ser Asn Ala Ile Asn Arg Phe Lys Lys Ser Ile Val Ile Gly
                165                 170                 175

Leu Asn Thr Tyr Thr Gln Leu Asp Pro Arg Arg Ala Pro Glu Ser Arg
            180                 185                 190

Gln Gly Ser Val Val Ile Gly Glu Asn Ala Lys Ser Ala Gly Asn Gln
        195                 200                 205

Ser Val Ser Leu Gly Gln Asn Ala Trp Ser Lys Thr Asn Ser Ile Ser
    210                 215                 220

Ile Gly Ala Gly Thr Phe Ala Glu Gly Lys Ser Thr Ile Ala Ile Gly
225                 230                 235                 240

Thr Asp Lys Ile Leu Gly Thr Asn Tyr Asn Asp Lys Leu Pro Ala Pro
                245                 250                 255

Ser Trp Asp Gly Arg Thr Gly Lys Ala Pro Thr Asn Ser Ile Trp Asp
            260                 265                 270

Ile Phe Ser Glu Leu Tyr Met Gly Lys Lys Thr Asn Gly Thr Asp Tyr
        275                 280                 285

Asp Ala Lys Lys Asn Asp Arg Asp Pro Asn Lys Pro Glu Ala Phe Tyr
    290                 295                 300

Thr Tyr Ser Asp Phe Lys Ser Arg Tyr Val Asn Asn Pro Ser Thr Ser
305                 310                 315                 320

Pro Thr Tyr Ala Ala Lys Leu Gly Ala Ile Ala Leu Gly Ser Arg Thr
                325                 330                 335

Ile Ala Ala Gly Glu Met Ser Thr Ala Val Gly Ser Leu Ala Phe Ala
            340                 345                 350

Leu Ala Asp Lys Ser Thr Ala Met Gly Leu Arg Ser Phe Val Ala Lys
        355                 360                 365

Asp Ala Val Gly Gly Thr Ala Ile Gly Glu Glu Ser Arg Thr Phe Ala
    370                 375                 380

Lys Asp Ser Val Ala Ile Gly Asn Lys Thr Glu Ala Ser Asn Ala Gly
385                 390                 395                 400

Ser Met Ala Tyr Gly Tyr Lys Ala Lys Ala Val Gly Ala Gly Ala Ile
                405                 410                 415

Ala Ile Gly Ala Glu Val Ala Ala Gly Ala Glu Phe Asp Ser Ser Gln
            420                 425                 430

Ala Gly Asn Leu Leu Leu Asn Arg Gly Ala Tyr Ala Thr Leu Lys Ser
        435                 440                 445

Ala Asp Lys Ser Asp Asp Ile Lys Ala Gly Asp Ala Ile Asn Val Phe
    450                 455                 460

Thr Gln Phe Phe Asp Asn Met Leu Thr Gln Gly Ser His Leu Thr Tyr
465                 470                 475                 480

Glu Asn Thr Thr Tyr Leu Thr Thr Ser Ala Gly Asp Ile Lys Lys Thr
                485                 490                 495

Leu Ala Ala Val Gly Asp Gly Gly Lys Asn Ala Ile Ala Ile Gly Asn
            500                 505                 510

Lys Thr Phe Ala Ser Lys Ala Asn Ser Val Ala Leu Gly Ser Tyr Ala
        515                 520                 525

Leu Ala Ser Ala Gln Asn Ala Phe Ala Leu Gly Ser Tyr Ser Leu Val
    530                 535                 540
```

-continued

Ser Pro Leu Ala Ala Asn Thr Ile Val Ile Gly Val Gly Gly Tyr Ala
545                 550                 555                 560

Thr Gly Ser Asn Ser Phe Val Gly Gly Ser Trp Val Ser Thr Leu Ser
            565                 570                 575

Ala Arg Thr Val Val Leu Gly Tyr Ser Ala Ser Ile Ser Ser Asp Ser
        580                 585                 590

His Asp Ser Leu Ala Met Gly Val Asn Ala Phe Ile Gly Asn Gly Ser
    595                 600                 605

Asn Ser Ser Leu Ala Leu Gly Thr Gly Ser Thr Ile Ala Lys Asn Ala
        610                 615                 620

Lys Ser Pro Asp Ser Leu Ala Ile Gly Lys Asp Ser Arg Ile Asp Ala
625                 630                 635                 640

Lys Asp Thr Asp Asn Gly Val Leu Tyr Thr Pro Gln Val Tyr Asp Glu
                645                 650                 655

Thr Thr Arg Ala Phe Arg Thr Phe Asp Glu Asn Lys Asp Tyr Met Arg
            660                 665                 670

Gln Ala Met Ala Leu Gly Phe Asn Ala Lys Val Ser Arg Gly Lys Gly
        675                 680                 685

Lys Met Glu Thr Gly Ile Asn Ser Met Ala Ile Gly Ala Arg Ser Gln
690                 695                 700

Ala Thr Leu Gln Asn Ser Thr Ala Leu Gly Val Asn Ala Lys Thr Asp
705                 710                 715                 720

Tyr Thr Trp Glu Gln Leu Glu Ala Asp Pro Trp Val Ser Lys Gly Ala
                725                 730                 735

Ile Ser Ile Pro Thr Ser Gly Lys Ile Gly Val Ile Ser Val Gly Ser
            740                 745                 750

Lys Gly Ser Glu Arg Arg Ile Val Asn Val Ala Ser Gly Ser Leu Asp
        755                 760                 765

Thr Asp Ala Val Asn Val Ala Gln Leu Lys Thr Ile Glu Glu Arg Phe
770                 775                 780

Gln Ser Glu Ile Asp Leu Leu Gln Asn Gly Gly Val Gln Tyr Leu
785                 790                 795                 800

Ser Val Glu Lys Thr Asn Ile Asn Gly Glu Ala Gly Arg Val Ala Ser
                805                 810                 815

Gln Ile Arg Lys Gly Glu Ser Tyr Lys Arg Tyr Val Lys Leu Lys Thr
            820                 825                 830

Gln Leu Leu Tyr Leu Asp Ala Arg Lys Lys Leu Asn Gly Glu Lys Phe
        835                 840                 845

Asp Gln Thr Ser Leu Asp Lys Ile Ser Lys Ala Val Gln Glu Leu Glu
850                 855                 860

Ala Glu Tyr Ser Gly Glu Leu Lys Thr Thr Ala Ser Glu Leu Asn Arg
865                 870                 875                 880

Val Ala Met Gln Leu Asn Ala Glu Thr Thr Val Asn Asp Phe Gly Lys
                885                 890                 895

Phe Asn Gln Tyr Lys Thr Gln Ile Glu Asn Ala Thr Asn Ala Asp Ser
            900                 905                 910

Glu Lys Asn Val Gly Gly Leu Ser Pro Gln Val Ile Ala Gln Leu Lys
        915                 920                 925

Ala Asn Asn Asn Tyr Leu Asn Asp Gly Ala Lys Gly Gln Asp Ser Ile
930                 935                 940

Ala Phe Gly Trp Gln Ala Lys Thr Ser Glu Ala Asn Asn Gly Leu Ala
945                 950                 955                 960

Gly Lys Gln Ala Ile Ala Ile Gly Phe Gln Ala Asn Ser Ser Ala Glu

-continued

```
                965                 970                 975
Asn Ala Ile Ser Ile Gly Thr Asn Ser Asp Thr Ser Met Thr Gly Ala
                    980                 985                 990
Val Ala Ile Gly Lys Gly Ala Thr Val Thr Ala Gly Gly Lys Pro Ser
                    995                1000                1005
Ile Ala Leu Gly Gln Asp Ser Thr Val Ala Asn Ser Ala Ile Ser
    1010                1015                1020
Arg Thr Ser Ser Val Met Ile Asn Gly Leu Thr Phe Asn Asn Phe
    1025                1030                1035
Ala Gly Ser Pro Glu Thr Leu Gly Val Leu Ser Ile Gly Thr Ala
    1040                1045                1050
Gly Lys Glu Arg Lys Ile Val Asn Val Ala Ala Gly Asp Ile Ser
    1055                1060                1065
Gln Thr Ser Thr Glu Ala Ile Asn Gly Ser Gln Leu Tyr Ala Thr
    1070                1075                1080
Asn Phe Met Leu Asn Lys Leu Ala Gln Ser Val Lys Thr Asn Phe
    1085                1090                1095
Gly Gly Asn Ala Asn Leu Ala Thr Asp Gly Thr Ile Thr Phe Thr
    1100                1105                1110
Asn Ile Gly Gly Thr Gly Gln Asp Thr Ile His Asp Ala Ile Asn
    1115                1120                1125
Asn Val Leu Thr Lys Leu Ile Ser Leu Ser Ala Thr Glu Glu Glu
    1130                1135                1140
Glu Val Val Ser Gly Glu Ala Val Tyr Asp Ala Leu Lys Gly Ala
    1145                1150                1155
Lys Pro Thr Val Ser Ala Glu Ala Asn Lys Gly Ile Thr Gly Leu
    1160                1165                1170
Val Asp Val Val Lys Lys Ala Asn Ser Pro Ile Thr Val Glu Pro
    1175                1180                1185
Ser Thr Asp Asn Asn Lys Lys Lys Thr Phe Thr Val Gly Leu Met
    1190                1195                1200
Lys Asp Ile Glu Gly Val Asn Ser Ile Thr Phe Asp Lys Ser Gly
    1205                1210                1215
Gln Asp Leu Asn Gln Val Thr Gly Arg Met Ser Ser Ala Gly Leu
    1220                1225                1230
Thr Phe Lys Lys Gly Asp Thr Thr Asn Gly Ser Thr Thr Thr Phe
    1235                1240                1245
Ala Glu Asp Gly Leu Thr Ile Asp Ser Thr Thr Asn Ser Ala Gln
    1250                1255                1260
Thr Asn Leu Val Lys Val Ser Arg Asp Gly Phe Ser Val Lys Asn
    1265                1270                1275
Gly Ser Asp Glu Ser Lys Leu Ala Ser Thr Lys Leu Ser Ile Gly
    1280                1285                1290
Ala Glu Asn Ala Glu His Val Glu Val Thr Lys Ser Gly Ile Ala
    1295                1300                1305
Leu Lys Ala Asp Asn Thr Ser Asp Lys Ser Ser Ile Thr Leu Ala
    1310                1315                1320
Gln Asp Ala Ile Thr Leu Ala Gly Asn Ala Thr Gly Thr Ala Ile
    1325                1330                1335
Lys Leu Thr Gly Val Ala Asp Gly Asn Ile Thr Val Asn Ser Lys
    1340                1345                1350
Asp Ala Val Asn Gly Gly Gln Leu Arg Thr Leu Leu Gly Val Asp
    1355                1360                1365
```

-continued

```
Ser Gly Ala Lys Ile Gly Gly Thr Glu Lys Thr Thr Ile Ser Glu
    1370                1375                1380

Ala Ile Ser Asp Val Lys Gln Ala Leu Thr Asp Ala Thr Leu Ala
    1385                1390                1395

Tyr Lys Ala Asp Asn Lys Asn Gly Lys Thr Val Lys Leu Thr Asp
    1400                1405                1410

Gly Leu Asn Phe Thr Ser Thr Asn Ile Asp Ala Ser Val Glu
    1415                1420                1425

Asp Asn Gly Val Val Lys Phe Thr Leu Lys Asp Lys Leu Thr Gly
    1430                1435                1440

Leu Lys Thr Ile Ala Thr Glu Ser Leu Asn Ala Ser Gln Asn Ile
    1445                1450                1455

Ile Ala Gly Gly Thr Val Thr Val Gly Gly Glu Thr Glu Gly Ile
    1460                1465                1470

Val Leu Thr Lys Ser Gly Ser Gly Asn Asp Arg Thr Leu Ser Leu
    1475                1480                1485

Ser Gly Ala Gly Asn Ala Ala Thr Asp Gly Ile Lys Val Ser Gly
    1490                1495                1500

Val Lys Ala Gly Thr Ala Asp Thr Asp Ala Val Asn Lys Gly Gln
    1505                1510                1515

Leu Asp Lys Leu Phe Lys Ala Ile Asn Asp Ala Leu Gly Thr Thr
    1520                1525                1530

Asp Leu Ala Val Thr Lys Asn Pro Asn Gln Thr Ser Ile Phe Asn
    1535                1540                1545

Pro Ile Asn Gly Thr Ala Pro Thr Thr Phe Lys Asp Ala Val Asp
    1550                1555                1560

Lys Leu Thr Thr Ala Val Asn Thr Gly Trp Gly Ser Lys Val Gly
    1565                1570                1575

Ile Leu Ala Thr Gly Ile Asp Gly Ile Asp Ala Gly Asn Lys Lys
    1580                1585                1590

Ile Ser Asn Val Ala Asp Gly Asp Ile Ser Pro Thr Ser Gly Asp
    1595                1600                1605

Val Val Thr Gly Arg Gln Leu Tyr Ala Leu Met Gln Lys Gly Ile
    1610                1615                1620

Arg Val Tyr Gly Asp Glu Val Ser Pro Thr Lys Thr Gln Thr Thr
    1625                1630                1635

Ala Pro Thr Ala Ser Ser Thr Gln Gly Gly Ala Thr Thr Ala Asn
    1640                1645                1650

Thr Ala Gly Gly Val Ala Pro Ala Gly Asn Val Ala Thr Gly Asp
    1655                1660                1665

Ile Ala Pro Thr Gln Pro Ala Leu Pro Glu Met Lys Thr Ala Leu
    1670                1675                1680

Val Gly Asp His Leu Ala Val Pro Leu Gly Gly Ser Leu Lys Ile
    1685                1690                1695

His Gly Asp His Asn Val Lys Thr Thr Ile Ser Ala Gly Asn Gln
    1700                1705                1710

Val Gly Ile Ser Leu Gln Pro Asn Ile Ser Ile Glu Asn Asn Leu
    1715                1720                1725

Val Ile Gly Ser Asn Lys Pro Glu Lys Ala Lys Leu Ala Ala Gln
    1730                1735                1740

Glu Gly Asn Ala Leu Val Ile Thr Asn Lys Asp Asp Gly Asn Ala
    1745                1750                1755

Ala Met Val Phe Asn Asn Glu Lys Asn Met Leu Val Leu Ser Asp
    1760                1765                1770
```

Lys Lys Ala Lys Pro Arg Ala Val Leu Asp Gly Gln Asn Gly Ala
    1775            1780            1785

Leu Thr Leu Val Gly Asn Asp Ser Gln Val Thr Leu Ser Ser
    1790            1795            1800

Lys Lys Gly Lys Asp Ile Asp Gly Asn Asp Leu Ser Arg Leu Ser
    1805            1810            1815

Val Thr Thr Glu Arg Thr Asn Ala Asp Gly Gln Leu Glu Lys Val
    1820            1825            1830

Glu Thr Ser Phe Ala Thr Met Asp Asp Gly Leu Lys Phe Lys Ala
    1835            1840            1845

Asp Gly Asp Lys Val Ile Asn Lys Lys Leu Asn Glu Thr Val Glu
    1850            1855            1860

Ile Val Gly Asp Glu Asn Val Thr Thr Ser Ile Thr Asp Asp Asn
    1865            1870            1875

Lys Val Lys Val Ser Leu Asn Lys Lys Ile Ala Ile Asp Glu Val
    1880            1885            1890

Lys Ile Pro Asn Thr Asp Pro Asp Ala Gln Lys Gly Asp Ser Ile
    1895            1900            1905

Val Ile Asn Asn Gly Gly Ile His Ala Gly Asn Lys Val Ile Thr
    1910            1915            1920

Gly Val Lys Ala Ser Asp Asp Pro Thr Ser Ala Val Asn Arg Gly
    1925            1930            1935

Gln Leu Asn Thr Val Ile Asp Asn Val Gln Asn Asn Phe Asn Gln
    1940            1945            1950

Val Asn Gln Arg Ile Gly Asp Leu Thr Arg Glu Ser Arg Ala Gly
    1955            1960            1965

Ile Ala Gly Ala Met Ala Thr Ala Ser Leu Gln Asn Val Ala Leu
    1970            1975            1980

Pro Gly Lys Thr Thr Ile Ser Val Gly Thr Ala Thr Phe Lys Gly
    1985            1990            1995

Glu Asn Ala Val Ala Ile Gly Met Ser Arg Leu Ser Asp Asn Gly
    2000            2005            2010

Lys Val Gly Ile Arg Leu Ser Gly Met Ser Thr Ser Asn Gly Asp
    2015            2020            2025

Lys Gly Ala Ala Met Ser Val Gly Phe Thr Phe
    2030            2035

<210> SEQ ID NO 27
<211> LENGTH: 484
<212> TYPE: PRT
<213> ORGANISM: Avibacterium paragallinarum
<220> FEATURE:
<223> OTHER INFORMATION: type A

<400> SEQUENCE: 27

Met Asp Gly Thr Ile Thr Phe Thr Asn Ile Gly Gly Thr Gly Gln Ala
1 5 10 15

Thr Ile His Asp Ala Ile Asn Asn Val Leu Thr Lys Gly Ile Tyr Leu
20 25 30

Lys Ala Asp Gln Asn Asp Pro Thr Gly Asn Gln Gly Gln Lys Val Glu
35 40 45

Leu Gly Asn Ala Ile Thr Leu Ser Ala Thr Asn Gln Trp Ala Asn Asn
50 55 60

Gly Val Asn Tyr Lys Thr Asn Asn Leu Thr Thr Tyr Asn Ser Gln Asn
65 70 75 80

Gly Thr Ile Leu Phe Gly Met Arg Glu Asp Pro Ser Val Lys Gln Ile
                 85                  90                  95

Thr Ala Gly Thr Tyr Asn Thr Thr Gly Asp Ala Asn Asn Lys Asn Gln
            100                 105                 110

Leu Asn Asn Thr Leu Gln Gln Thr Thr Leu Glu Ala Thr Gly Ile Thr
        115                 120                 125

Ser Ser Val Gly Ser Thr Asn Tyr Ala Gly Phe Ser Leu Gly Ala Asp
    130                 135                 140

Ser Val Thr Phe Ser Lys Gly Ala Gly Thr Val Lys Leu Ser Gly
145                 150                 155                 160

Val Ser Asp Ala Thr Ala Asp Thr Asp Ala Ala Thr Leu Lys Gln Val
                165                 170                 175

Lys Glu Tyr Arg Thr Thr Leu Val Gly Asp Asn Asp Ile Thr Ala Ala
            180                 185                 190

Asp Arg Ser Gly Gly Thr Ser Asn Gly Ile Thr Tyr Asn Leu Ser Leu
        195                 200                 205

Asn Lys Gly Thr Val Ser Ala Thr Glu Glu Lys Val Val Ser Gly Lys
    210                 215                 220

Thr Val Tyr Glu Ala Ile Arg Asn Ala Ile Thr Gly Asn Ile Phe Thr
225                 230                 235                 240

Ile Gly Leu Asp Asp Thr Thr Leu Asn Lys Ile Asn Asn Pro Ala Asp
                245                 250                 255

Gln Asp Leu Ser Asn Leu Ser Glu Ser Gly Lys Asn Ala Ile Thr Gly
            260                 265                 270

Leu Val Asp Val Val Lys Lys Thr Asn Ser Pro Ile Thr Val Glu Pro
        275                 280                 285

Ser Thr Asp Ser Asn Lys Lys Lys Thr Phe Thr Val Gly Val Asp Phe
    290                 295                 300

Thr Asp Thr Ile Thr Glu Gly Asp Ala Thr Asp Lys Lys Leu Thr
305                 310                 315                 320

Thr Ser Lys Ser Val Glu Ser Tyr Val Thr Asn Lys Leu Ala Asn Phe
                325                 330                 335

Ser Thr Asp Ile Leu Leu Ser Asp Gly Arg Ser Gly Asn Ala Thr Thr
            340                 345                 350

Ala Asn Asp Gly Val Gly Lys Arg Arg Leu Ser Asp Gly Phe Thr Ile
        355                 360                 365

Lys Ser Glu Asn Phe Thr Leu Gly Ser Lys Gln Tyr Asn Gly Ser Asp
    370                 375                 380

Ser Leu Gly Val Met Tyr Asp Asp Gln Asn Gly Val Phe Lys Leu Ser
385                 390                 395                 400

Leu Asn Met Thr Ala Leu Thr Thr Ser Leu Ala Asn Thr Phe Ala Lys
                405                 410                 415

Leu Asp Ala Ser Asn Leu Thr Asp Asp Ser Asn Lys Glu Lys Trp Arg
            420                 425                 430

Thr Ala Leu Asn Val Tyr Ser Lys Thr Glu Val Asp Ala Glu Ile Gln
        435                 440                 445

Lys Ser Lys Val Thr Leu Thr Pro Asp Ser Gly Leu Ile Phe Ala Thr
    450                 455                 460

Lys Gln Ala Gly Ser Gly Asn Asn Ala Gly Ile Asp Ala Gly Asn Lys
465                 470                 475                 480

Lys Ile Ser Asn

<210> SEQ ID NO 28
<211> LENGTH: 406

```
<212> TYPE: PRT
<213> ORGANISM: Avibacterium paragallinarum
<220> FEATURE:
<223> OTHER IN

```
385                 390                 395                 400

Leu Asn Met Thr Ala Leu
                405

<210> SEQ ID NO 29
<211> LENGTH: 267
<212> TYPE: PRT
<213> ORGANISM: Avibacterium paragallinarum
<220> FEATURE:
<223> OTHER INFORMATION: type A

<400> SEQUENCE: 29

Met Asp Gly Thr Ile Thr Phe Thr Asn Ile Gly Gly Thr Gly Gln Ala
1               5                   10                  15

Thr Ile His Asp Ala Ile Asn Asn Val Leu Thr Lys Gly Ile Tyr Leu
            20                  25                  30

Lys Ala Asp Gln Asn Asp Pro Thr Gly Asn Gln Gly Gln Lys Val Glu
        35                  40                  45

Leu Gly Asn Ala Ile Thr Leu Ser Ala Thr Asn Gln Trp Ala Asn Asn
    50                  55                  60

Gly Val Asn Tyr Lys Thr Asn Asn Leu Thr Thr Tyr Asn Ser Gln Asn
65                  70                  75                  80

Gly Thr Ile Leu Phe Gly Met Arg Glu Asp Pro Ser Val Lys Gln Ile
                85                  90                  95

Thr Ala Gly Thr Tyr Asn Thr Thr Gly Asp Ala Asn Asn Lys Asn Gln
            100                 105                 110

Leu Asn Asn Thr Leu Gln Gln Thr Thr Leu Glu Ala Thr Gly Ile Thr
        115                 120                 125

Ser Ser Val Gly Ser Thr Asn Tyr Ala Gly Phe Ser Leu Gly Ala Asp
    130                 135                 140

Ser Val Thr Phe Ser Lys Gly Ala Gly Thr Val Lys Leu Ser Gly
145                 150                 155                 160

Val Ser Asp Ala Thr Ala Asp Thr Ala Ala Thr Leu Lys Gln Val
                165                 170                 175

Lys Glu Tyr Arg Thr Thr Leu Val Gly Asp Asn Asp Ile Thr Ala Ala
            180                 185                 190

Asp Arg Ser Gly Gly Thr Ser Asn Gly Ile Thr Tyr Asn Leu Ser Leu
        195                 200                 205

Asn Lys Gly Thr Val Ser Ala Thr Glu Glu Lys Val Val Ser Gly Lys
    210                 215                 220

Thr Val Tyr Glu Ala Ile Arg Asn Ala Ile Thr Gly Asn Ile Phe Thr
225                 230                 235                 240

Ile Gly Leu Asp Asp Thr Thr Leu Asn Lys Ile Asn Asn Pro Ala Asp
                245                 250                 255

Gln Asp Leu Ser Asn Leu Ser Glu Ser Gly Lys
            260                 265

<210> SEQ ID NO 30
<211> LENGTH: 457
<212> TYPE: PRT
<213> ORGANISM: Avibacterium paragallinarum
<220> FEATURE:
<223> OTHER INFORMATION: type A

<400> SEQUENCE: 30

Met Gly Ile Tyr Leu Lys Ala Asp Gln Asn Asp Pro Thr Gly Asn Gln
1               5                   10                  15

Gly Gln Lys Val Glu Leu Gly Asn Ala Ile Thr Leu Ser Ala Thr Asn
```

-continued

```
                20                  25                  30
Gln Trp Ala Asn Asn Gly Val Asn Tyr Lys Thr Asn Asn Leu Thr Thr
                35                  40                  45
Tyr Asn Ser Gln Asn Gly Thr Ile Leu Phe Gly Met Arg Glu Asp Pro
 50                  55                  60
Ser Val Lys Gln Ile Thr Ala Gly Thr Tyr Asn Thr Thr Gly Asp Ala
 65                  70                  75                  80
Asn Asn Lys Asn Gln Leu Asn Asn Thr Leu Gln Gln Thr Thr Leu Glu
                85                  90                  95
Ala Thr Gly Ile Thr Ser Ser Val Gly Ser Thr Asn Tyr Ala Gly Phe
                100                 105                 110
Ser Leu Gly Ala Asp Ser Val Thr Phe Ser Lys Gly Ala Gly Thr
                115                 120                 125
Val Lys Leu Ser Gly Val Ser Asp Ala Thr Ala Thr Asp Ala Ala
                130                 135                 140
Thr Leu Lys Gln Val Lys Glu Tyr Arg Thr Thr Leu Val Gly Asp Asn
 145                 150                 155                 160
Asp Ile Thr Ala Ala Asp Arg Ser Gly Gly Thr Ser Asn Gly Ile Thr
                165                 170                 175
Tyr Asn Leu Ser Leu Asn Lys Gly Thr Val Ser Ala Thr Glu Glu Lys
                180                 185                 190
Val Val Ser Gly Lys Thr Val Tyr Glu Ala Ile Arg Asn Ala Ile Thr
                195                 200                 205
Gly Asn Ile Phe Thr Ile Gly Leu Asp Asp Thr Thr Leu Asn Lys Ile
                210                 215                 220
Asn Asn Pro Ala Asp Gln Asp Leu Ser Asn Leu Ser Glu Ser Gly Lys
 225                 230                 235                 240
Asn Ala Ile Thr Gly Leu Val Asp Val Val Lys Lys Thr Asn Ser Pro
                245                 250                 255
Ile Thr Val Glu Pro Ser Thr Asp Ser Asn Lys Lys Lys Thr Phe Thr
                260                 265                 270
Val Gly Val Asp Phe Thr Asp Thr Ile Thr Glu Gly Asp Ala Thr Asp
                275                 280                 285
Asp Lys Lys Leu Thr Thr Ser Lys Ser Val Glu Ser Tyr Val Thr Asn
 290                 295                 300
Lys Leu Ala Asn Phe Ser Thr Asp Ile Leu Leu Ser Asp Gly Arg Ser
 305                 310                 315                 320
Gly Asn Ala Thr Thr Ala Asn Asp Gly Val Gly Lys Arg Arg Leu Ser
                325                 330                 335
Asp Gly Phe Thr Ile Lys Ser Glu Asn Phe Thr Leu Gly Ser Lys Gln
                340                 345                 350
Tyr Asn Gly Ser Asp Ser Leu Gly Val Met Tyr Asp Gln Asn Gly
                355                 360                 365
Val Phe Lys Leu Ser Leu Asn Met Thr Ala Leu Thr Thr Ser Leu Ala
                370                 375                 380
Asn Thr Phe Ala Lys Leu Asp Ala Ser Asn Leu Thr Asp Asp Ser Asn
 385                 390                 395                 400
Lys Glu Lys Trp Arg Thr Ala Leu Asn Val Tyr Ser Lys Thr Glu Val
                405                 410                 415
Asp Ala Glu Ile Gln Lys Ser Lys Val Thr Leu Thr Pro Asp Ser Gly
                420                 425                 430
Leu Ile Phe Ala Thr Lys Gln Ala Gly Ser Gly Asn Asn Ala Gly Ile
                435                 440                 445
```

Asp Ala Gly Asn Lys Lys Ile Ser Asn
        450                 455

<210> SEQ ID NO 31
<211> LENGTH: 379
<212> TYPE: PRT
<213> ORGANISM: Avibacterium paragallinarum
<220> FEATURE:
<223> O

```
                355                 360                 365
Val Phe Lys Leu Ser Leu Asn Met Thr Ala Leu
    370                 375

<210> SEQ ID NO 32
<211> LENGTH: 240
<212> TYPE: PRT
<213> ORGANISM: Avibacterium paragallinarum
<220> FEATURE:
<223

```
                50                  55                  60
Ser Asp Ala Thr Ala Asp Thr Asp Ala Ala Thr Leu Lys Gln Val Lys
 65                  70                  75                  80

Glu Tyr Arg Thr Thr Leu Val Gly Asp Asn Asp Ile Thr Ala Ala Asp
                 85                  90                  95

Arg Ser Gly Gly Thr Ser Asn Gly Ile Thr Tyr Asn Leu Ser Leu Asn
                100                 105                 110

Lys Gly Thr Val Ser Ala Thr Glu Glu Lys Val Val Ser Gly Lys Thr
                115                 120                 125

Val Tyr Glu Ala Ile Arg Asn Ala Ile Thr Gly Asn Ile Phe Thr Ile
                130                 135                 140

Gly Leu Asp Asp Thr Thr Leu Asn Lys Ile Asn Asn Pro Ala Asp Gln
145                 150                 155                 160

Asp Leu Ser Asn Leu Ser Glu Ser Gly Lys Asn Ala Ile Thr Gly Leu
                165                 170                 175

Val Asp Val Val Lys Lys Thr Asn Ser Pro Ile Thr Val Glu Pro Ser
                180                 185                 190

Thr Asp Ser Asn Lys Lys Lys Thr Phe Thr Val Gly Val Asp Phe Thr
                195                 200                 205

Asp Thr Ile Thr Glu Gly Asp Ala Thr Asp Lys Lys Leu Thr Thr
                210                 215                 220

Ser Lys Ser Val Glu Ser Tyr Val Thr Asn Lys Leu Ala Asn Phe Ser
225                 230                 235                 240

Thr Asp Ile Leu Leu Ser Asp Gly Arg Ser Gly Asn Ala Thr Thr Ala
                245                 250                 255

Asn Asp Gly Val Gly Lys Arg Arg Leu Ser Asp Gly Phe Thr Ile Lys
                260                 265                 270

Ser Glu Asn Phe Thr Leu Gly Ser Lys Gln Tyr Asn Gly Ser Asp Ser
                275                 280                 285

Leu Gly Val Met Tyr Asp Asp Gln Asn Gly Val Phe Lys Leu Ser Leu
                290                 295                 300

Asn Met Thr Ala Leu Thr Thr Ser Leu Ala Asn Thr Phe Ala Lys Leu
305                 310                 315                 320

Asp Ala Ser Asn Leu Thr Asp Ser Asn Lys Glu Lys Trp Arg Thr
                325                 330                 335

Ala Leu Asn Val Tyr Ser Lys Thr Glu Val Asp Ala Glu Ile Gln Lys
                340                 345                 350

Ser Lys Val Thr Leu Thr Pro Asp Ser Gly Leu Ile Phe Ala Thr Lys
                355                 360                 365

Gln Ala Gly Ser Gly Asn Asn Ala Gly Ile Asp Ala Gly Asn Lys Lys
                370                 375                 380

Ile Ser Asn
385

<210> SEQ ID NO 34
<211> LENGTH: 309
<212> TYPE: PRT
<213> ORGANISM: Avibacterium paragallinarum
<220> FEATURE:
<223> OTHER INFORMATION: type A

<400> SEQUENCE: 34

Met Gly Thr Tyr Asn Thr Thr Gly Asp Ala Asn Asn Lys Asn Gln Leu
 1               5                  10                  15

Asn Asn Thr Leu Gln Gln Thr Thr Leu Glu Ala Thr Gly Ile Thr Ser
                20                  25                  30
```

```
Ser Val Gly Ser Thr Asn Tyr Ala Gly Phe Ser Leu Gly Ala Asp Ser
         35                  40                  45

Val Thr Phe Ser Lys Gly Gly Ala Gly Thr Val Lys Leu Ser Gly Val
 50                  55                  60

Ser Asp Ala Thr Ala Asp Thr Asp Ala Ala Thr Leu Lys Gln Val Lys
 65                  70                  75                  80

Glu Tyr Arg Thr Leu Val Gly Asp Asn Asp Ile Thr Ala Ala Asp
             85                  90                  95

Arg Ser Gly Gly Thr Ser Asn Gly Ile Thr Tyr Asn Leu Ser Leu Asn
             100                 105                 110

Lys Gly Thr Val Ser Ala Thr Glu Glu Lys Val Val Ser Gly Lys Thr
             115                 120                 125

Val Tyr Glu Ala Ile Arg Asn Ala Ile Thr Gly Asn Ile Phe Thr Ile
             130                 135                 140

Gly Leu Asp Asp Thr Thr Leu Asn Lys Ile Asn Asn Pro Ala Asp Gln
145                 150                 155                 160

Asp Leu Ser Asn Leu Ser Glu Ser Gly Lys Asn Ala Ile Thr Gly Leu
                 165                 170                 175

Val Asp Val Val Lys Lys Thr Asn Ser Pro Ile Thr Val Glu Pro Ser
             180                 185                 190

Thr Asp Ser Asn Lys Lys Lys Thr Phe Thr Val Gly Val Asp Phe Thr
             195                 200                 205

Asp Thr Ile Thr Glu Gly Asp Ala Thr Asp Lys Lys Leu Thr Thr
         210                 215                 220

Ser Lys Ser Val Glu Ser Tyr Val Thr Asn Lys Leu Ala Asn Phe Ser
225                 230                 235                 240

Thr Asp Ile Leu Leu Ser Asp Gly Arg Ser Gly Asn Ala Thr Thr Ala
                 245                 250                 255

Asn Asp Gly Val Gly Lys Arg Arg Leu Ser Asp Gly Phe Thr Ile Lys
             260                 265                 270

Ser Glu Asn Phe Thr Leu Gly Ser Lys Gln Tyr Asn Gly Ser Asp Ser
             275                 280                 285

Leu Gly Val Met Tyr Asp Asp Gln Asn Gly Val Phe Lys Leu Ser Leu
             290                 295                 300

Asn Met Thr Ala Leu
305

<210> SEQ ID NO 35
<211> LENGTH: 170
<212> TYPE: PRT
<213> ORGANISM: Avibacterium paragallinarum
<220> FEATURE:
<223> OTHER INFORMATION: type A

```
Glu Tyr Arg Thr Thr Leu Val Gly Asp Asn Asp Ile Thr Ala Ala Asp
                85                  90                  95

Arg Ser Gly Gly Thr Ser Asn Gly Ile Thr Tyr Asn Leu Ser Leu Asn
            100                 105                 110

Lys Gly Thr Val Ser Ala Thr Glu Glu Lys Val Val Ser Gly Lys Thr
        115                 120                 125

Val Tyr Glu Ala Ile Arg Asn Ala Ile Thr Gly Asn Ile Phe Thr Ile
    130                 135                 140

Gly Leu Asp Asp Thr Thr Leu Asn Lys Ile Asn Asn Pro Ala Asp Gln
145                 150                 155                 160

Asp Leu Ser Asn Leu Ser Glu Ser Gly Lys
                165                 170

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: A 5'primer for the amplification of the DNA
      fragment from Avibacterium paragallinarum type A

<400> SEQUENCE: 36
catgccatgg ggatctacct taaag                                        25

<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: A 5'primer for the amplification of the DNA
      fragment from Avibacterium paragallinarum type A

<400> SEQUENCE: 37
catgccatgg gaacctataa tacaacgggt gat                               33

<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: A 3'primer for the amplification of the DNA
      fragment from Avibacterium paragallinarum type A

<400> SEQUENCE: 38
cgcggatcca ttactaattt tcttattccc agc                               33

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: A 3'primer for the amplification of the DNA
      fragment from Avibacterium paragallinarum type A

<400> SEQUENCE: 39
```

```
cgcggatcca agtgcggtca tatttaggct                                          30
```

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: A 3'primer for the amplification of the DNA
      fragment from Avibacterium paragallinarum type A

<400> SEQUENCE: 40

```
cgcggatcct ttgccacttt cactgaggtt                                          30
```

<210> SEQ ID NO 41
<211> LENGTH: 1027
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: A fusion peptide consisting of membrane protein
      sections from each of Avibacterium paragallinarum types A and C

<400> SEQUENCE: 41

```
Met Asp Gly Thr Ile Thr Phe Thr Asn Ile Gly Gly Thr Gly Gln Ala
1               5                   10                  15

Thr Ile His Asp Ala Ile Asn Asn Val Leu Thr Lys Gly Ile Tyr Leu
            20                  25                  30

Lys Ala Asp Gln Asn Asp Pro Thr Gly Asn Gln Gly Gln Lys Val Glu
        35                  40                  45

Leu Gly Asn Ala Ile Thr Leu Ser Ala Thr Asn Gln Trp Ala Asn Asn
    50                  55                  60

Gly Val Asn Tyr Lys Thr Asn Asn Leu Thr Thr Tyr Asn Ser Gln Asn
65                  70                  75                  80

Gly Thr Ile Leu Phe Gly Met Arg Glu Asp Pro Ser Val Lys Gln Ile
                85                  90                  95

Thr Ala Gly Thr Tyr Asn Thr Thr Gly Asp Ala Asn Asn Lys Asn Gln
            100                 105                 110

Leu Asn Asn Thr Leu Gln Gln Thr Leu Glu Ala Thr Gly Ile Thr
        115                 120                 125

Ser Ser Val Gly Ser Thr Asn Tyr Ala Gly Phe Ser Leu Gly Ala Asp
    130                 135                 140

Ser Val Thr Phe Ser Lys Gly Ala Gly Thr Val Lys Leu Ser Gly
145                 150                 155                 160

Val Ser Asp Ala Thr Ala Asp Thr Asp Ala Ala Thr Leu Lys Gln Val
                165                 170                 175

Lys Glu Tyr Arg Thr Thr Leu Val Gly Asp Asn Asp Ile Thr Ala Ala
            180                 185                 190

Asp Arg Ser Gly Gly Thr Ser Asn Gly Ile Thr Tyr Asn Leu Ser Leu
        195                 200                 205

Asn Lys Gly Thr Val Ser Ala Thr Glu Glu Lys Val Val Ser Gly Lys
    210                 215                 220

Thr Val Tyr Glu Ala Ile Arg Asn Ala Ile Thr Gly Asn Ile Phe Thr
225                 230                 235                 240

Ile Gly Leu Asp Asp Thr Thr Leu Asn Lys Ile Asn Asn Pro Ala Asp
                245                 250                 255
```

```
Gln Asp Leu Ser Asn Leu Ser Glu Ser Gly Lys Asn Ala Ile Thr Gly
            260                 265                 270

Leu Val Asp Val Val Lys Lys Thr Asn Ser Pro Ile Thr Val Glu Pro
        275                 280                 285

Ser Thr Asp Ser Asn Lys Lys Lys Thr Phe Thr Val Gly Val Asp Phe
    290                 295                 300

Thr Asp Thr Ile Thr Glu Gly Asp Ala Thr Asp Lys Lys Leu Thr
305                 310                 315                 320

Thr Ser Lys Ser Val Glu Ser Tyr Val Thr Asn Lys Leu Ala Asn Phe
                325                 330                 335

Ser Thr Asp Ile Leu Leu Ser Asp Gly Arg Ser Gly Asn Ala Thr Thr
            340                 345                 350

Ala Asn Asp Gly Val Gly Lys Arg Arg Leu Ser Asp Gly Phe Thr Ile
        355                 360                 365

Lys Ser Glu Asn Phe Thr Leu Gly Ser Lys Gln Tyr Asn Gly Ser Asp
    370                 375                 380

Ser Leu Gly Val Met Tyr Asp Asp Gln Asn Gly Val Phe Lys Leu Ser
385                 390                 395                 400

Leu Asn Met Thr Ala Leu Thr Thr Ser Leu Ala Asn Thr Phe Ala Lys
                405                 410                 415

Leu Asp Ala Ser Asn Leu Thr Asp Asp Ser Asn Lys Glu Lys Trp Arg
            420                 425                 430

Thr Ala Leu Asn Val Tyr Ser Lys Thr Glu Val Asp Ala Glu Ile Gln
        435                 440                 445

Lys Ser Lys Val Thr Leu Thr Pro Asp Ser Gly Leu Ile Phe Ala Thr
    450                 455                 460

Lys Gln Ala Gly Ser Gly Asn Asn Ala Gly Ile Asp Ala Gly Asn Lys
465                 470                 475                 480

Lys Ile Ser Asn Gly Ser Asp Gly Thr Ile Thr Phe Thr Asn Ile Gly
                485                 490                 495

Gly Thr Gly Gln Asp Thr Ile His Asp Ala Ile Asn Asn Val Leu Thr
            500                 505                 510

Lys Leu Ile Ser Leu Ser Ala Thr Glu Glu Glu Val Val Ser Gly
        515                 520                 525

Glu Ala Val Tyr Asp Ala Leu Lys Gly Ala Lys Pro Thr Val Ser Ala
    530                 535                 540

Glu Ala Asn Lys Gly Ile Thr Gly Leu Val Asp Val Lys Lys Ala
545                 550                 555                 560

Asn Ser Pro Ile Thr Val Glu Pro Ser Thr Asp Asn Lys Lys Lys
                565                 570                 575

Thr Phe Thr Val Gly Leu Met Lys Asp Ile Glu Gly Val Asn Ser Ile
            580                 585                 590

Thr Phe Asp Lys Ser Gly Gln Asp Leu Asn Gln Val Thr Gly Arg Met
        595                 600                 605

Ser Ser Ala Gly Leu Thr Phe Lys Lys Gly Asp Thr Thr Asn Gly Ser
    610                 615                 620

Thr Thr Thr Phe Ala Glu Asp Gly Leu Thr Ile Asp Ser Thr Thr Asn
625                 630                 635                 640

Ser Ala Gln Thr Asn Leu Val Lys Val Ser Arg Asp Gly Phe Ser Val
                645                 650                 655

Lys Asn Gly Ser Asp Glu Ser Lys Leu Ala Ser Thr Lys Leu Ser Ile
            660                 665                 670

Gly Ala Glu Asn Ala Glu His Val Glu Val Thr Lys Ser Gly Ile Ala
        675                 680                 685
```

Leu Lys Ala Asp Asn Thr Ser Asp Lys Ser Ile Thr Leu Ala Gln
    690                 695                 700

Asp Ala Ile Thr Leu Ala Gly Asn Ala Thr Gly Ala Ile Lys Leu
705                 710                 715                 720

Thr Gly Val Ala Asp Gly Asn Ile Thr Val Asn Ser Lys Asp Ala Val
                725                 730                 735

Asn Gly Gly Gln Leu Arg Thr Leu Leu Gly Val Asp Ser Gly Ala Lys
            740                 745                 750

Ile Gly Gly Thr Glu Lys Thr Thr Ile Ser Glu Ala Ile Ser Asp Val
        755                 760                 765

Lys Gln Ala Leu Thr Asp Ala Thr Leu Ala Tyr Lys Ala Asp Asn Lys
    770                 775                 780

Asn Gly Lys Thr Val Lys Leu Thr Asp Gly Leu Asn Phe Thr Ser Thr
785                 790                 795                 800

Thr Asn Ile Asp Ala Ser Val Glu Asp Asn Gly Val Val Lys Phe Thr
                805                 810                 815

Leu Lys Asp Lys Leu Thr Gly Leu Lys Thr Ile Ala Thr Glu Ser Leu
            820                 825                 830

Asn Ala Ser Gln Asn Ile Ile Ala Gly Gly Thr Val Thr Val Gly Gly
        835                 840                 845

Glu Thr Glu Gly Ile Val Leu Thr Lys Ser Gly Ser Gly Asn Asp Arg
    850                 855                 860

Thr Leu Ser Leu Ser Gly Ala Gly Asn Ala Ala Thr Asp Gly Ile Lys
865                 870                 875                 880

Val Ser Gly Val Lys Ala Gly Thr Ala Asp Thr Asp Ala Val Asn Lys
                885                 890                 895

Gly Gln Leu Asp Lys Leu Phe Lys Ala Ile Asn Asp Ala Leu Gly Thr
            900                 905                 910

Thr Asp Leu Ala Val Thr Lys Asn Pro Asn Gln Thr Ser Ile Phe Asn
        915                 920                 925

Pro Ile Asn Gly Thr Ala Pro Thr Thr Phe Lys Asp Ala Val Asp Lys
    930                 935                 940

Leu Thr Thr Ala Val Asn Thr Gly Trp Gly Ser Lys Val Gly Ile Leu
945                 950                 955                 960

Ala Thr Gly Ile Asp Gly Ile Asp Ala Gly Asn Lys Lys Ile Ser Asn
                965                 970                 975

Val Ala Asp Gly Asp Ile Ser Pro Thr Ser Gly Asp Val Val Thr Gly
            980                 985                 990

Arg Gln Leu Tyr Ala Leu Met Gln Lys Gly Ile Arg Val Tyr Gly Asp
        995                 1000                1005

Glu Val Ser Pro Thr Lys Thr Gln Thr Thr Ala Pro Thr Ala Ser
    1010                1015                1020

Ser Thr Gln Gly
    1025

<210> SEQ ID NO 42
<211> LENGTH: 949
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: A fusion peptide consisting of membrane
      protein sections from each of Avibacterium paragallinarum types A
      and C

<400> SEQUENCE: 42

```
Met Asp Gly Thr Ile Thr Phe Thr Asn Ile Gly Gly Thr Gly Gln Ala
1               5                   10                  15

Thr Ile His Asp Ala Ile Asn Asn Val Leu Thr Lys Gly Ile Tyr Leu
            20                  25                  30

Lys Ala Asp Gln Asn Asp Pro Thr Gly Asn Gln Gly Gln Lys Val Glu
        35                  40                  45

Leu Gly Asn Ala Ile Thr Leu Ser Ala Thr Asn Gln Trp Ala Asn Asn
    50                  55                  60

Gly Val Asn Tyr Lys Thr Asn Asn Leu Thr Thr Tyr Asn Ser Gln Asn
65                  70                  75                  80

Gly Thr Ile Leu Phe Gly Met Arg Glu Asp Pro Ser Val Lys Gln Ile
                85                  90                  95

Thr Ala Gly Thr Tyr Asn Thr Thr Gly Asp Ala Asn Asn Lys Asn Gln
            100                 105                 110

Leu Asn Asn Thr Leu Gln Gln Thr Thr Leu Glu Ala Thr Gly Ile Thr
            115                 120                 125

Ser Ser Val Gly Ser Thr Asn Tyr Ala Gly Phe Ser Leu Gly Ala Asp
    130                 135                 140

Ser Val Thr Phe Ser Lys Gly Ala Gly Thr Val Lys Leu Ser Gly
145                 150                 155                 160

Val Ser Asp Ala Thr Ala Asp Thr Asp Ala Ala Thr Leu Lys Gln Val
                165                 170                 175

Lys Glu Tyr Arg Thr Thr Leu Val Gly Asp Asn Asp Ile Thr Ala Ala
            180                 185                 190

Asp Arg Ser Gly Gly Thr Ser Asn Gly Ile Thr Tyr Asn Leu Ser Leu
        195                 200                 205

Asn Lys Gly Thr Val Ser Ala Thr Glu Glu Lys Val Val Ser Gly Lys
    210                 215                 220

Thr Val Tyr Glu Ala Ile Arg Asn Ala Ile Thr Gly Asn Ile Phe Thr
225                 230                 235                 240

Ile Gly Leu Asp Asp Thr Thr Leu Asn Lys Ile Asn Asn Pro Ala Asp
                245                 250                 255

Gln Asp Leu Ser Asn Leu Ser Glu Ser Gly Lys Asn Ala Ile Thr Gly
            260                 265                 270

Leu Val Asp Val Val Lys Lys Thr Asn Ser Pro Ile Thr Val Glu Pro
        275                 280                 285

Ser Thr Asp Ser Asn Lys Lys Lys Thr Phe Thr Val Gly Val Asp Phe
    290                 295                 300

Thr Asp Thr Ile Thr Glu Gly Asp Ala Thr Asp Lys Lys Leu Thr
305                 310                 315                 320

Thr Ser Lys Ser Val Glu Ser Tyr Val Thr Asn Lys Leu Ala Asn Phe
                325                 330                 335

Ser Thr Asp Ile Leu Leu Ser Asp Gly Arg Ser Gly Asn Ala Thr Thr
            340                 345                 350

Ala Asn Asp Gly Val Gly Lys Arg Arg Leu Ser Asp Gly Phe Thr Ile
        355                 360                 365

Lys Ser Glu Asn Phe Thr Leu Gly Ser Lys Gln Tyr Asn Gly Ser Asp
    370                 375                 380

Ser Leu Gly Val Met Tyr Asp Asp Gln Asn Gly Val Phe Lys Leu Ser
385                 390                 395                 400

Leu Asn Met Thr Ala Leu Gly Ser Asp Gly Thr Ile Thr Phe Thr Asn
                405                 410                 415
```

```
Ile Gly Gly Thr Gly Gln Asp Thr Ile His Asp Ala Ile Asn Asn Val
            420                 425                 430

Leu Thr Lys Leu Ile Ser Leu Ser Ala Thr Glu Glu Glu Val Val
            435                 440                 445

Ser Gly Glu Ala Val Tyr Asp Ala Leu Lys Gly Ala Lys Pro Thr Val
450                 455                 460

Ser Ala Glu Ala Asn Lys Gly Ile Thr Gly Leu Val Asp Val Val Lys
465                 470                 475                 480

Lys Ala Asn Ser Pro Ile Thr Val Glu Pro Ser Thr Asp Asn Lys
            485                 490                 495

Lys Lys Thr Phe Thr Val Gly Leu Met Lys Asp Ile Glu Gly Val Asn
            500                 505                 510

Ser Ile Thr Phe Asp Lys Ser Gly Gln Asp Leu Asn Gln Val Thr Gly
            515                 520                 525

Arg Met Ser Ser Ala Gly Leu Thr Phe Lys Lys Gly Asp Thr Thr Asn
            530                 535                 540

Gly Ser Thr Thr Thr Phe Ala Glu Asp Gly Leu Thr Ile Asp Ser Thr
545                 550                 555                 560

Thr Asn Ser Ala Gln Thr Asn Leu Val Lys Val Ser Arg Asp Gly Phe
                    565                 570                 575

Ser Val Lys Asn Gly Ser Asp Glu Ser Lys Leu Ala Ser Thr Lys Leu
            580                 585                 590

Ser Ile Gly Ala Glu Asn Ala Glu His Val Glu Val Thr Lys Ser Gly
            595                 600                 605

Ile Ala Leu Lys Ala Asp Asn Thr Ser Asp Lys Ser Ile Thr Leu
610                 615                 620

Ala Gln Asp Ala Ile Thr Leu Ala Gly Asn Ala Thr Gly Thr Ala Ile
625                 630                 635                 640

Lys Leu Thr Gly Val Ala Asp Gly Asn Ile Thr Val Asn Ser Lys Asp
                    645                 650                 655

Ala Val Asn Gly Gly Gln Leu Arg Thr Leu Leu Gly Val Asp Ser Gly
                    660                 665                 670

Ala Lys Ile Gly Gly Thr Glu Lys Thr Thr Ile Ser Glu Ala Ile Ser
            675                 680                 685

Asp Val Lys Gln Ala Leu Thr Asp Ala Thr Leu Ala Tyr Lys Ala Asp
            690                 695                 700

Asn Lys Asn Gly Lys Thr Val Lys Leu Thr Asp Gly Leu Asn Phe Thr
705                 710                 715                 720

Ser Thr Thr Asn Ile Asp Ala Ser Val Glu Asp Asn Gly Val Val Lys
                    725                 730                 735

Phe Thr Leu Lys Asp Lys Leu Thr Gly Leu Lys Thr Ile Ala Thr Glu
                    740                 745                 750

Ser Leu Asn Ala Ser Gln Asn Ile Ile Ala Gly Gly Thr Val Thr Val
            755                 760                 765

Gly Gly Glu Thr Glu Gly Ile Val Leu Thr Lys Ser Gly Ser Gly Asn
            770                 775                 780

Asp Arg Thr Leu Ser Leu Ser Gly Ala Gly Asn Ala Ala Thr Asp Gly
785                 790                 795                 800

Ile Lys Val Ser Gly Val Lys Ala Gly Thr Ala Asp Thr Asp Ala Val
                    805                 810                 815

Asn Lys Gly Gln Leu Asp Lys Leu Phe Lys Ala Ile Asn Asp Ala Leu
            820                 825                 830

Gly Thr Thr Asp Leu Ala Val Thr Lys Asn Pro Asn Gln Thr Ser Ile
            835                 840                 845
```

```
Phe Asn Pro Ile Asn Gly Thr Ala Pro Thr Thr Phe Lys Asp Ala Val
    850                 855                 860

Asp Lys Leu Thr Thr Ala Val Asn Thr Gly Trp Gly Ser Lys Val Gly
865                 870                 875                 880

Ile Leu Ala Thr Gly Ile Asp Gly Ile Asp Ala Gly Asn Lys Lys Ile
                885                 890                 895

Ser Asn Val Ala Asp Gly Asp Ile Ser Pro Thr Ser Gly Asp Val Val
            900                 905                 910

Thr Gly Arg Gln Leu Tyr Ala Leu Met Gln Lys Gly Ile Arg Val Tyr
        915                 920                 925

Gly Asp Glu Val Ser Pro Thr Lys Thr Gln Thr Thr Ala Pro Thr Ala
930                 935                 940

Ser Ser Thr Gln Gly
945

<210> SEQ ID NO 43
<211> LENGTH: 810
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: A fusion peptide consisting of membrane protein
      sections from each of Avibacterium paragallinarum types A and C

<400> SEQUENCE: 43

Met Asp Gly Thr Ile Thr Phe Thr Asn Ile Gly Gly Thr Gly Gln Ala
1               5                   10                  15

Thr Ile His Asp Ala Ile Asn Asn Val Leu Thr Lys Gly Ile Tyr Leu
            20                  25                  30

Lys Ala Asp Gln Asn Asp Pro Thr Gly Asn Gln Gly Gln Lys Val Glu
        35                  40                  45

Leu Gly Asn Ala Ile Thr Leu Ser Ala Thr Asn Gln Trp Ala Asn Asn
    50                  55                  60

Gly Val Asn Tyr Lys Thr Asn Asn Leu Thr Thr Tyr Asn Ser Gln Asn
65                  70                  75                  80

Gly Thr Ile Leu Phe Gly Met Arg Glu Asp Pro Ser Val Lys Gln Ile
                85                  90                  95

Thr Ala Gly Thr Tyr Asn Thr Thr Gly Asp Ala Asn Asn Lys Asn Gln
            100                 105                 110

Leu Asn Thr Leu Gln Gln Thr Thr Leu Glu Ala Thr Gly Ile Thr
        115                 120                 125

Ser Ser Val Gly Ser Thr Asn Tyr Ala Gly Phe Ser Leu Gly Ala Asp
    130                 135                 140

Ser Val Thr Phe Ser Lys Gly Ala Gly Thr Val Lys Leu Ser Gly
145                 150                 155                 160

Val Ser Asp Ala Thr Ala Asp Thr Ala Ala Thr Leu Lys Gln Val
                165                 170                 175

Lys Glu Tyr Arg Thr Thr Leu Val Gly Asp Asn Asp Ile Thr Ala Ala
            180                 185                 190

Asp Arg Ser Gly Gly Thr Ser Asn Gly Ile Thr Tyr Asn Leu Ser Leu
        195                 200                 205

Asn Lys Gly Thr Val Ser Ala Thr Glu Glu Val Val Ser Gly Lys
    210                 215                 220

Thr Val Tyr Glu Ala Ile Arg Asn Ala Ile Thr Gly Asn Ile Phe Thr
225                 230                 235                 240
```

```
Ile Gly Leu Asp Asp Thr Thr Leu Asn Lys Ile Asn Pro Ala Asp
                245                 250                 255

Gln Asp Leu Ser Asn Leu Ser Glu Ser Gly Lys Gly Ser Asp Gly Thr
            260                 265                 270

Ile Thr Phe Thr Asn Ile Gly Gly Thr Gly Gln Asp Thr Ile His Asp
                275                 280                 285

Ala Ile Asn Asn Val Leu Thr Lys Leu Ile Ser Leu Ser Ala Thr Glu
            290                 295                 300

Glu Glu Glu Val Val Ser Gly Glu Ala Val Tyr Asp Ala Leu Lys Gly
305                 310                 315                 320

Ala Lys Pro Thr Val Ser Ala Glu Ala Asn Lys Gly Ile Thr Gly Leu
                325                 330                 335

Val Asp Val Val Lys Lys Ala Asn Ser Pro Ile Thr Val Glu Pro Ser
                340                 345                 350

Thr Asp Asn Asn Lys Lys Lys Thr Phe Thr Val Gly Leu Met Lys Asp
                355                 360                 365

Ile Glu Gly Val Asn Ser Ile Thr Phe Asp Lys Ser Gly Gln Asp Leu
            370                 375                 380

Asn Gln Val Thr Gly Arg Met Ser Ser Ala Gly Leu Thr Phe Lys Lys
385                 390                 395                 400

Gly Asp Thr Thr Asn Gly Ser Thr Thr Thr Phe Ala Glu Asp Gly Leu
                405                 410                 415

Thr Ile Asp Ser Thr Thr Asn Ser Ala Gln Thr Asn Leu Val Lys Val
                420                 425                 430

Ser Arg Asp Gly Phe Ser Val Lys Asn Gly Ser Asp Glu Ser Lys Leu
            435                 440                 445

Ala Ser Thr Lys Leu Ser Ile Gly Ala Glu Asn Ala Glu His Val Glu
            450                 455                 460

Val Thr Lys Ser Gly Ile Ala Leu Lys Ala Asp Asn Thr Ser Asp Lys
465                 470                 475                 480

Ser Ser Ile Thr Leu Ala Gln Asp Ala Ile Thr Leu Ala Gly Asn Ala
                485                 490                 495

Thr Gly Thr Ala Ile Lys Leu Thr Gly Val Ala Asp Gly Asn Ile Thr
            500                 505                 510

Val Asn Ser Lys Asp Ala Val Asn Gly Gly Gln Leu Arg Thr Leu Leu
            515                 520                 525

Gly Val Asp Ser Gly Ala Lys Ile Gly Gly Thr Glu Lys Thr Thr Ile
            530                 535                 540

Ser Glu Ala Ile Ser Asp Val Lys Gln Ala Leu Thr Asp Ala Thr Leu
545                 550                 555                 560

Ala Tyr Lys Ala Asp Asn Lys Asn Gly Lys Thr Val Lys Leu Thr Asp
                565                 570                 575

Gly Leu Asn Phe Thr Ser Thr Thr Asn Ile Asp Ala Ser Val Glu Asp
            580                 585                 590

Asn Gly Val Val Lys Phe Thr Leu Lys Asp Lys Leu Thr Gly Leu Lys
            595                 600                 605

Thr Ile Ala Thr Glu Ser Leu Asn Ala Ser Gln Asn Ile Ile Ala Gly
            610                 615                 620

Gly Thr Val Thr Val Gly Gly Glu Thr Glu Ile Val Leu Thr Lys
625                 630                 635                 640

Ser Gly Ser Gly Asn Asp Arg Thr Leu Ser Leu Ser Gly Ala Gly Asn
                645                 650                 655

Ala Ala Thr Asp Gly Ile Lys Val Ser Gly Val Lys Ala Gly Thr Ala
```

```
                         660                 665                 670
Asp Thr Asp Ala Val Asn Lys Gly Gln Leu Asp Lys Leu Phe Lys Ala
            675                 680                 685

Ile Asn Asp Ala Leu Gly Thr Thr Asp Leu Ala Val Thr Lys Asn Pro
    690                 695                 700

Asn Gln Thr Ser Ile Phe Asn Pro Ile Asn Gly Thr Ala Pro Thr Thr
705                 710                 715                 720

Phe Lys Asp Ala Val Asp Lys Leu Thr Thr Ala Val Asn Thr Gly Trp
                725                 730                 735

Gly Ser Lys Val Gly Ile Leu Ala Thr Gly Ile Asp Gly Ile Asp Ala
            740                 745                 750

Gly Asn Lys Lys Ile Ser Asn Val Ala Asp Gly Asp Ile Ser Pro Thr
        755                 760                 765

Ser Gly Asp Val Val Thr Gly Arg Gln Leu Tyr Ala Leu Met Gln Lys
    770                 775                 780

Gly Ile Arg Val Tyr Gly Asp Glu Val Ser Pro Thr Lys Thr Gln Thr
785                 790                 795                 800

Thr Ala Pro Thr Ala Ser Ser Thr Gln Gly
                805                 810

<210> SEQ ID NO 44
<211> LENGTH: 1000
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: A fusion peptide consisting of membrane protein
      sections from each of Avibacterium paragallinarum types A and C

<400> SEQUENCE: 44

Met Gly Ile Tyr Leu Lys Ala Asp Gln Asn Asp Pro Thr Gly Asn Gln
1               5                   10                  15

Gly Gln Lys Val Glu Leu Gly Asn Ala Ile Thr Leu Ser Ala Thr Asn
            20                  25                  30

Gln Trp Ala Asn Asn Gly Val Asn Tyr Lys Thr Asn Asn Leu Thr Thr
        35                  40                  45

Tyr Asn Ser Gln Asn Gly Thr Ile Leu Phe Gly Met Arg Glu Asp Pro
    50                  55                  60

Ser Val Lys Gln Ile Thr Ala Gly Thr Tyr Asn Thr Thr Gly Asp Ala
65                  70                  75                  80

Asn Asn Lys Asn Gln Leu Asn Asn Thr Leu Gln Gln Thr Thr Leu Glu
                85                  90                  95

Ala Thr Gly Ile Thr Ser Ser Val Gly Ser Thr Asn Tyr Ala Gly Phe
            100                 105                 110

Ser Leu Gly Ala Asp Ser Val Thr Phe Ser Lys Gly Gly Ala Gly Thr
        115                 120                 125

Val Lys Leu Ser Gly Val Ser Asp Ala Thr Ala Asp Thr Asp Ala Ala
    130                 135                 140

Thr Leu Lys Gln Val Lys Glu Tyr Arg Thr Thr Leu Val Gly Asp Asn
145                 150                 155                 160

Asp Ile Thr Ala Ala Asp Arg Ser Gly Gly Thr Ser Asn Gly Ile Thr
                165                 170                 175

Tyr Asn Leu Ser Leu Asn Lys Gly Thr Val Ser Ala Thr Glu Glu Lys
            180                 185                 190

Val Val Ser Gly Lys Thr Val Tyr Glu Ala Ile Arg Asn Ala Ile Thr
```

```
                195                 200                 205
Gly Asn Ile Phe Thr Ile Gly Leu Asp Asp Thr Thr Leu Asn Lys Ile
    210                 215                 220

Asn Asn Pro Ala Asp Gln Asp Leu Ser Asn Leu Ser Glu Ser Gly Lys
225                 230                 235                 240

Asn Ala Ile Thr Gly Leu Val Asp Val Val Lys Lys Thr Asn Ser Pro
                245                 250                 255

Ile Thr Val Glu Pro Ser Thr Asp Ser Asn Lys Lys Lys Thr Phe Thr
                260                 265                 270

Val Gly Val Asp Phe Thr Asp Thr Ile Thr Glu Gly Asp Ala Thr Asp
            275                 280                 285

Asp Lys Lys Leu Thr Thr Ser Lys Ser Val Glu Ser Tyr Val Thr Asn
    290                 295                 300

Lys Leu Ala Asn Phe Ser Thr Asp Ile Leu Leu Ser Asp Gly Arg Ser
305                 310                 315                 320

Gly Asn Ala Thr Thr Ala Asn Asp Gly Val Gly Lys Arg Arg Leu Ser
                325                 330                 335

Asp Gly Phe Thr Ile Lys Ser Glu Asn Phe Thr Leu Gly Ser Lys Gln
            340                 345                 350

Tyr Asn Gly Ser Asp Ser Leu Gly Val Met Tyr Asp Asp Gln Asn Gly
    355                 360                 365

Val Phe Lys Leu Ser Leu Asn Met Thr Ala Leu Thr Thr Ser Leu Ala
            370                 375                 380

Asn Thr Phe Ala Lys Leu Asp Ala Ser Asn Leu Thr Asp Asp Ser Asn
385                 390                 395                 400

Lys Glu Lys Trp Arg Thr Ala Leu Asn Val Tyr Ser Lys Thr Glu Val
                405                 410                 415

Asp Ala Glu Ile Gln Lys Ser Lys Val Thr Leu Thr Pro Asp Ser Gly
            420                 425                 430

Leu Ile Phe Ala Thr Lys Gln Ala Gly Ser Gly Asn Asn Ala Gly Ile
                435                 440                 445

Asp Ala Gly Asn Lys Lys Ile Ser Asn Gly Ser Asp Gly Thr Ile Thr
450                 455                 460

Phe Thr Asn Ile Gly Gly Thr Gly Gln Asp Thr Ile His Asp Ala Ile
465                 470                 475                 480

Asn Asn Val Leu Thr Lys Leu Ile Ser Leu Ser Ala Thr Glu Glu Glu
                485                 490                 495

Glu Val Val Ser Gly Glu Ala Val Tyr Asp Ala Leu Lys Gly Ala Lys
            500                 505                 510

Pro Thr Val Ser Ala Glu Ala Asn Lys Gly Ile Thr Gly Leu Val Asp
            515                 520                 525

Val Val Lys Lys Ala Asn Ser Pro Ile Thr Val Glu Pro Ser Thr Asp
    530                 535                 540

Asn Asn Lys Lys Lys Thr Phe Thr Val Gly Leu Met Lys Asp Ile Glu
545                 550                 555                 560

Gly Val Asn Ser Ile Thr Phe Asp Lys Ser Gly Gln Asp Leu Asn Gln
                565                 570                 575

Val Thr Gly Arg Met Ser Ser Ala Gly Leu Thr Phe Lys Lys Gly Asp
            580                 585                 590

Thr Thr Asn Gly Ser Thr Thr Thr Phe Ala Glu Asp Gly Leu Thr Ile
    595                 600                 605

Asp Ser Thr Thr Asn Ser Ala Gln Thr Asn Leu Val Lys Val Ser Arg
    610                 615                 620
```

```
Asp Gly Phe Ser Val Lys Asn Gly Ser Asp Glu Ser Lys Leu Ala Ser
625                 630                 635                 640

Thr Lys Leu Ser Ile Gly Ala Glu Asn Ala Glu His Val Glu Val Thr
            645                 650                 655

Lys Ser Gly Ile Ala Leu Lys Ala Asp Asn Thr Ser Asp Lys Ser Ser
                660                 665                 670

Ile Thr Leu Ala Gln Asp Ala Ile Thr Leu Ala Gly Asn Ala Thr Gly
            675                 680                 685

Thr Ala Ile Lys Leu Thr Gly Val Ala Asp Gly Asn Ile Thr Val Asn
690                 695                 700

Ser Lys Asp Ala Val Asn Gly Gly Gln Leu Arg Thr Leu Leu Gly Val
705                 710                 715                 720

Asp Ser Gly Ala Lys Ile Gly Gly Thr Glu Lys Thr Thr Ile Ser Glu
                725                 730                 735

Ala Ile Ser Asp Val Lys Gln Ala Leu Thr Asp Ala Thr Leu Ala Tyr
            740                 745                 750

Lys Ala Asp Asn Lys Asn Gly Lys Thr Val Lys Leu Thr Asp Gly Leu
            755                 760                 765

Asn Phe Thr Ser Thr Asn Ile Asp Ala Ser Val Glu Asp Asn Gly
770                 775                 780

Val Val Lys Phe Thr Leu Lys Asp Lys Leu Thr Gly Leu Lys Thr Ile
785                 790                 795                 800

Ala Thr Glu Ser Leu Asn Ala Ser Gln Asn Ile Ile Ala Gly Gly Thr
                805                 810                 815

Val Thr Val Gly Gly Glu Thr Glu Gly Ile Val Leu Thr Lys Ser Gly
            820                 825                 830

Ser Gly Asn Asp Arg Thr Leu Ser Leu Ser Gly Ala Gly Asn Ala Ala
            835                 840                 845

Thr Asp Gly Ile Lys Val Ser Gly Val Lys Ala Gly Thr Ala Asp Thr
850                 855                 860

Asp Ala Val Asn Lys Gly Gln Leu Asp Lys Leu Phe Lys Ala Ile Asn
865                 870                 875                 880

Asp Ala Leu Gly Thr Thr Asp Leu Ala Val Thr Lys Asn Pro Asn Gln
                885                 890                 895

Thr Ser Ile Phe Asn Pro Ile Asn Gly Thr Ala Pro Thr Thr Phe Lys
            900                 905                 910

Asp Ala Val Asp Lys Leu Thr Thr Ala Val Asn Thr Gly Trp Gly Ser
            915                 920                 925

Lys Val Gly Ile Leu Ala Thr Gly Ile Asp Gly Ile Asp Ala Gly Asn
930                 935                 940

Lys Lys Ile Ser Asn Val Ala Asp Gly Asp Ile Ser Pro Thr Ser Gly
945                 950                 955                 960

Asp Val Val Thr Gly Arg Gln Leu Tyr Ala Leu Met Gln Lys Gly Ile
                965                 970                 975

Arg Val Tyr Gly Asp Glu Val Ser Pro Thr Lys Thr Gln Thr Thr Ala
            980                 985                 990

Pro Thr Ala Ser Ser Thr Gln Gly
            995                 1000

<210> SEQ ID NO 45
<211> LENGTH: 922
<212> TYPE: PRT
<213> ORGANISM: Artificial Sequence
<220> FEATURE:
<223> OTHER INFORMATION: Description of Artificial Sequence: Synthetic
      polypeptide
```

<220> FEATURE:
<223> OTHER INFORMATION: A fusion peptide consisting of membrane protein
      sections from each of Avibacterium paragallinarum types A and C

<400> SEQUENCE: 45

```
Met Gly Ile Tyr Leu Lys Ala Asp Gln Asn Asp Pro Thr Gly Asn Gln
1               5                   10                  15

Gly Gln Lys Val Glu Leu Gly Asn Ala Ile Thr Leu Ser Ala Thr Asn
            20                  25                  30

Gln Trp Ala Asn Asn Gly Val Asn Tyr Lys Thr Asn Asn Leu Thr Thr
        35                  40                  45

Tyr Asn Ser Gln Asn Gly Thr Ile Leu Phe Gly Met Arg Glu Asp Pro
    50                  55                  60

Ser Val Lys Gln Ile Thr Ala Gly Thr Tyr Asn Thr Thr Gly Asp Ala
65                  70                  75                  80

Asn Asn Lys Asn Gln Leu Asn Asn Thr Leu Gln Gln Thr Thr Leu Glu
                85                  90                  95

Ala Thr Gly Ile Thr Ser Ser Val Gly Ser Thr Asn Tyr Ala Gly Phe
            100                 105                 110

Ser Leu Gly Ala Asp Ser Val Thr Phe Ser Lys Gly Gly Ala Gly Thr
        115                 120                 125

Val Lys Leu Ser Gly Val Ser Asp Ala Thr Ala Asp Thr Asp Ala Ala
130                 135                 140

Thr Leu Lys Gln Val Lys Glu Tyr Arg Thr Thr Leu Val Gly Asp Asn
145                 150                 155                 160

Asp Ile Thr Ala Ala Asp Arg Ser Gly Gly Thr Ser Asn Gly Ile Thr
                165                 170                 175

Tyr Asn Leu Ser Leu Asn Lys Gly Thr Val Ser Ala Thr Glu Glu Lys
            180                 185                 190

Val Val Ser Gly Lys Thr Val Tyr Glu Ala Ile Arg Asn Ala Ile Thr
        195                 200                 205

Gly Asn Ile Phe Thr Ile Gly Leu Asp Asp Thr Thr Leu Asn Lys Ile
210                 215                 220

Asn Asn Pro Ala Asp Gln Asp Leu Ser Asn Leu Ser Glu Ser Gly Lys
225                 230                 235                 240

Asn Ala Ile Thr Gly Leu Val Asp Val Lys Lys Thr Asn Ser Pro
                245                 250                 255

Ile Thr Val Glu Pro Ser Thr Asp Ser Asn Lys Lys Thr Phe Thr
            260                 265                 270

Val Gly Val Asp Phe Thr Asp Thr Ile Thr Glu Gly Asp Ala Thr Asp
        275                 280                 285

Asp Lys Lys Leu Thr Thr Ser Lys Ser Val Glu Ser Tyr Val Thr Asn
290                 295                 300

Lys Leu Ala Asn Phe Ser Thr Asp Ile Leu Leu Ser Asp Gly Arg Ser
305                 310                 315                 320

Gly Asn Ala Thr Thr Ala Asn Asp Gly Val Gly Lys Arg Arg Leu Ser
                325                 330                 335

Asp Gly Phe Thr Ile Lys Ser Glu Asn Phe Thr Leu Gly Ser Lys Gln
            340                 345                 350

Tyr Asn Gly Ser Asp Ser Leu Gly Val Met Tyr Asp Asp Gln Asn Gly
        355                 360                 365

Val Phe Lys Leu Ser Leu Asn Met Thr Ala Leu Gly Ser Asp Gly Thr
370                 375                 380

Ile Thr Phe Thr Asn Ile Gly Gly Thr Gly Gln Asp Thr Ile His Asp
385                 390                 395                 400
```

```
Ala Ile Asn Asn Val Leu Thr Lys Leu Ile Ser Leu Ser Ala Thr Glu
            405                 410                 415
Glu Glu Glu Val Val Ser Gly Glu Ala Val Tyr Asp Ala Leu Lys Gly
            420                 425                 430
Ala Lys Pro Thr Val Ser Ala Glu Ala Asn Lys Gly Ile Thr Gly Leu
            435                 440                 445
Val Asp Val Val Lys Lys Ala Asn Ser Pro Ile Thr Val Glu Pro Ser
450                 455                 460
Thr Asp Asn Asn Lys Lys Lys Thr Phe Thr Val Gly Leu Met Lys Asp
465                 470                 475                 480
Ile Glu Gly Val Asn Ser Ile Thr Phe Asp Lys Ser Gly Gln Asp Leu
                485                 490                 495
Asn Gln Val Thr Gly Arg Met Ser Ser Ala Gly Leu Thr Phe Lys Lys
            500                 505                 510
Gly Asp Thr Thr Asn Gly Ser Thr Thr Thr Phe Ala Glu Asp Gly Leu
            515                 520                 525
Thr Ile Asp Ser Thr Thr Asn Ser Ala Gln Thr Asn Leu Val Lys Val
            530                 535                 540
Ser Arg Asp Gly Phe Ser Val Lys Asn Gly Ser Asp Glu Ser Lys Leu
545                 550                 555                 560
Ala Ser Thr Lys Leu Ser Ile Gly Ala Glu Asn Ala Glu His Val Glu
                565                 570                 575
Val Thr Lys Ser Gly Ile Ala Leu Lys Ala Asp Asn Thr Ser Asp Lys
            580                 585                 590
Ser Ser Ile Thr Leu Ala Gln Asp Ala Ile Thr Leu Ala Gly Asn Ala
            595                 600                 605
Thr Gly Thr Ala Ile Lys Leu Thr Gly Val Ala Asp Gly Asn Ile Thr
            610                 615                 620
Val Asn Ser Lys Asp Ala Val Asn Gly Gly Gln Leu Arg Thr Leu Leu
625                 630                 635                 640
Gly Val Asp Ser Gly Ala Lys Ile Gly Gly Thr Glu Lys Thr Thr Ile
                645                 650                 655
Ser Glu Ala Ile Ser Asp Val Lys Gln Ala Leu Thr Asp Ala Thr Leu
            660                 665                 670
Ala Tyr Lys Ala Asp Asn Lys Asn Gly Lys Thr Val Lys Leu Thr Asp
            675                 680                 685
Gly Leu Asn Phe Thr Ser Thr Thr Asn Ile Asp Ala Ser Val Glu Asp
            690                 695                 700
Asn Gly Val Val Lys Phe Thr Leu Lys Asp Lys Leu Thr Gly Leu Lys
705                 710                 715                 720
Thr Ile Ala Thr Glu Ser Leu Asn Ala Ser Gln Asn Ile Ile Ala Gly
                725                 730                 735
Gly Thr Val Thr Val Gly Gly Glu Thr Glu Gly Ile Val Leu Thr Lys
            740                 745                 750
Ser Gly Ser Gly Asn Asp Arg Thr Leu Ser Leu Ser Gly Ala Gly Asn
            755                 760                 765
Ala Ala Thr Asp Gly Ile Lys Val Ser Gly Val Lys Ala Gly Thr Ala
            770                 775                 780
Asp Thr Asp Ala Val Asn Lys Gly Gln Leu Asp Lys Leu Phe Lys Ala
785                 790                 795                 800
Ile Asn Asp Ala Leu Gly Thr Thr Asp Leu Ala Val Thr Lys Asn Pro
                805                 810                 815
Asn Gln Thr Ser Ile Phe Asn Pro Ile Asn Gly Thr Ala Pro Thr Thr
```

```
                    820                 825                 830
Phe Lys Asp Ala Val Asp Lys Leu Thr Thr Ala Val Asn Thr Gly Trp
            835                 840                 845

Gly Ser Lys Val Gly Ile Leu Ala Thr Gly Ile Asp Gly Ile Asp Ala
        850                 855                 860

Gly Asn Lys Lys Ile Ser Asn Val Ala Asp Gly Asp Ile Ser Pro Thr
865                 870                 875                 880

Ser Gly Asp Val Val Thr Gly Arg Gln Leu Tyr Ala Leu Met Gln Lys
                885                 890                 895

Gly Ile Arg Val Tyr Gly Asp Glu Val Ser Pro Thr Lys Thr Gln Thr
            900                 905                 910

Thr Ala Pro Thr Ala Ser Ser Thr Gln Gly
            915                 920

<210> SEQ ID NO 46
<211> LENGTH: 783
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: A fusion peptide consisting of membrane protein
      sections from each of Avibacterium paragallinarum types A and C

<400> SEQUENCE: 46

Met Gly Ile Tyr Leu Lys Ala Asp Gln Asn Asp Pro Thr Gly Asn Gln
1               5                   10                  15

Gly Gln Lys Val Glu Leu Gly Asn Ala Ile Thr Leu Ser Ala Thr Asn
            20                  25                  30

Gln Trp Ala Asn Asn Gly Val Asn Tyr Lys Thr Asn Asn Leu Thr Thr
        35                  40                  45

Tyr Asn Ser Gln Asn Gly Thr Ile Leu Phe Gly Met Arg Glu Asp Pro
    50                  55                  60

Ser Val Lys Gln Ile Thr Ala Gly Thr Tyr Asn Thr Thr Gly Asp Ala
65                  70                  75                  80

Asn Asn Lys Asn Gln Leu Asn Asn Thr Leu Gln Gln Thr Thr Leu Glu
                85                  90                  95

Ala Thr Gly Ile Thr Ser Ser Val Gly Ser Thr Asn Tyr Ala Gly Phe
            100                 105                 110

Ser Leu Gly Ala Asp Ser Val Thr Phe Ser Lys Gly Gly Ala Gly Thr
        115                 120                 125

Val Lys Leu Ser Gly Val Ser Asp Ala Thr Ala Asp Thr Asp Ala Ala
    130                 135                 140

Thr Leu Lys Gln Val Lys Glu Tyr Arg Thr Thr Leu Val Gly Asp Asn
145                 150                 155                 160

Asp Ile Thr Ala Ala Asp Arg Ser Gly Gly Thr Ser Asn Gly Ile Thr
                165                 170                 175

Tyr Asn Leu Ser Leu Asn Lys Gly Thr Val Ser Ala Thr Glu Glu Lys
            180                 185                 190

Val Val Ser Gly Lys Thr Val Tyr Glu Ala Ile Arg Asn Ala Ile Thr
        195                 200                 205

Gly Asn Ile Phe Thr Ile Gly Leu Asp Asp Thr Leu Asn Lys Ile
    210                 215                 220

Asn Asn Pro Ala Asp Gln Asp Leu Ser Asn Leu Ser Glu Ser Gly Lys
225                 230                 235                 240

Gly Ser Asp Gly Thr Ile Thr Phe Thr Asn Ile Gly Gly Thr Gly Gln
```

```
                    245                 250                 255
Asp Thr Ile His Asp Ala Ile Asn Asn Val Leu Thr Lys Leu Ile Ser
            260                 265                 270

Leu Ser Ala Thr Glu Glu Glu Val Val Ser Gly Glu Ala Val Tyr
        275                 280                 285

Asp Ala Leu Lys Gly Ala Lys Pro Thr Val Ser Ala Glu Ala Asn Lys
            290                 295                 300

Gly Ile Thr Gly Leu Val Asp Val Val Lys Lys Ala Asn Ser Pro Ile
305                 310                 315                 320

Thr Val Glu Pro Ser Thr Asp Asn Asn Lys Lys Lys Thr Phe Thr Val
            325                 330                 335

Gly Leu Met Lys Asp Ile Glu Gly Val Asn Ser Ile Thr Phe Asp Lys
            340                 345                 350

Ser Gly Gln Asp Leu Asn Gln Val Thr Gly Arg Met Ser Ser Ala Gly
            355                 360                 365

Leu Thr Phe Lys Lys Gly Asp Thr Thr Asn Gly Ser Thr Thr Thr Phe
            370                 375                 380

Ala Glu Asp Gly Leu Thr Ile Asp Ser Thr Thr Asn Ser Ala Gln Thr
385                 390                 395                 400

Asn Leu Val Lys Val Ser Arg Asp Gly Phe Ser Val Lys Asn Gly Ser
                405                 410                 415

Asp Glu Ser Lys Leu Ala Ser Thr Lys Leu Ser Ile Gly Ala Glu Asn
            420                 425                 430

Ala Glu His Val Glu Val Thr Lys Ser Gly Ile Ala Leu Lys Ala Asp
            435                 440                 445

Asn Thr Ser Asp Lys Ser Ser Ile Thr Leu Ala Gln Asp Ala Ile Thr
            450                 455                 460

Leu Ala Gly Asn Ala Thr Gly Thr Ala Ile Lys Leu Thr Gly Val Ala
465                 470                 475                 480

Asp Gly Asn Ile Thr Val Asn Ser Lys Asp Ala Val Asn Gly Gly Gln
                485                 490                 495

Leu Arg Thr Leu Leu Gly Val Asp Ser Gly Ala Lys Ile Gly Gly Thr
            500                 505                 510

Glu Lys Thr Thr Ile Ser Glu Ala Ile Ser Asp Val Lys Gln Ala Leu
            515                 520                 525

Thr Asp Ala Thr Leu Ala Tyr Lys Ala Asp Asn Lys Asn Gly Lys Thr
            530                 535                 540

Val Lys Leu Thr Asp Gly Leu Asn Phe Thr Ser Thr Asn Ile Asp
545                 550                 555                 560

Ala Ser Val Glu Asp Asn Gly Val Val Lys Phe Thr Leu Lys Asp Lys
                565                 570                 575

Leu Thr Gly Leu Lys Thr Ile Ala Thr Glu Ser Leu Asn Ala Ser Gln
            580                 585                 590

Asn Ile Ile Ala Gly Gly Thr Val Thr Val Gly Gly Glu Thr Glu Gly
            595                 600                 605

Ile Val Leu Thr Lys Ser Gly Ser Gly Asn Asp Arg Thr Leu Ser Leu
            610                 615                 620

Ser Gly Ala Gly Asn Ala Ala Thr Asp Gly Ile Lys Val Ser Gly Val
625                 630                 635                 640

Lys Ala Gly Thr Ala Asp Thr Asp Ala Val Asn Lys Gly Gln Leu Asp
                645                 650                 655

Lys Leu Phe Lys Ala Ile Asn Asp Ala Leu Gly Thr Thr Asp Leu Ala
            660                 665                 670
```

```
Val Thr Lys Asn Pro Asn Gln Thr Ser Ile Phe Asn Pro Ile Asn Gly
            675                 680                 685

Thr Ala Pro Thr Thr Phe Lys Asp Ala Val Asp Lys Leu Thr Thr Ala
        690                 695                 700

Val Asn Thr Gly Trp Gly Ser Lys Val Gly Ile Leu Ala Thr Gly Ile
705                 710                 715                 720

Asp Gly Ile Asp Ala Gly Asn Lys Lys Ile Ser Asn Val Ala Asp Gly
                725                 730                 735

Asp Ile Ser Pro Thr Ser Gly Asp Val Val Thr Gly Arg Gln Leu Tyr
                    740                 745                 750

Ala Leu Met Gln Lys Gly Ile Arg Val Tyr Gly Asp Glu Val Ser Pro
                755                 760                 765

Thr Lys Thr Gln Thr Thr Ala Pro Thr Ala Ser Ser Thr Gln Gly
            770                 775                 780

<210> SEQ ID NO 47
<211> LENGTH: 930
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: A fusion peptide consisting of membrane protein
      sections from each of Avibacterium paragallinarum types A and C

<400> SEQUENCE: 47

Met Gly Thr Tyr Asn Thr Thr Gly Asp Ala Asn Asn Lys Asn Gln Leu
1               5                   10                  15

Asn Asn Thr Leu Gln Gln Thr Thr Leu Glu Ala Thr Gly Ile Thr Ser
            20                  25                  30

Ser Val Gly Ser Thr Asn Tyr Ala Gly Phe Ser Leu Gly Ala Asp Ser
        35                  40                  45

Val Thr Phe Ser Lys Gly Ala Gly Thr Val Lys Leu Ser Gly Val
    50                  55                  60

Ser Asp Ala Thr Ala Asp Thr Ala Ala Thr Leu Lys Gln Val Lys
65                  70                  75                  80

Glu Tyr Arg Thr Thr Leu Val Gly Asp Asn Asp Ile Thr Ala Ala Asp
                85                  90                  95

Arg Ser Gly Gly Thr Ser Asn Gly Ile Thr Tyr Asn Leu Ser Leu Asn
                100                 105                 110

Lys Gly Thr Val Ser Ala Thr Glu Glu Lys Val Val Ser Gly Lys Thr
            115                 120                 125

Val Tyr Glu Ala Ile Arg Asn Ala Ile Thr Gly Asn Ile Phe Thr Ile
    130                 135                 140

Gly Leu Asp Asp Thr Thr Leu Asn Lys Ile Asn Asn Pro Ala Asp Gln
145                 150                 155                 160

Asp Leu Ser Asn Leu Ser Glu Ser Gly Lys Asn Ala Ile Thr Gly Leu
                165                 170                 175

Val Asp Val Val Lys Lys Thr Asn Ser Pro Ile Thr Val Glu Pro Ser
            180                 185                 190

Thr Asp Ser Asn Lys Lys Lys Thr Phe Thr Val Gly Val Asp Phe Thr
        195                 200                 205

Asp Thr Ile Thr Glu Gly Asp Ala Thr Asp Lys Lys Leu Thr Thr
    210                 215                 220

Ser Lys Ser Val Glu Ser Tyr Val Thr Asn Lys Leu Ala Asn Phe Ser
225                 230                 235                 240
```

```
Thr Asp Ile Leu Leu Ser Asp Gly Arg Ser Asn Ala Thr Thr Ala
            245                 250                 255

Asn Asp Gly Val Gly Lys Arg Arg Leu Ser Asp Gly Phe Thr Ile Lys
                260                 265                 270

Ser Glu Asn Phe Thr Leu Gly Ser Lys Gln Tyr Asn Gly Ser Asp Ser
            275                 280                 285

Leu Gly Val Met Tyr Asp Asp Gln Asn Gly Val Phe Lys Leu Ser Leu
            290                 295                 300

Asn Met Thr Ala Leu Thr Thr Ser Leu Ala Asn Thr Phe Ala Lys Leu
305                 310                 315                 320

Asp Ala Ser Asn Leu Thr Asp Asp Ser Asn Lys Glu Lys Trp Arg Thr
                325                 330                 335

Ala Leu Asn Val Tyr Ser Lys Thr Glu Val Asp Ala Glu Ile Gln Lys
                340                 345                 350

Ser Lys Val Thr Leu Thr Pro Asp Ser Gly Leu Ile Phe Ala Thr Lys
                355                 360                 365

Gln Ala Gly Ser Gly Asn Asn Ala Gly Ile Asp Ala Gly Asn Lys Lys
            370                 375                 380

Ile Ser Asn Gly Ser Asp Gly Thr Ile Thr Phe Thr Asn Ile Gly Gly
385                 390                 395                 400

Thr Gly Gln Asp Thr Ile His Asp Ala Ile Asn Asn Val Leu Thr Lys
                405                 410                 415

Leu Ile Ser Leu Ser Ala Thr Glu Glu Glu Val Val Ser Gly Glu
            420                 425                 430

Ala Val Tyr Asp Ala Leu Lys Gly Ala Lys Pro Thr Val Ser Ala Glu
            435                 440                 445

Ala Asn Lys Gly Ile Thr Gly Leu Val Asp Val Val Lys Lys Ala Asn
450                 455                 460

Ser Pro Ile Thr Val Glu Pro Ser Thr Asp Asn Lys Lys Lys Thr
465                 470                 475                 480

Phe Thr Val Gly Leu Met Lys Asp Ile Glu Gly Val Asn Ser Ile Thr
                485                 490                 495

Phe Asp Lys Ser Gly Gln Asp Leu Asn Gln Val Thr Gly Arg Met Ser
                500                 505                 510

Ser Ala Gly Leu Thr Phe Lys Lys Gly Asp Thr Thr Asn Gly Ser Thr
            515                 520                 525

Thr Thr Phe Ala Glu Asp Gly Leu Thr Ile Asp Ser Thr Thr Asn Ser
530                 535                 540

Ala Gln Thr Asn Leu Val Lys Val Ser Arg Asp Gly Phe Ser Val Lys
545                 550                 555                 560

Asn Gly Ser Asp Glu Ser Lys Leu Ala Ser Thr Lys Leu Ser Ile Gly
                565                 570                 575

Ala Glu Asn Ala Glu His Val Glu Val Thr Lys Ser Gly Ile Ala Leu
                580                 585                 590

Lys Ala Asp Asn Thr Ser Asp Lys Ser Ser Ile Thr Leu Ala Gln Asp
                595                 600                 605

Ala Ile Thr Leu Ala Gly Asn Ala Thr Gly Thr Ala Ile Lys Leu Thr
            610                 615                 620

Gly Val Ala Asp Gly Asn Ile Thr Val Asn Ser Lys Asp Ala Val Asn
625                 630                 635                 640

Gly Gly Gln Leu Arg Thr Leu Leu Gly Val Asp Ser Gly Ala Lys Ile
                645                 650                 655

Gly Gly Thr Glu Lys Thr Thr Ile Ser Glu Ala Ile Ser Asp Val Lys
                660                 665                 670
```

-continued

```
Gln Ala Leu Thr Asp Ala Thr Leu Ala Tyr Lys Ala Asp Asn Lys Asn
            675                 680                 685

Gly Lys Thr Val Lys Leu Thr Asp Gly Leu Asn Phe Thr Ser Thr Thr
        690                 695                 700

Asn Ile Asp Ala Ser Val Glu Asp Asn Gly Val Val Lys Phe Thr Leu
705                 710                 715                 720

Lys Asp Lys Leu Thr Gly Leu Lys Thr Ile Ala Thr Glu Ser Leu Asn
                725                 730                 735

Ala Ser Gln Asn Ile Ile Ala Gly Gly Thr Val Thr Val Gly Gly Glu
            740                 745                 750

Thr Glu Gly Ile Val Leu Thr Lys Ser Gly Ser Gly Asn Asp Arg Thr
        755                 760                 765

Leu Ser Leu Ser Gly Ala Gly Asn Ala Ala Thr Asp Gly Ile Lys Val
        770                 775                 780

Ser Gly Val Lys Ala Gly Thr Ala Asp Thr Asp Ala Val Asn Lys Gly
785                 790                 795                 800

Gln Leu Asp Lys Leu Phe Lys Ala Ile Asn Asp Ala Leu Gly Thr Thr
                805                 810                 815

Asp Leu Ala Val Thr Lys Asn Pro Asn Gln Thr Ser Ile Phe Asn Pro
            820                 825                 830

Ile Asn Gly Thr Ala Pro Thr Thr Phe Lys Asp Ala Val Asp Lys Leu
        835                 840                 845

Thr Thr Ala Val Asn Thr Gly Trp Gly Ser Lys Val Gly Ile Leu Ala
        850                 855                 860

Thr Gly Ile Asp Gly Ile Asp Ala Gly Asn Lys Lys Ile Ser Asn Val
865                 870                 875                 880

Ala Asp Gly Asp Ile Ser Pro Thr Ser Gly Asp Val Val Thr Gly Arg
                885                 890                 895

Gln Leu Tyr Ala Leu Met Gln Lys Gly Ile Arg Val Tyr Gly Asp Glu
            900                 905                 910

Val Ser Pro Thr Lys Thr Gln Thr Thr Ala Pro Thr Ala Ser Ser Thr
        915                 920                 925

Gln Gly
    930

<210> SEQ ID NO 48
<211> LENGTH: 852
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: A fusion peptide consisting of membrane protein
      sections from each of Avibacterium paragallinarum types A and C

<400> SEQUENCE: 48

Met Gly Thr Tyr Asn Thr Thr Gly Asp Ala Asn Asn Lys Asn Gln Leu
1               5                   10                  15

Asn Asn Thr Leu Gln Gln Thr Thr Leu Glu Ala Thr Gly Ile Thr Ser
            20                  25                  30

Ser Val Gly Ser Thr Asn Tyr Ala Gly Phe Ser Leu Gly Ala Asp Ser
        35                  40                  45

Val Thr Phe Ser Lys Gly Gly Ala Gly Thr Val Lys Leu Ser Gly Val
    50                  55                  60

Ser Asp Ala Thr Ala Asp Thr Asp Ala Ala Thr Leu Lys Gln Val Lys
65                  70                  75                  80
```

```
Glu Tyr Arg Thr Thr Leu Val Gly Asp Asn Asp Ile Thr Ala Ala Asp
                85                  90                  95

Arg Ser Gly Gly Thr Ser Asn Gly Ile Thr Tyr Asn Leu Ser Leu Asn
            100                 105                 110

Lys Gly Thr Val Ser Ala Thr Glu Glu Lys Val Val Ser Gly Lys Thr
            115                 120                 125

Val Tyr Glu Ala Ile Arg Asn Ala Ile Thr Gly Asn Ile Phe Thr Ile
130                 135                 140

Gly Leu Asp Asp Thr Thr Leu Asn Lys Ile Asn Asn Pro Ala Asp Gln
145                 150                 155                 160

Asp Leu Ser Asn Leu Ser Glu Ser Gly Lys Asn Ala Ile Thr Gly Leu
                165                 170                 175

Val Asp Val Val Lys Lys Thr Asn Ser Pro Ile Thr Val Glu Pro Ser
            180                 185                 190

Thr Asp Ser Asn Lys Lys Lys Thr Phe Thr Val Gly Val Asp Phe Thr
            195                 200                 205

Asp Thr Ile Thr Glu Gly Asp Ala Thr Asp Lys Lys Leu Thr Thr
        210                 215                 220

Ser Lys Ser Val Glu Ser Tyr Val Thr Asn Lys Leu Ala Asn Phe Ser
225                 230                 235                 240

Thr Asp Ile Leu Leu Ser Asp Gly Arg Ser Gly Asn Ala Thr Thr Ala
            245                 250                 255

Asn Asp Gly Val Gly Lys Arg Arg Leu Ser Asp Gly Phe Thr Ile Lys
            260                 265                 270

Ser Glu Asn Phe Thr Leu Gly Ser Lys Gln Tyr Asn Gly Ser Asp Ser
            275                 280                 285

Leu Gly Val Met Tyr Asp Asp Gln Asn Gly Val Phe Lys Leu Ser Leu
            290                 295                 300

Asn Met Thr Ala Leu Gly Ser Asp Gly Thr Ile Thr Phe Thr Asn Ile
305                 310                 315                 320

Gly Gly Thr Gly Gln Asp Thr Ile His Asp Ala Ile Asn Asn Val Leu
            325                 330                 335

Thr Lys Leu Ile Ser Leu Ser Ala Thr Glu Glu Glu Val Val Ser
            340                 345                 350

Gly Glu Ala Val Tyr Asp Ala Leu Lys Gly Ala Lys Pro Thr Val Ser
            355                 360                 365

Ala Glu Ala Asn Lys Gly Ile Thr Gly Leu Val Asp Val Val Lys Lys
370                 375                 380

Ala Asn Ser Pro Ile Thr Val Glu Pro Ser Thr Asp Asn Asn Lys Lys
385                 390                 395                 400

Lys Thr Phe Thr Val Gly Leu Met Lys Asp Ile Glu Gly Val Asn Ser
            405                 410                 415

Ile Thr Phe Asp Lys Ser Gly Gln Asp Leu Asn Gln Val Thr Gly Arg
            420                 425                 430

Met Ser Ser Ala Gly Leu Thr Phe Lys Lys Gly Asp Thr Thr Asn Gly
            435                 440                 445

Ser Thr Thr Thr Phe Ala Glu Asp Gly Leu Thr Ile Asp Ser Thr Thr
    450                 455                 460

Asn Ser Ala Gln Thr Asn Leu Val Lys Val Ser Arg Asp Gly Phe Ser
465                 470                 475                 480

Val Lys Asn Gly Ser Asp Glu Ser Lys Leu Ala Ser Thr Lys Leu Ser
            485                 490                 495

Ile Gly Ala Glu Asn Ala Glu His Val Glu Val Thr Lys Ser Gly Ile
```

```
                500             505             510
Ala Leu Lys Ala Asp Asn Thr Ser Asp Lys Ser Ile Thr Leu Ala
        515                 520             525

Gln Asp Ala Ile Thr Leu Ala Gly Asn Ala Thr Gly Thr Ala Ile Lys
        530                 535             540

Leu Thr Gly Val Ala Asp Gly Asn Ile Thr Val Asn Ser Lys Asp Ala
545                 550             555                 560

Val Asn Gly Gly Gln Leu Arg Thr Leu Leu Gly Val Asp Ser Gly Ala
                565             570             575

Lys Ile Gly Gly Thr Glu Lys Thr Thr Ile Ser Glu Ala Ile Ser Asp
            580             585             590

Val Lys Gln Ala Leu Thr Asp Ala Thr Leu Ala Tyr Lys Ala Asp Asn
            595             600             605

Lys Asn Gly Lys Thr Val Lys Leu Thr Asp Gly Leu Asn Phe Thr Ser
        610             615             620

Thr Thr Asn Ile Asp Ala Ser Val Glu Asp Asn Gly Val Val Lys Phe
625             630             635                 640

Thr Leu Lys Asp Lys Leu Thr Gly Leu Lys Thr Ile Ala Thr Glu Ser
            645             650             655

Leu Asn Ala Ser Gln Asn Ile Ile Ala Gly Gly Thr Val Thr Val Gly
            660             665             670

Gly Glu Thr Glu Gly Ile Val Leu Thr Lys Ser Gly Ser Gly Asn Asp
            675             680             685

Arg Thr Leu Ser Leu Ser Gly Ala Gly Asn Ala Ala Thr Asp Gly Ile
        690             695             700

Lys Val Ser Gly Val Lys Ala Gly Thr Ala Asp Thr Asp Ala Val Asn
705             710             715                 720

Lys Gly Gln Leu Asp Lys Leu Phe Lys Ala Ile Asn Asp Ala Leu Gly
                725             730             735

Thr Thr Asp Leu Ala Val Thr Lys Asn Pro Asn Gln Thr Ser Ile Phe
            740             745             750

Asn Pro Ile Asn Gly Thr Ala Pro Thr Thr Phe Lys Asp Ala Val Asp
            755             760             765

Lys Leu Thr Thr Ala Val Asn Thr Gly Trp Gly Ser Lys Val Gly Ile
        770             775             780

Leu Ala Thr Gly Ile Asp Gly Ile Asp Ala Gly Asn Lys Lys Ile Ser
785             790             795                 800

Asn Val Ala Asp Gly Asp Ile Ser Pro Thr Ser Gly Asp Val Val Thr
                805             810             815

Gly Arg Gln Leu Tyr Ala Leu Met Gln Lys Gly Ile Arg Val Tyr Gly
            820             825             830

Asp Glu Val Ser Pro Thr Lys Thr Gln Thr Thr Ala Pro Thr Ala Ser
        835             840             845

Ser Thr Gln Gly
        850

<210> SEQ ID NO 49
<211> LENGTH: 713
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: A fusion peptide consisting of membrane protein
      sections from each of Avibacterium paragallinarum types A and C
```

-continued

```
<400> SEQUENCE: 49

Met Gly Thr Tyr Asn Thr Thr Gly Asp Ala Asn Asn Lys Asn Gln Leu
1               5                   10                  15

Asn Asn Thr Leu Gln Gln Thr Thr Leu Glu Ala Thr Gly Ile Thr Ser
            20                  25                  30

Ser Val Gly Ser Thr Asn Tyr Ala Gly Phe Ser Leu Gly Ala Asp Ser
        35                  40                  45

Val Thr Phe Ser Lys Gly Ala Gly Thr Val Lys Leu Ser Gly Val
    50                  55                  60

Ser Asp Ala Thr Ala Asp Thr Asp Ala Ala Thr Leu Lys Gln Val Lys
65                  70                  75                  80

Glu Tyr Arg Thr Thr Leu Val Gly Asp Asn Asp Ile Thr Ala Ala Asp
                85                  90                  95

Arg Ser Gly Gly Thr Ser Asn Gly Ile Thr Tyr Asn Leu Ser Leu Asn
            100                 105                 110

Lys Gly Thr Val Ser Ala Thr Glu Glu Lys Val Val Ser Gly Lys Thr
        115                 120                 125

Val Tyr Glu Ala Ile Arg Asn Ala Ile Thr Gly Asn Ile Phe Thr Ile
130                 135                 140

Gly Leu Asp Asp Thr Thr Leu Asn Lys Ile Asn Asn Pro Ala Asp Gln
145                 150                 155                 160

Asp Leu Ser Asn Leu Ser Glu Ser Gly Lys Gly Ser Asp Gly Thr Ile
                165                 170                 175

Thr Phe Thr Asn Ile Gly Gly Thr Gly Gln Asp Thr Ile His Asp Ala
            180                 185                 190

Ile Asn Asn Val Leu Thr Lys Leu Ile Ser Leu Ser Ala Thr Glu Glu
        195                 200                 205

Glu Glu Val Val Ser Gly Glu Ala Val Tyr Asp Ala Leu Lys Gly Ala
    210                 215                 220

Lys Pro Thr Val Ser Ala Glu Ala Asn Lys Gly Ile Thr Gly Leu Val
225                 230                 235                 240

Asp Val Val Lys Lys Ala Asn Ser Pro Ile Thr Val Glu Pro Ser Thr
                245                 250                 255

Asp Asn Asn Lys Lys Thr Phe Thr Val Gly Leu Met Lys Asp Ile
            260                 265                 270

Glu Gly Val Asn Ser Ile Thr Phe Asp Lys Ser Gly Gln Asp Leu Asn
        275                 280                 285

Gln Val Thr Gly Arg Met Ser Ser Ala Gly Leu Thr Phe Lys Lys Gly
    290                 295                 300

Asp Thr Thr Asn Gly Ser Thr Thr Phe Ala Glu Asp Gly Leu Thr
305                 310                 315                 320

Ile Asp Ser Thr Thr Asn Ser Ala Gln Thr Asn Leu Val Lys Val Ser
                325                 330                 335

Arg Asp Gly Phe Ser Val Lys Asn Gly Ser Asp Glu Ser Lys Leu Ala
            340                 345                 350

Ser Thr Lys Leu Ser Ile Gly Ala Glu Asn Ala Glu His Val Glu Val
        355                 360                 365

Thr Lys Ser Gly Ile Ala Leu Lys Ala Asp Asn Thr Ser Asp Lys Ser
    370                 375                 380

Ser Ile Thr Leu Ala Gln Asp Ala Ile Thr Leu Ala Gly Asn Ala Thr
385                 390                 395                 400

Gly Thr Ala Ile Lys Leu Thr Gly Val Ala Asp Gly Asn Ile Thr Val
                405                 410                 415
```

```
Asn Ser Lys Asp Ala Val Asn Gly Gly Gln Leu Arg Thr Leu Leu Gly
            420                 425                 430

Val Asp Ser Gly Ala Lys Ile Gly Gly Thr Glu Lys Thr Thr Ile Ser
        435                 440                 445

Glu Ala Ile Ser Asp Val Lys Gln Ala Leu Thr Asp Ala Thr Leu Ala
    450                 455                 460

Tyr Lys Ala Asp Asn Lys Asn Gly Lys Thr Val Lys Leu Thr Asp Gly
465                 470                 475                 480

Leu Asn Phe Thr Ser Thr Thr Asn Ile Asp Ala Ser Val Glu Asp Asn
                485                 490                 495

Gly Val Val Lys Phe Thr Leu Lys Asp Lys Leu Thr Gly Leu Lys Thr
            500                 505                 510

Ile Ala Thr Glu Ser Leu Asn Ala Ser Gln Asn Ile Ile Ala Gly Gly
        515                 520                 525

Thr Val Thr Val Gly Gly Glu Thr Glu Gly Ile Val Leu Thr Lys Ser
    530                 535                 540

Gly Ser Gly Asn Asp Arg Thr Leu Ser Leu Ser Gly Ala Gly Asn Ala
545                 550                 555                 560

Ala Thr Asp Gly Ile Lys Val Ser Gly Val Lys Ala Gly Thr Ala Asp
                565                 570                 575

Thr Asp Ala Val Asn Lys Gly Gln Leu Asp Lys Leu Phe Lys Ala Ile
            580                 585                 590

Asn Asp Ala Leu Gly Thr Thr Asp Leu Ala Val Thr Lys Asn Pro Asn
        595                 600                 605

Gln Thr Ser Ile Phe Asn Pro Ile Asn Gly Thr Ala Pro Thr Thr Phe
    610                 615                 620

Lys Asp Ala Val Asp Lys Leu Thr Thr Ala Val Asn Thr Gly Trp Gly
625                 630                 635                 640

Ser Lys Val Gly Ile Leu Ala Thr Gly Ile Asp Gly Ile Asp Ala Gly
                645                 650                 655

Asn Lys Lys Ile Ser Asn Val Ala Asp Gly Asp Ile Ser Pro Thr Ser
            660                 665                 670

Gly Asp Val Val Thr Gly Arg Gln Leu Tyr Ala Leu Met Gln Lys Gly
        675                 680                 685

Ile Arg Val Tyr Gly Asp Glu Val Ser Pro Thr Lys Thr Gln Thr Thr
    690                 695                 700

Ala Pro Thr Ala Ser Ser Thr Gln Gly
705                 710
```

<210> SEQ ID NO 50
<211> LENGTH: 469
<212> TYPE: PRT
<213> ORGANISM: Avibacterium paragallinarum
<220> FEATURE:
<223> OTHER INFORMATION: type C

<400> SEQUENCE: 50

```
Asp Gly Thr Ile Thr Phe Thr Asn Ile Gly Gly Thr Gly Gln Asp Thr
1               5                   10                  15

Ile His Asp Ala Ile Asn Asn Val Leu Thr Lys Leu Ile Ser Leu Ser
            20                  25                  30

Ala Thr Glu Glu Glu Glu Val Val Ser Gly Glu Ala Val Tyr Asp Ala
        35                  40                  45

Leu Lys Gly Ala Lys Pro Thr Val Ser Ala Glu Ala Asn Lys Gly Ile
    50                  55                  60

Thr Gly Leu Val Asp Val Val Lys Lys Ala Asn Ser Pro Ile Thr Val
```

```
                65                  70                  75                  80
        Glu Pro Ser Thr Asp Asn Asn Lys Lys Lys Thr Phe Thr Val Gly Leu
                        85                  90                  95

Met Lys Asp Ile Glu Gly Val Asn Ser Ile Thr Phe Asp Lys Ser Gly
                        100                 105                 110

Gln Asp Leu Asn Gln Val Thr Gly Arg Met Ser Ser Ala Gly Leu Thr
                        115                 120                 125

Phe Lys Lys Gly Asp Thr Thr Asn Gly Ser Thr Thr Phe Ala Glu
        130                     135                 140

Asp Gly Leu Thr Ile Asp Ser Thr Thr Asn Ser Ala Gln Thr Asn Leu
        145                     150                 155                 160

Val Lys Val Ser Arg Asp Gly Phe Ser Val Lys Asn Gly Ser Asp Glu
                        165                 170                 175

Ser Lys Leu Ala Ser Thr Lys Leu Ser Ile Gly Ala Glu Asn Ala Glu
                        180                 185                 190

His Val Glu Val Thr Lys Ser Gly Ile Ala Leu Lys Ala Asp Asn Thr
                        195                 200                 205

Ser Asp Lys Ser Ser Ile Thr Leu Ala Gln Asp Ala Ile Thr Leu Ala
        210                     215                 220

Gly Asn Ala Thr Gly Thr Ala Ile Lys Leu Thr Gly Val Ala Asp Gly
        225                     230                 235                 240

Asn Ile Thr Val Asn Ser Lys Asp Ala Val Asn Gly Gln Leu Arg
                        245                 250                 255

Thr Leu Leu Gly Val Asp Ser Gly Ala Lys Ile Gly Thr Glu Lys
                        260                 265                 270

Thr Thr Ile Ser Glu Ala Ile Ser Asp Val Lys Gln Ala Leu Thr Asp
                        275                 280                 285

Ala Thr Leu Ala Tyr Lys Ala Asp Asn Lys Asn Gly Lys Thr Val Lys
        290                     295                 300

Leu Thr Asp Gly Leu Asn Phe Thr Ser Thr Thr Asn Ile Asp Ala Ser
        305                     310                 315                 320

Val Glu Asp Asn Gly Val Val Lys Phe Thr Leu Lys Asp Lys Leu Thr
                        325                 330                 335

Gly Leu Lys Thr Ile Ala Thr Glu Ser Leu Asn Ala Ser Gln Asn Ile
                        340                 345                 350

Ile Ala Gly Gly Thr Val Thr Val Gly Gly Glu Thr Gly Ile Val
                        355                 360                 365

Leu Thr Lys Ser Gly Ser Gly Asn Asp Arg Thr Leu Ser Leu Ser Gly
                        370                 375                 380

Ala Gly Asn Ala Ala Thr Asp Gly Ile Lys Val Ser Gly Val Lys Ala
        385                     390                 395                 400

Gly Thr Ala Asp Thr Asp Ala Val Asn Lys Gly Gln Leu Asp Lys Leu
                        405                 410                 415

Phe Lys Ala Ile Asn Asp Ala Leu Gly Thr Thr Asp Leu Ala Val Thr
                        420                 425                 430

Lys Asn Pro Asn Gln Thr Ser Ile Phe Asn Pro Ile Asn Gly Thr Ala
                        435                 440                 445

Pro Thr Thr Phe Lys Asp Ala Val Asp Lys Leu Thr Thr Ala Val Asn
                        450                 455                 460

Thr Gly Trp Gly Ser
        465

<210> SEQ ID NO 51
<211> LENGTH: 268
```

```
<212> TYPE: PRT
<213> ORGANISM: Avibacterium paragallinarum
<220> FEATURE:
<223> OTHER INFORMATION: type

```
Phe Thr Val Gly Leu Met Lys Asp Ile Glu Gly Val Asn Ser Ile Thr
 65                  70                  75                  80

Phe Asp Lys Ser Gly Gln Asp Leu Asn Gln Val Thr Gly Arg Met Ser
                 85                  90                  95

Ser Ala Gly Leu Thr Phe Lys Lys Gly Asp Thr Thr Asn Gly Ser Thr
            100                 105                 110

Thr Thr Phe Ala Glu Asp Gly Leu Thr Ile Asp Ser Thr Thr Asn Ser
        115                 120                 125

Ala Gln Thr Asn Leu Val Lys Val Ser Arg Asp Gly Phe Ser Val Lys
    130                 135                 140

Asn Gly Ser Asp Glu Ser Lys Leu Ala Ser Thr Lys Leu Ser Ile Gly
145                 150                 155                 160

Ala Glu Asn Ala Glu His Val Glu Val Thr Lys Ser Gly Ile Ala Leu
                165                 170                 175

Lys Ala Asp Asn Thr Ser Asp Lys Ser Ser Ile Thr Leu Ala Gln Asp
            180                 185                 190

Ala Ile Thr Leu Ala Gly Asn Ala Thr Gly Thr Ala Ile Lys Leu Thr
        195                 200                 205

Gly Val Ala Asp Gly Asn Ile Thr Val Asn Ser Lys Asp Ala Val Asn
210                 215                 220

Gly Gly Gln Leu Arg Thr Leu Leu Gly Val Asp Ser Gly Ala Lys Ile
225                 230                 235                 240

Gly Gly Thr Glu Lys Thr Thr Ile Ser Glu Ala Ile Ser Asp Val Lys
                245                 250                 255

Gln Ala Leu Thr Asp Ala Thr Leu Ala Tyr Lys Ala Asp Asn Lys Asn
            260                 265                 270

Gly Lys Thr Val Lys Leu Thr Asp Gly Leu Asn Phe Thr Ser Thr Thr
        275                 280                 285

Asn Ile Asp Ala Ser Val Glu Asp Asn Gly Val Val Lys Phe Thr Leu
290                 295                 300

Lys Asp Lys Leu Thr Gly Leu Lys Thr Ile Ala Thr Glu Ser Leu Asn
305                 310                 315                 320

Ala Ser Gln Asn Ile Ile Ala Gly Gly Thr Val Thr Val Gly Gly Glu
                325                 330                 335

Thr Glu Gly Ile Val Leu Thr Lys Ser Gly Ser Gly Asn Asp Arg Thr
            340                 345                 350

Leu Ser Leu Ser Gly Ala Gly Asn Ala Ala Thr Asp Gly Ile Lys Val
        355                 360                 365

Ser Gly Val Lys Ala Gly Thr Ala Asp Thr Asp Ala Val Asn Lys Gly
370                 375                 380

Gln Leu Asp Lys Leu Phe Lys Ala Ile Asn Asp Ala Leu Gly Thr Thr
385                 390                 395                 400

Asp Leu Ala Val Thr Lys Asn Pro Asn Gln Thr Ser Ile Phe Asn Pro
                405                 410                 415

Ile Asn Gly Thr Ala Pro Thr Thr Phe Lys Asp Ala Val Asp Lys Leu
            420                 425                 430

Thr Thr Ala Val Asn Thr Gly Trp Gly Ser Lys Val Gly Ile Leu Ala
        435                 440                 445

Thr Gly Ile Asp Gly Ile Asp Ala Gly Asn Lys Lys Ile Ser Asn Val
450                 455                 460

Ala Asp Gly Asp Ile Ser Pro Thr Ser Asp Val Val Thr Gly Arg
465                 470                 475                 480

Gln Leu Tyr Ala Leu Met Gln Lys Gly Ile Arg Val Tyr Gly Asp Glu
            485                 490                 495
```

Val Ser Pro Thr Lys Thr Gln Thr
            500

<210> SEQ ID NO 53
<211> LENGTH: 442
<212> TYPE: PRT
<213> ORGANISM: Avibacterium paragallinarum
<220> FEATURE:
<223> OTHER INFORMATION: type C

<400> SEQUENCE: 53

Leu Ile Ser Leu Ser Ala Thr Glu Glu Glu Glu Val Val Ser Gly Glu
1 5 10 15

Ala Val Tyr Asp Ala Leu Lys Gly Ala Lys Pro Thr Val Ser Ala Glu
20 25 30

Ala Asn Lys Gly Ile Thr Gly Leu Val Asp Val Val Lys Lys Ala Asn
35 40 45

Ser Pro Ile Thr Val Glu Pro Ser Thr Asp Asn Asn Lys Lys Lys Thr
50 55 60

Phe Thr Val Gly Leu Met Lys Asp Ile Glu Gly Val Asn Ser Ile Thr
65 70 75 80

Phe Asp Lys Ser Gly Gln Asp Leu Asn Gln Val Thr Gly Arg Met Ser
85 90 95

Ser Ala Gly Leu Thr Phe Lys Lys Gly Asp Thr Thr Asn Gly Ser Thr
100 105 110

Thr Thr Phe Ala Glu Asp Gly Leu Thr Ile Asp Ser Thr Thr Asn Ser
115 120 125

Ala Gln Thr Asn Leu Val Lys Val Ser Arg Asp Gly Phe Ser Val Lys
130 135 140

Asn Gly Ser Asp Glu Ser Lys Leu Ala Ser Thr Lys Leu Ser Ile Gly
145 150 155 160

Ala Glu Asn Ala Glu His Val Glu Val Thr Lys Ser Gly Ile Ala Leu
165 170 175

Lys Ala Asp Asn Thr Ser Asp Lys Ser Ser Ile Thr Leu Ala Gln Asp
180 185 190

Ala Ile Thr Leu Ala Gly Asn Ala Thr Gly Thr Ala Ile Lys Leu Thr
195 200 205

Gly Val Ala Asp Gly Asn Ile Thr Val Asn Ser Lys Asp Ala Val Asn
210 215 220

Gly Gly Gln Leu Arg Thr Leu Leu Gly Val Asp Ser Gly Ala Lys Ile
225 230 235 240

Gly Gly Thr Glu Lys Thr Thr Ile Ser Glu Ala Ile Ser Asp Val Lys
245 250 255

Gln Ala Leu Thr Asp Ala Thr Leu Ala Tyr Lys Ala Asp Asn Lys Asn
260 265 270

Gly Lys Thr Val Lys Leu Thr Asp Gly Leu Asn Phe Thr Ser Thr Thr
275 280 285

Asn Ile Asp Ala Ser Val Glu Asp Asn Gly Val Val Lys Phe Thr Leu
290 295 300

Lys Asp Lys Leu Thr Gly Leu Lys Thr Ile Ala Thr Glu Ser Leu Asn
305 310 315 320

Ala Ser Gln Asn Ile Ile Ala Gly Gly Thr Val Thr Val Gly Gly Glu
325 330 335

Thr Glu Gly Ile Val Leu Thr Lys Ser Gly Ser Gly Asn Asp Arg Thr
340 345 350

```
Leu Ser Leu Ser Gly Ala Gly Asn Ala Ala Thr Asp Gly Ile Lys Val
        355                 360                 365

Ser Gly Val Lys Ala Gly Thr Ala Asp Thr Asp Ala Val Asn Lys Gly
370                 375                 380

Gln Leu Asp Lys Leu Phe Lys Ala Ile Asn Asp Ala Leu Gly Thr Thr
385                 390                 395                 400

Asp Leu Ala Val Thr Lys Asn Pro Asn Gln Thr Ser Ile Phe Asn Pro
                405                 410                 415

Ile Asn Gly Thr Ala Pro Thr Thr Phe Lys Asp Ala Val Asp Lys Leu
                420                 425                 430

Thr Thr Ala Val Asn Thr Gly Trp Gly Ser
                435                 440

<210> SEQ ID NO 54
<211> LENGTH: 241
<212> TYPE: PRT
<213> ORGANISM: Avibacterium paragallinarum
<220> FEATURE:
<223> OTHER INFORMATION: type C

<400> SEQUENCE: 54

Leu Ile Ser Leu Ser Ala Thr Glu Glu Glu Val Val Ser Gly Glu
1               5                   10                  15

Ala Val Tyr Asp Ala Leu Lys Gly Ala Lys Pro Thr Val Ser Ala Glu
                20                  25                  30

Ala Asn Lys Gly Ile Thr Gly Leu Val Asp Val Val Lys Lys Ala Asn
                35                  40                  45

Ser Pro Ile Thr Val Glu Pro Ser Thr Asp Asn Lys Lys Lys Thr
50                  55                  60

Phe Thr Val Gly Leu Met Lys Asp Ile Glu Gly Val Asn Ser Ile Thr
65                  70                  75                  80

Phe Asp Lys Ser Gly Gln Asp Leu Asn Gln Val Thr Gly Arg Met Ser
                85                  90                  95

Ser Ala Gly Leu Thr Phe Lys Lys Gly Asp Thr Thr Asn Gly Ser Thr
                100                 105                 110

Thr Thr Phe Ala Glu Asp Gly Leu Thr Ile Asp Ser Thr Thr Asn Ser
                115                 120                 125

Ala Gln Thr Asn Leu Val Lys Val Ser Arg Asp Gly Phe Ser Val Lys
                130                 135                 140

Asn Gly Ser Asp Glu Ser Lys Leu Ala Ser Thr Lys Leu Ser Ile Gly
145                 150                 155                 160

Ala Glu Asn Ala Glu His Val Glu Val Thr Lys Ser Gly Ile Ala Leu
                165                 170                 175

Lys Ala Asp Asn Thr Ser Asp Lys Ser Ser Ile Thr Leu Ala Gln Asp
                180                 185                 190

Ala Ile Thr Leu Ala Gly Asn Ala Thr Gly Thr Ala Ile Lys Leu Thr
                195                 200                 205

Gly Val Ala Asp Gly Asn Ile Thr Val Asn Ser Lys Asp Ala Val Asn
                210                 215                 220

Gly Gly Gln Leu Arg Thr Leu Leu Gly Val Asp Ser Gly Ala Lys Ile
225                 230                 235                 240

Gly

<210> SEQ ID NO 55
<211> LENGTH: 375
<212> TYPE: PRT
<213> ORGANISM: Avibacterium paragallinarum
```

<220> FEATURE:
<223> OTHER INFORMATION: type C

<400> SEQUENCE: 55

```
Gly Leu Met Lys Asp Ile Glu Gly Val Asn Ser Ile Thr Phe Asp Lys
1               5                   10                  15

Ser Gly Gln Asp Leu Asn Gln Val Thr Gly Arg Met Ser Ser Ala Gly
            20                  25                  30

Leu Thr Phe Lys Lys Gly Asp Thr Thr Asn Gly Ser Thr Thr Thr Phe
        35                  40                  45

Ala Glu Asp Gly Leu Thr Ile Asp Ser Thr Thr Asn Ser Ala Gln Thr
    50                  55                  60

Asn Leu Val Lys Val Ser Arg Asp Gly Phe Ser Val Lys Asn Gly Ser
65                  70                  75                  80

Asp Glu Ser Lys Leu Ala Ser Thr Lys Leu Ser Ile Gly Ala Glu Asn
                85                  90                  95

Ala Glu His Val Glu Val Thr Lys Ser Gly Ile Ala Leu Lys Ala Asp
            100                 105                 110

Asn Thr Ser Asp Lys Ser Ser Ile Thr Leu Ala Gln Asp Ala Ile Thr
        115                 120                 125

Leu Ala Gly Asn Ala Thr Gly Thr Ala Ile Lys Leu Thr Gly Val Ala
    130                 135                 140

Asp Gly Asn Ile Thr Val Asn Ser Lys Asp Ala Val Asn Gly Gly Gln
145                 150                 155                 160

Leu Arg Thr Leu Leu Gly Val Asp Ser Gly Ala Lys Ile Gly Gly Thr
                165                 170                 175

Glu Lys Thr Thr Ile Ser Glu Ala Ile Ser Asp Val Lys Gln Ala Leu
            180                 185                 190

Thr Asp Ala Thr Leu Ala Tyr Lys Ala Asp Asn Lys Asn Gly Lys Thr
        195                 200                 205

Val Lys Leu Thr Asp Gly Leu Asn Phe Thr Ser Thr Asn Ile Asp
    210                 215                 220

Ala Ser Val Glu Asp Asn Gly Val Val Lys Phe Thr Leu Lys Asp Lys
225                 230                 235                 240

Leu Thr Gly Leu Lys Thr Ile Ala Thr Glu Ser Leu Asn Ala Ser Gln
                245                 250                 255

Asn Ile Ile Ala Gly Gly Thr Val Thr Val Gly Gly Glu Thr Glu Gly
            260                 265                 270

Ile Val Leu Thr Lys Ser Gly Ser Gly Asn Asp Arg Thr Leu Ser Leu
        275                 280                 285

Ser Gly Ala Gly Asn Ala Ala Thr Asp Gly Ile Lys Val Ser Gly Val
    290                 295                 300

Lys Ala Gly Thr Ala Asp Thr Asp Ala Val Asn Lys Gly Gln Leu Asp
305                 310                 315                 320

Lys Leu Phe Lys Ala Ile Asn Asp Ala Leu Gly Thr Thr Asp Leu Ala
                325                 330                 335

Val Thr Lys Asn Pro Asn Gln Thr Ser Ile Phe Asn Pro Ile Asn Gly
            340                 345                 350

Thr Ala Pro Thr Thr Phe Lys Asp Ala Val Asp Lys Leu Thr Thr Ala
        355                 360                 365

Val Asn Thr Gly Trp Gly Ser
    370                 375
```

<210> SEQ ID NO 56
<211> LENGTH: 174

```
<212> TYPE: PRT
<213> ORGANISM: Avibacterium paragallinarum
<220> FEATURE:
<223> OTHER INFORMATION: type C

<400> SEQUENCE: 56

Gly Leu Met Lys Asp Ile Glu Gly Val Asn Ser Ile Thr Phe Asp Lys
1               5                   10                  15

Ser Gly Gln Asp Leu Asn Gln Val Thr Gly Arg Met Ser Ser Ala Gly
            20                  25                  30

Leu Thr Phe Lys Lys Gly Asp Thr Thr Asn Gly Ser Thr Thr Thr Phe
        35                  40                  45

Ala Glu Asp Gly Leu Thr Ile Asp Ser Thr Thr Asn Ser Ala Gln Thr
    50                  55                  60

Asn Leu Val Lys Val Ser Arg Asp Gly Phe Ser Val Lys Asn Gly Ser
65                  70                  75                  80

Asp Glu Ser Lys Leu Ala Ser Thr Lys Leu Ser Ile Gly Ala Glu Asn
                85                  90                  95

Ala Glu His Val Glu Val Thr Lys Ser Gly Ile Ala Leu Lys Ala Asp
            100                 105                 110

Asn Thr Ser Asp Lys Ser Ser Ile Thr Leu Ala Gln Asp Ala Ile Thr
        115                 120                 125

Leu Ala Gly Asn Ala Thr Gly Thr Ala Ile Lys Leu Thr Gly Val Ala
    130                 135                 140

Asp Gly Asn Ile Thr Val Asn Ser Lys Asp Ala Val Asn Gly Gly Gln
145                 150                 155                 160

Leu Arg Thr Leu Leu Gly Val Asp Ser Gly Ala Lys Ile Gly
                165                 170

<210> SEQ ID NO 57
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: A 5'primer for the amplification of the DNA
      fragment from Avibacterium paragallinarum type C

<400> SEQUENCE: 57
cgcggatcct tgatctcgct ttcggcaaca ga                              32

<210> SEQ ID NO 58
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: A 3'primer for the amplification of the DNA
      fragment from Avibacterium paragallinarum type C

<400> SEQUENCE: 58
cgcggatccc tatgatcccc aacctgtatt cac                             33

<210> SEQ ID NO 59
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
```

```
<220> FEATURE:
<223> OTHER INFORMATION: A 3'primer for the amplification of the DNA
      fragment from Avibacterium paragallinarum type C

<400> SEQUENCE: 59
cgcggatccc tagccaattt tagccccgct atc                                     33

<210> SEQ ID NO 60
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: A 3'primer for the amplification of the DNA
      fragment from Avibacterium paragallinarum type C

<400> SEQUENCE: 60
cgcggatccc tatgtttgag tcttcgttgg act                                     33

<210> SEQ ID NO 61
<211> LENGTH: 1017
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: A fusion peptide consisting of membrane protein
      sections from each of Avibacterium paragallinarum types A and C

<400> SEQUENCE: 61
```

Met Asp Gly Thr Ile Thr Phe Thr Asn Ile Gly Gly Thr Gly Gln Ala
1               5                   10                  15

Thr Ile His Asp Ala Ile Asn Asn Val Leu Thr Lys Gly Ile Tyr Leu
            20                  25                  30

Lys Ala Asp Gln Asn Asp Pro Thr Gly Asn Gln Gly Gln Lys Val Glu
        35                  40                  45

Leu Gly Asn Ala Ile Thr Leu Ser Ala Thr Asn Gln Trp Ala Asn Asn
    50                  55                  60

Gly Val Asn Tyr Lys Thr Asn Asn Leu Thr Thr Tyr Asn Ser Gln Asn
65                  70                  75                  80

Gly Thr Ile Leu Phe Gly Met Arg Glu Asp Pro Ser Val Lys Gln Ile
                85                  90                  95

Thr Ala Gly Thr Tyr Asn Thr Thr Gly Asp Ala Asn Asn Lys Asn Gln
            100                 105                 110

Leu Asn Asn Thr Leu Gln Gln Thr Thr Leu Glu Ala Thr Gly Ile Thr
        115                 120                 125

Ser Ser Val Gly Ser Thr Asn Tyr Ala Gly Phe Ser Leu Gly Ala Asp
    130                 135                 140

Ser Val Thr Phe Ser Lys Gly Gly Ala Gly Thr Val Lys Leu Ser Gly
145                 150                 155                 160

Val Ser Asp Ala Thr Ala Asp Thr Asp Ala Ala Thr Leu Lys Gln Val
                165                 170                 175

Lys Glu Tyr Arg Thr Thr Leu Val Gly Asp Asn Asp Ile Thr Ala Ala
            180                 185                 190

Asp Arg Ser Gly Gly Thr Ser Asn Gly Ile Thr Tyr Asn Leu Ser Leu
        195                 200                 205

Asn Lys Gly Thr Val Ser Ala Thr Glu Glu Lys Val Val Ser Gly Lys
    210                 215                 220

-continued

```
Thr Val Tyr Glu Ala Ile Arg Asn Ala Ile Thr Gly Asn Ile Phe Thr
225                 230                 235                 240

Ile Gly Leu Asp Asp Thr Thr Leu Asn Lys Ile Asn Asn Pro Ala Asp
            245                 250                 255

Gln Asp Leu Ser Asn Leu Ser Glu Ser Gly Lys Asn Ala Ile Thr Gly
        260                 265                 270

Leu Val Asp Val Val Lys Lys Thr Asn Ser Pro Ile Thr Val Glu Pro
    275                 280                 285

Ser Thr Asp Ser Asn Lys Lys Lys Thr Phe Thr Val Gly Val Asp Phe
290                 295                 300

Thr Asp Thr Ile Thr Glu Gly Asp Ala Thr Asp Asp Lys Lys Leu Thr
305                 310                 315                 320

Thr Ser Lys Ser Val Glu Ser Tyr Val Thr Asn Lys Leu Ala Asn Phe
            325                 330                 335

Ser Thr Asp Ile Leu Leu Ser Asp Gly Arg Ser Gly Asn Ala Thr Thr
        340                 345                 350

Ala Asn Asp Gly Val Gly Lys Arg Arg Leu Ser Asp Gly Phe Thr Ile
    355                 360                 365

Lys Ser Glu Asn Phe Thr Leu Gly Ser Lys Gln Tyr Asn Gly Ser Asp
370                 375                 380

Ser Leu Gly Val Met Tyr Asp Asp Gln Asn Gly Val Phe Lys Leu Ser
385                 390                 395                 400

Leu Asn Met Thr Ala Leu Thr Thr Ser Leu Ala Asn Thr Phe Ala Lys
            405                 410                 415

Leu Asp Ala Ser Asn Leu Thr Asp Ser Asn Lys Glu Lys Trp Arg
        420                 425                 430

Thr Ala Leu Asn Val Tyr Ser Lys Thr Glu Val Asp Ala Glu Ile Gln
    435                 440                 445

Lys Ser Lys Val Thr Leu Thr Pro Asp Ser Gly Leu Ile Phe Ala Thr
450                 455                 460

Lys Gln Ala Gly Ser Gly Asn Asn Ala Gly Ile Asp Ala Gly Asn Lys
465                 470                 475                 480

Lys Ile Ser Asn Val Ala Asp Gly Asp Ile Ser Pro Thr Ser Gly Asp
            485                 490                 495

Val Val Thr Gly Arg Gln Leu Tyr Ala Leu Met Gln Lys Gly Ile Arg
        500                 505                 510

Val Tyr Gly Asp Glu Val Ser Pro Thr Lys Thr Gln Thr Thr Ala Pro
    515                 520                 525

Thr Asn Ala Asn Pro Thr Ala Thr Thr Ala Pro Thr Ala Ser Ser Thr
530                 535                 540

Gln Gly Gly Ser Asp Gly Thr Ile Thr Phe Thr Asn Ile Gly Gly Thr
545                 550                 555                 560

Gly Gln Asp Thr Ile His Asp Ala Ile Asn Asn Val Leu Thr Lys Leu
            565                 570                 575

Ile Ser Leu Ser Ala Thr Glu Glu Glu Val Val Ser Gly Glu Ala
        580                 585                 590

Val Tyr Asp Ala Leu Lys Gly Ala Lys Pro Thr Val Ser Ala Glu Ala
    595                 600                 605

Asn Lys Gly Ile Thr Gly Leu Val Asp Val Val Lys Lys Ala Asn Ser
610                 615                 620

Pro Ile Thr Val Glu Pro Ser Thr Asp Asn Asn Lys Lys Lys Thr Phe
625                 630                 635                 640

Thr Val Gly Leu Met Lys Asp Ile Glu Gly Val Asn Ser Ile Thr Phe
            645                 650                 655
```

Asp Lys Ser Gly Gln Asp Leu Asn Gln Val Thr Gly Arg Met Ser Ser
                660                 665                 670

Ala Gly Leu Thr Phe Lys Lys Gly Asp Thr Thr Asn Gly Ser Thr Thr
            675                 680                 685

Thr Phe Ala Glu Asp Gly Leu Thr Ile Asp Ser Thr Thr Asn Ser Ala
690                 695                 700

Gln Thr Asn Leu Val Lys Val Ser Arg Asp Gly Phe Ser Val Lys Asn
705                 710                 715                 720

Gly Ser Asp Glu Ser Lys Leu Ala Ser Thr Lys Leu Ser Ile Gly Ala
                725                 730                 735

Glu Asn Ala Glu His Val Glu Val Thr Lys Ser Gly Ile Ala Leu Lys
            740                 745                 750

Ala Asp Asn Thr Ser Asp Lys Ser Ser Ile Thr Leu Ala Gln Asp Ala
        755                 760                 765

Ile Thr Leu Ala Gly Asn Ala Thr Gly Thr Ala Ile Lys Leu Thr Gly
770                 775                 780

Val Ala Asp Gly Asn Ile Thr Val Asn Ser Lys Asp Ala Val Asn Gly
785                 790                 795                 800

Gly Gln Leu Arg Thr Leu Leu Gly Val Asp Ser Gly Ala Lys Ile Gly
                805                 810                 815

Gly Thr Glu Lys Thr Thr Ile Ser Glu Ala Ile Ser Asp Val Lys Gln
            820                 825                 830

Ala Leu Thr Asp Ala Thr Leu Ala Tyr Lys Ala Asp Asn Lys Asn Gly
        835                 840                 845

Lys Thr Val Lys Leu Thr Asp Gly Leu Asn Phe Thr Ser Thr Thr Asn
850                 855                 860

Ile Asp Ala Ser Val Glu Asp Asn Gly Val Val Lys Phe Thr Leu Lys
865                 870                 875                 880

Asp Lys Leu Thr Gly Leu Lys Thr Ile Ala Thr Glu Ser Leu Asn Ala
                885                 890                 895

Ser Gln Asn Ile Ile Ala Gly Gly Thr Val Thr Val Gly Gly Glu Thr
            900                 905                 910

Glu Gly Ile Val Leu Thr Lys Ser Gly Ser Gly Asn Asp Arg Thr Leu
        915                 920                 925

Ser Leu Ser Gly Ala Gly Asn Ala Ala Thr Asp Gly Ile Lys Val Ser
930                 935                 940

Gly Val Lys Ala Gly Thr Ala Asp Thr Asp Ala Val Asn Lys Gly Gln
945                 950                 955                 960

Leu Asp Lys Leu Phe Lys Ala Ile Asn Asp Ala Leu Gly Thr Thr Asp
                965                 970                 975

Leu Ala Val Thr Lys Asn Pro Asn Gln Thr Ser Ile Phe Asn Pro Ile
            980                 985                 990

Asn Gly Thr Ala Pro Thr Thr Phe Lys Asp Ala Val Asp Lys Leu Thr
        995                 1000                1005

Thr Ala Val Asn Thr Gly Trp Gly Ser
        1010                1015

<210> SEQ ID NO 62
<211> LENGTH: 816
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: A fusion peptide consisting of membrane protein sections from each of Avibacterium paragallinarum types A and C

<400> SEQUENCE: 62

```
Met Asp Gly Thr Ile Thr Phe Thr Asn Ile Gly Thr Gly Gln Ala
1               5                   10                  15

Thr Ile His Asp Ala Ile Asn Asn Val Leu Thr Lys Gly Ile Tyr Leu
            20                  25                  30

Lys Ala Asp Gln Asn Asp Pro Thr Gly Asn Gln Gly Gln Lys Val Glu
            35                  40                  45

Leu Gly Asn Ala Ile Thr Leu Ser Ala Thr Asn Gln Trp Ala Asn Asn
    50                  55                  60

Gly Val Asn Tyr Lys Thr Asn Asn Leu Thr Thr Tyr Asn Ser Gln Asn
65                  70                  75                  80

Gly Thr Ile Leu Phe Gly Met Arg Glu Asp Pro Ser Val Lys Gln Ile
                85                  90                  95

Thr Ala Gly Thr Tyr Asn Thr Thr Gly Asp Ala Asn Asn Lys Asn Gln
            100                 105                 110

Leu Asn Asn Thr Leu Gln Gln Thr Leu Glu Ala Thr Gly Ile Thr
            115                 120                 125

Ser Ser Val Gly Ser Thr Asn Tyr Ala Gly Phe Ser Leu Gly Ala Asp
    130                 135                 140

Ser Val Thr Phe Ser Lys Gly Ala Gly Thr Val Lys Leu Ser Gly
145                 150                 155                 160

Val Ser Asp Ala Thr Ala Asp Thr Asp Ala Ala Thr Leu Lys Gln Val
                165                 170                 175

Lys Glu Tyr Arg Thr Thr Leu Val Gly Asp Asn Asp Ile Thr Ala Ala
            180                 185                 190

Asp Arg Ser Gly Gly Thr Ser Asn Gly Ile Thr Tyr Asn Leu Ser Leu
        195                 200                 205

Asn Lys Gly Thr Val Ser Ala Thr Glu Glu Lys Val Val Ser Gly Lys
    210                 215                 220

Thr Val Tyr Glu Ala Ile Arg Asn Ala Ile Thr Gly Asn Ile Phe Thr
225                 230                 235                 240

Ile Gly Leu Asp Asp Thr Thr Leu Asn Lys Ile Asn Asn Pro Ala Asp
                245                 250                 255

Gln Asp Leu Ser Asn Leu Ser Glu Ser Gly Lys Asn Ala Ile Thr Gly
            260                 265                 270

Leu Val Asp Val Val Lys Lys Thr Asn Ser Pro Ile Thr Val Glu Pro
        275                 280                 285

Ser Thr Asp Ser Asn Lys Lys Lys Thr Phe Thr Val Gly Val Asp Phe
    290                 295                 300

Thr Asp Thr Ile Thr Glu Gly Asp Ala Thr Asp Lys Lys Leu Thr
305                 310                 315                 320

Thr Ser Lys Ser Val Glu Ser Tyr Val Thr Asn Lys Leu Ala Asn Phe
                325                 330                 335

Ser Thr Asp Ile Leu Leu Ser Asp Gly Arg Ser Gly Asn Ala Thr Thr
            340                 345                 350

Ala Asn Asp Gly Val Gly Lys Arg Arg Leu Ser Asp Gly Phe Thr Ile
        355                 360                 365

Lys Ser Glu Asn Phe Thr Leu Gly Ser Lys Gln Tyr Asn Gly Ser Asp
    370                 375                 380

Ser Leu Gly Val Met Tyr Asp Asp Gln Asn Gly Val Phe Lys Leu Ser
385                 390                 395                 400

Leu Asn Met Thr Ala Leu Thr Thr Ser Leu Ala Asn Thr Phe Ala Lys
```

```
                405                 410                 415
Leu Asp Ala Ser Asn Leu Thr Asp Asp Ser Asn Lys Glu Lys Trp Arg
            420                 425                 430

Thr Ala Leu Asn Val Tyr Ser Lys Thr Glu Val Asp Ala Glu Ile Gln
        435                 440                 445

Lys Ser Lys Val Thr Leu Thr Pro Asp Ser Gly Leu Ile Phe Ala Thr
    450                 455                 460

Lys Gln Ala Gly Ser Gly Asn Asn Ala Gly Ile Asp Ala Gly Asn Lys
465                 470                 475                 480

Lys Ile Ser Asn Val Ala Asp Gly Asp Ile Ser Pro Thr Ser Gly Asp
                485                 490                 495

Val Val Thr Gly Arg Gln Leu Tyr Ala Leu Met Gln Lys Gly Ile Arg
            500                 505                 510

Val Tyr Gly Asp Glu Val Ser Pro Thr Lys Thr Gln Thr Thr Ala Pro
        515                 520                 525

Thr Asn Ala Asn Pro Thr Ala Thr Thr Ala Pro Thr Ala Ser Ser Thr
    530                 535                 540

Gln Gly Gly Ser Asp Gly Thr Ile Thr Phe Thr Asn Ile Gly Gly Thr
545                 550                 555                 560

Gly Gln Asp Thr Ile His Asp Ala Ile Asn Asn Val Leu Thr Lys Leu
                565                 570                 575

Ile Ser Leu Ser Ala Thr Glu Glu Glu Val Val Ser Gly Glu Ala
            580                 585                 590

Val Tyr Asp Ala Leu Lys Gly Ala Lys Pro Thr Val Ser Ala Glu Ala
        595                 600                 605

Asn Lys Gly Ile Thr Gly Leu Val Asp Val Val Lys Lys Ala Asn Ser
    610                 615                 620

Pro Ile Thr Val Glu Pro Ser Thr Asp Asn Asn Lys Lys Lys Thr Phe
625                 630                 635                 640

Thr Val Gly Leu Met Lys Asp Ile Glu Gly Val Asn Ser Ile Thr Phe
                645                 650                 655

Asp Lys Ser Gly Gln Asp Leu Asn Gln Val Thr Gly Arg Met Ser Ser
            660                 665                 670

Ala Gly Leu Thr Phe Lys Lys Gly Asp Thr Thr Asn Gly Ser Thr Thr
        675                 680                 685

Thr Phe Ala Glu Asp Gly Leu Thr Ile Asp Ser Thr Thr Asn Ser Ala
    690                 695                 700

Gln Thr Asn Leu Val Lys Val Ser Arg Asp Gly Phe Ser Val Lys Asn
705                 710                 715                 720

Gly Ser Asp Glu Ser Lys Leu Ala Ser Thr Lys Leu Ser Ile Gly Ala
                725                 730                 735

Glu Asn Ala Glu His Val Glu Val Thr Lys Ser Gly Ile Ala Leu Lys
            740                 745                 750

Ala Asp Asn Thr Ser Asp Lys Ser Ser Ile Thr Leu Ala Gln Asp Ala
        755                 760                 765

Ile Thr Leu Ala Gly Asn Ala Thr Gly Thr Ala Ile Lys Leu Thr Gly
    770                 775                 780

Val Ala Asp Gly Asn Ile Thr Val Asn Ser Lys Asp Ala Val Asn Gly
785                 790                 795                 800

Gly Gln Leu Arg Thr Leu Leu Gly Val Asp Ser Gly Ala Lys Ile Gly
                805                 810                 815

<210> SEQ ID NO 63
<211> LENGTH: 1052
```

<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: A fusion peptide consisting of membrane protein sections from each of Avibacterium paragallinarum types A and C

<400> SEQUENCE: 63

```
Met Asp Gly Thr Ile Thr Phe Thr Asn Ile Gly Gly Thr Gly Gln Ala
1               5                   10                  15

Thr Ile His Asp Ala Ile Asn Asn Val Leu Thr Lys Gly Ile Tyr Leu
            20                  25                  30

Lys Ala Asp Gln Asn Asp Pro Thr Gly Asn Gln Gly Gln Lys Val Glu
        35                  40                  45

Leu Gly Asn Ala Ile Thr Leu Ser Ala Thr Asn Gln Trp Ala Asn Asn
    50                  55                  60

Gly Val Asn Tyr Lys Thr Asn Asn Leu Thr Thr Tyr Asn Ser Gln Asn
65                  70                  75                  80

Gly Thr Ile Leu Phe Gly Met Arg Glu Asp Pro Ser Val Lys Gln Ile
                85                  90                  95

Thr Ala Gly Thr Tyr Asn Thr Thr Gly Asp Ala Asn Asn Lys Asn Gln
            100                 105                 110

Leu Asn Asn Thr Leu Gln Gln Thr Thr Leu Glu Ala Thr Gly Ile Thr
        115                 120                 125

Ser Ser Val Gly Ser Thr Asn Tyr Ala Gly Phe Ser Leu Gly Ala Asp
    130                 135                 140

Ser Val Thr Phe Ser Lys Gly Ala Gly Thr Val Lys Leu Ser Gly
145                 150                 155                 160

Val Ser Asp Ala Thr Ala Asp Thr Asp Ala Ala Thr Leu Lys Gln Val
                165                 170                 175

Lys Glu Tyr Arg Thr Thr Leu Val Gly Asp Asn Asp Ile Thr Ala Ala
            180                 185                 190

Asp Arg Ser Gly Gly Thr Ser Asn Gly Ile Thr Tyr Asn Leu Ser Leu
        195                 200                 205

Asn Lys Gly Thr Val Ser Ala Thr Glu Glu Lys Val Val Ser Gly Lys
    210                 215                 220

Thr Val Tyr Glu Ala Ile Arg Asn Ala Ile Thr Gly Asn Ile Phe Thr
225                 230                 235                 240

Ile Gly Leu Asp Asp Thr Thr Leu Asn Lys Ile Asn Asn Pro Ala Asp
                245                 250                 255

Gln Asp Leu Ser Asn Leu Ser Glu Ser Gly Lys Asn Ala Ile Thr Gly
            260                 265                 270

Leu Val Asp Val Val Lys Lys Thr Asn Ser Pro Ile Thr Val Glu Pro
        275                 280                 285

Ser Thr Asp Ser Asn Lys Lys Lys Thr Phe Thr Val Gly Val Asp Phe
    290                 295                 300

Thr Asp Thr Ile Thr Glu Gly Asp Ala Thr Asp Lys Lys Leu Thr
305                 310                 315                 320

Thr Ser Lys Ser Val Glu Ser Tyr Val Thr Asn Lys Leu Ala Asn Phe
                325                 330                 335

Ser Thr Asp Ile Leu Leu Ser Asp Gly Arg Ser Gly Asn Ala Thr Thr
            340                 345                 350

Ala Asn Asp Gly Val Gly Lys Arg Arg Leu Ser Asp Gly Phe Thr Ile
        355                 360                 365
```

```
Lys Ser Glu Asn Phe Thr Leu Gly Ser Lys Gln Tyr Asn Gly Ser Asp
        370                 375                 380

Ser Leu Gly Val Met Tyr Asp Asp Gln Asn Gly Val Phe Lys Leu Ser
385                 390                 395                 400

Leu Asn Met Thr Ala Leu Thr Thr Ser Leu Ala Asn Thr Phe Ala Lys
                405                 410                 415

Leu Asp Ala Ser Asn Leu Thr Asp Asp Ser Asn Lys Glu Lys Trp Arg
            420                 425                 430

Thr Ala Leu Asn Val Tyr Ser Lys Thr Glu Val Asp Ala Glu Ile Gln
                435                 440                 445

Lys Ser Lys Val Thr Leu Thr Pro Asp Ser Gly Leu Ile Phe Ala Thr
450                 455                 460

Lys Gln Ala Gly Ser Gly Asn Asn Ala Gly Ile Asp Ala Gly Asn Lys
465                 470                 475                 480

Lys Ile Ser Asn Val Ala Asp Gly Asp Ile Ser Pro Thr Ser Gly Asp
                485                 490                 495

Val Val Thr Gly Arg Gln Leu Tyr Ala Leu Met Gln Lys Gly Ile Arg
                500                 505                 510

Val Tyr Gly Asp Glu Val Ser Pro Thr Lys Thr Gln Thr Thr Ala Pro
            515                 520                 525

Thr Asn Ala Asn Pro Thr Ala Thr Thr Ala Pro Thr Ala Ser Ser Thr
        530                 535                 540

Gln Gly Gly Ser Leu Ile Ser Leu Ser Ala Thr Glu Glu Glu Glu Val
545                 550                 555                 560

Val Ser Gly Glu Ala Val Tyr Asp Ala Leu Lys Gly Ala Lys Pro Thr
                565                 570                 575

Val Ser Ala Glu Ala Asn Lys Gly Ile Thr Gly Leu Val Asp Val Val
            580                 585                 590

Lys Lys Ala Asn Ser Pro Ile Thr Val Glu Pro Ser Thr Asp Asn Asn
            595                 600                 605

Lys Lys Lys Thr Phe Thr Val Gly Leu Met Lys Asp Ile Glu Gly Val
        610                 615                 620

Asn Ser Ile Thr Phe Asp Lys Ser Gly Gln Asp Leu Asn Gln Val Thr
625                 630                 635                 640

Gly Arg Met Ser Ser Ala Gly Leu Thr Phe Lys Lys Gly Asp Thr Thr
                645                 650                 655

Asn Gly Ser Thr Thr Thr Phe Ala Glu Asp Gly Leu Thr Ile Asp Ser
            660                 665                 670

Thr Thr Asn Ser Ala Gln Thr Asn Leu Val Lys Val Ser Arg Asp Gly
                675                 680                 685

Phe Ser Val Lys Asn Gly Ser Asp Glu Ser Lys Leu Ala Ser Thr Lys
        690                 695                 700

Leu Ser Ile Gly Ala Glu Asn Ala Glu His Val Glu Val Thr Lys Ser
705                 710                 715                 720

Gly Ile Ala Leu Lys Ala Asp Asn Thr Ser Asp Lys Ser Ser Ile Thr
                725                 730                 735

Leu Ala Gln Asp Ala Ile Thr Leu Ala Gly Asn Ala Gly Thr Ala
            740                 745                 750

Ile Lys Leu Thr Gly Val Ala Asp Gly Asn Ile Thr Val Asn Ser Lys
        755                 760                 765

Asp Ala Val Asn Gly Gln Leu Arg Thr Leu Leu Gly Val Asp Ser
770                 775                 780

Gly Ala Lys Ile Gly Gly Thr Glu Lys Thr Thr Ile Ser Glu Ala Ile
785                 790                 795                 800
```

```
Ser Asp Val Lys Gln Ala Leu Thr Asp Ala Thr Leu Ala Tyr Lys Ala
                805                 810                 815

Asp Asn Lys Asn Gly Lys Thr Val Lys Leu Thr Asp Gly Leu Asn Phe
            820                 825                 830

Thr Ser Thr Thr Asn Ile Asp Ala Ser Val Glu Asp Asn Gly Val Val
                835                 840                 845

Lys Phe Thr Leu Lys Asp Lys Leu Thr Gly Leu Lys Thr Ile Ala Thr
    850                 855                 860

Glu Ser Leu Asn Ala Ser Gln Asn Ile Ile Ala Gly Thr Val Thr
865                 870                 875                 880

Val Gly Gly Glu Thr Glu Gly Ile Val Leu Thr Lys Ser Gly Ser Gly
                885                 890                 895

Asn Asp Arg Thr Leu Ser Leu Ser Gly Ala Gly Asn Ala Ala Thr Asp
                900                 905                 910

Gly Ile Lys Val Ser Gly Val Lys Ala Gly Thr Ala Asp Thr Asp Ala
            915                 920                 925

Val Asn Lys Gly Gln Leu Asp Lys Leu Phe Lys Ala Ile Asn Asp Ala
    930                 935                 940

Leu Gly Thr Thr Asp Leu Ala Val Thr Lys Asn Pro Asn Gln Thr Ser
945                 950                 955                 960

Ile Phe Asn Pro Ile Asn Gly Thr Ala Pro Thr Thr Phe Lys Asp Ala
                965                 970                 975

Val Asp Lys Leu Thr Thr Ala Val Asn Thr Gly Trp Gly Ser Lys Val
            980                 985                 990

Gly Ile Leu Ala Thr Gly Ile Asp  Gly Ile Asp Ala Gly  Asn Lys Lys
        995                 1000                1005

Ile Ser  Asn Val Ala Asp Gly  Asp Ile Ser Pro Thr  Ser Gly Asp
        1010                1015                1020

Val Val  Thr Gly Arg Gln Leu  Tyr Ala Leu Met Gln  Lys Gly Ile
1025                1030                1035

Arg Val  Tyr Gly Asp Glu Val  Ser Pro Thr Lys Thr  Gln Thr
1040                1045                1050

<210> SEQ ID NO 64
<211> LENGTH: 990
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: A fusion peptide consisting of membrane protein
      sections from each of Avibacterium paragallinarum types A and C

<400> SEQUENCE: 64

Met Asp Gly Thr Ile Thr Phe Thr Asn Ile Gly Gly Thr Gly Gln Ala
1               5                   10                  15

Thr Ile His Asp Ala Ile Asn Asn Val Leu Thr Lys Gly Ile Tyr Leu
                20                  25                  30

Lys Ala Asp Gln Asn Asp Pro Thr Gly Asn Gly Gln Lys Val Glu
        35                  40                  45

Leu Gly Asn Ala Ile Thr Leu Ser Ala Thr Asn Gln Trp Ala Asn Asn
    50                  55                  60

Gly Val Asn Tyr Lys Thr Asn Asn Leu Thr Thr Tyr Asn Ser Gln Asn
65                  70                  75                  80

Gly Thr Ile Leu Phe Gly Met Arg Glu Asp Pro Ser Val Lys Gln Ile
                85                  90                  95
```

Thr Ala Gly Thr Tyr Asn Thr Thr Gly Asp Ala Asn Asn Lys Asn Gln
            100                 105                 110

Leu Asn Asn Thr Leu Gln Gln Thr Leu Glu Ala Thr Gly Ile Thr
            115                 120                 125

Ser Ser Val Gly Ser Thr Asn Tyr Ala Gly Phe Ser Leu Gly Ala Asp
            130                 135                 140

Ser Val Thr Phe Ser Lys Gly Ala Gly Thr Val Lys Leu Ser Gly
145                 150                 155                 160

Val Ser Asp Ala Thr Ala Asp Thr Asp Ala Ala Thr Leu Lys Gln Val
                165                 170                 175

Lys Glu Tyr Arg Thr Thr Leu Val Gly Asp Asn Asp Ile Thr Ala Ala
            180                 185                 190

Asp Arg Ser Gly Gly Thr Ser Asn Gly Ile Thr Tyr Asn Leu Ser Leu
            195                 200                 205

Asn Lys Gly Thr Val Ser Ala Thr Glu Glu Lys Val Val Ser Gly Lys
            210                 215                 220

Thr Val Tyr Glu Ala Ile Arg Asn Ala Ile Thr Gly Asn Ile Phe Thr
225                 230                 235                 240

Ile Gly Leu Asp Asp Thr Thr Leu Asn Lys Ile Asn Asn Pro Ala Asp
                245                 250                 255

Gln Asp Leu Ser Asn Leu Ser Glu Ser Gly Lys Asn Ala Ile Thr Gly
            260                 265                 270

Leu Val Asp Val Val Lys Lys Thr Asn Ser Pro Ile Thr Val Glu Pro
            275                 280                 285

Ser Thr Asp Ser Asn Lys Lys Lys Thr Phe Thr Val Gly Val Asp Phe
            290                 295                 300

Thr Asp Thr Ile Thr Glu Gly Asp Ala Thr Asp Asp Lys Lys Leu Thr
305                 310                 315                 320

Thr Ser Lys Ser Val Glu Ser Tyr Val Thr Asn Lys Leu Ala Asn Phe
                325                 330                 335

Ser Thr Asp Ile Leu Leu Ser Asp Gly Arg Ser Gly Asn Ala Thr Thr
            340                 345                 350

Ala Asn Asp Gly Val Gly Lys Arg Arg Leu Ser Asp Gly Phe Thr Ile
            355                 360                 365

Lys Ser Glu Asn Phe Thr Leu Gly Ser Lys Gln Tyr Asn Gly Ser Asp
            370                 375                 380

Ser Leu Gly Val Met Tyr Asp Asp Gln Asn Gly Val Phe Lys Leu Ser
385                 390                 395                 400

Leu Asn Met Thr Ala Leu Thr Thr Ser Leu Ala Asn Thr Phe Ala Lys
                405                 410                 415

Leu Asp Ala Ser Asn Leu Thr Asp Asp Ser Asn Lys Glu Lys Trp Arg
            420                 425                 430

Thr Ala Leu Asn Val Tyr Ser Lys Thr Glu Val Asp Ala Glu Ile Gln
            435                 440                 445

Lys Ser Lys Val Thr Leu Thr Pro Asp Ser Gly Leu Ile Phe Ala Thr
            450                 455                 460

Lys Gln Ala Gly Ser Gly Asn Asn Ala Gly Ile Asp Ala Gly Asn Lys
465                 470                 475                 480

Lys Ile Ser Asn Val Ala Asp Gly Asp Ile Ser Pro Thr Ser Gly Asp
                485                 490                 495

Val Val Thr Gly Arg Gln Leu Tyr Ala Leu Met Gln Lys Gly Ile Arg
            500                 505                 510

Val Tyr Gly Asp Glu Val Ser Pro Thr Lys Thr Gln Thr Thr Ala Pro

```
                515                 520                 525
Thr Asn Ala Asn Pro Thr Ala Thr Thr Ala Pro Thr Ala Ser Ser Thr
        530                 535                 540
Gln Gly Gly Ser Leu Ile Ser Leu Ser Ala Thr Glu Glu Glu Val
545                 550                 555                 560
Val Ser Gly Glu Ala Val Tyr Asp Ala Leu Lys Gly Ala Lys Pro Thr
                565                 570                 575
Val Ser Ala Glu Ala Asn Lys Gly Ile Thr Gly Leu Val Asp Val Val
                580                 585                 590
Lys Lys Ala Asn Ser Pro Ile Thr Val Glu Pro Ser Thr Asp Asn Asn
            595                 600                 605
Lys Lys Lys Thr Phe Thr Val Gly Leu Met Lys Asp Ile Glu Gly Val
            610                 615                 620
Asn Ser Ile Thr Phe Asp Lys Ser Gly Gln Asp Leu Asn Gln Val Thr
625                 630                 635                 640
Gly Arg Met Ser Ser Ala Gly Leu Thr Phe Lys Lys Gly Asp Thr Thr
                645                 650                 655
Asn Gly Ser Thr Thr Thr Phe Ala Glu Asp Gly Leu Thr Ile Asp Ser
                660                 665                 670
Thr Thr Asn Ser Ala Gln Thr Asn Leu Val Lys Val Ser Arg Asp Gly
            675                 680                 685
Phe Ser Val Lys Asn Gly Ser Asp Glu Ser Lys Leu Ala Ser Thr Lys
690                 695                 700
Leu Ser Ile Gly Ala Glu Asn Ala Glu His Val Glu Val Thr Lys Ser
705                 710                 715                 720
Gly Ile Ala Leu Lys Ala Asp Asn Thr Ser Asp Lys Ser Ser Ile Thr
                725                 730                 735
Leu Ala Gln Asp Ala Ile Thr Leu Ala Gly Asn Ala Thr Gly Thr Ala
                740                 745                 750
Ile Lys Leu Thr Gly Val Ala Asp Gly Asn Ile Thr Val Asn Ser Lys
            755                 760                 765
Asp Ala Val Asn Gly Gly Gln Leu Arg Thr Leu Leu Gly Val Asp Ser
770                 775                 780
Gly Ala Lys Ile Gly Gly Thr Glu Lys Thr Thr Ile Ser Glu Ala Ile
785                 790                 795                 800
Ser Asp Val Lys Gln Ala Leu Thr Asp Ala Thr Leu Ala Tyr Lys Ala
                805                 810                 815
Asp Asn Lys Asn Gly Lys Thr Val Lys Leu Thr Asp Gly Leu Asn Phe
                820                 825                 830
Thr Ser Thr Thr Asn Ile Asp Ala Ser Val Glu Asp Asn Gly Val Val
                835                 840                 845
Lys Phe Thr Leu Lys Asp Lys Leu Thr Gly Leu Lys Thr Ile Ala Thr
            850                 855                 860
Glu Ser Leu Asn Ala Ser Gln Asn Ile Ile Ala Gly Gly Thr Val Thr
865                 870                 875                 880
Val Gly Gly Glu Thr Glu Gly Ile Val Leu Thr Lys Ser Gly Ser Gly
                885                 890                 895
Asn Asp Arg Thr Leu Ser Leu Ser Gly Ala Gly Asn Ala Ala Thr Asp
                900                 905                 910
Gly Ile Lys Val Ser Gly Val Lys Ala Gly Thr Ala Asp Thr Asp Ala
            915                 920                 925
Val Asn Lys Gly Gln Leu Asp Lys Leu Phe Lys Ala Ile Asn Asp Ala
            930                 935                 940
```

```
Leu Gly Thr Thr Asp Leu Ala Val Thr Lys Asn Pro Asn Gln Thr Ser
945                 950                 955                 960

Ile Phe Asn Pro Ile Asn Gly Thr Ala Pro Thr Thr Phe Lys Asp Ala
                965                 970                 975

Val Asp Lys Leu Thr Thr Ala Val Asn Thr Gly Trp Gly Ser
            980                 985                 990

<210> SEQ ID NO 65
<211> LENGTH: 789
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: A fusion peptide consisting of membrane protein
      sections from each of Avibacterium paragallinarum types A and C

<400> SEQUENCE: 65

Met Asp Gly Thr Ile Thr Phe Thr Asn Ile Gly Gly Thr Gly Gln Ala
1               5                   10                  15

Thr Ile His Asp Ala Ile Asn Asn Val Leu Thr Lys Gly Ile Tyr Leu
            20                  25                  30

Lys Ala Asp Gln Asn Asp Pro Thr Gly Asn Gln Gly Gln Lys Val Glu
        35                  40                  45

Leu Gly Asn Ala Ile Thr Leu Ser Ala Thr Asn Gln Trp Ala Asn Asn
50                  55                  60

Gly Val Asn Tyr Lys Thr Asn Asn Leu Thr Thr Tyr Asn Ser Gln Asn
65                  70                  75                  80

Gly Thr Ile Leu Phe Gly Met Arg Glu Asp Pro Ser Val Lys Gln Ile
                85                  90                  95

Thr Ala Gly Thr Tyr Asn Thr Thr Gly Asp Ala Asn Asn Lys Asn Gln
            100                 105                 110

Leu Asn Asn Thr Leu Gln Gln Thr Thr Leu Glu Ala Thr Gly Ile Thr
        115                 120                 125

Ser Ser Val Gly Ser Thr Asn Tyr Ala Gly Phe Ser Leu Gly Ala Asp
130                 135                 140

Ser Val Thr Phe Ser Lys Gly Gly Ala Gly Thr Val Lys Leu Ser Gly
145                 150                 155                 160

Val Ser Asp Ala Thr Ala Asp Thr Asp Ala Ala Thr Leu Lys Gln Val
                 165                 170                 175

Lys Glu Tyr Arg Thr Thr Leu Val Gly Asp Asn Asp Ile Thr Ala Ala
            180                 185                 190

Asp Arg Ser Gly Gly Thr Ser Asn Gly Ile Thr Tyr Asn Leu Ser Leu
        195                 200                 205

Asn Lys Gly Thr Val Ser Ala Thr Glu Glu Lys Val Val Ser Gly Lys
210                 215                 220

Thr Val Tyr Glu Ala Ile Arg Asn Ala Ile Thr Gly Asn Ile Phe Thr
225                 230                 235                 240

Ile Gly Leu Asp Asp Thr Thr Leu Asn Lys Ile Asn Asn Pro Ala Asp
                245                 250                 255

Gln Asp Leu Ser Asn Leu Ser Glu Ser Gly Lys Asn Ala Ile Thr Gly
            260                 265                 270

Leu Val Asp Val Val Lys Lys Thr Asn Ser Pro Ile Thr Val Glu Pro
        275                 280                 285

Ser Thr Asp Ser Asn Lys Lys Lys Thr Phe Thr Val Gly Val Asp Phe
290                 295                 300
```

-continued

Thr Asp Thr Ile Thr Glu Gly Asp Ala Thr Asp Asp Lys Lys Leu Thr
305                 310                 315                 320

Thr Ser Lys Ser Val Glu Ser Tyr Val Thr Asn Lys Leu Ala Asn Phe
            325                 330                 335

Ser Thr Asp Ile Leu Leu Ser Asp Gly Arg Ser Gly Asn Ala Thr Thr
        340                 345                 350

Ala Asn Asp Gly Val Gly Lys Arg Arg Leu Ser Asp Gly Phe Thr Ile
    355                 360                 365

Lys Ser Glu Asn Phe Thr Leu Gly Ser Lys Gln Tyr Asn Gly Ser Asp
370                 375                 380

Ser Leu Gly Val Met Tyr Asp Asp Gln Asn Gly Val Phe Lys Leu Ser
385                 390                 395                 400

Leu Asn Met Thr Ala Leu Thr Thr Ser Leu Ala Asn Thr Phe Ala Lys
            405                 410                 415

Leu Asp Ala Ser Asn Leu Thr Asp Asp Ser Asn Lys Glu Lys Trp Arg
        420                 425                 430

Thr Ala Leu Asn Val Tyr Ser Lys Thr Glu Val Asp Ala Glu Ile Gln
    435                 440                 445

Lys Ser Lys Val Thr Leu Thr Pro Asp Ser Gly Leu Ile Phe Ala Thr
450                 455                 460

Lys Gln Ala Gly Ser Gly Asn Asn Ala Gly Ile Asp Ala Gly Asn Lys
465                 470                 475                 480

Lys Ile Ser Asn Val Ala Asp Gly Asp Ile Ser Pro Thr Ser Gly Asp
            485                 490                 495

Val Val Thr Gly Arg Gln Leu Tyr Ala Leu Met Gln Lys Gly Ile Arg
        500                 505                 510

Val Tyr Gly Asp Glu Val Ser Pro Thr Lys Thr Gln Thr Thr Ala Pro
    515                 520                 525

Thr Asn Ala Asn Pro Thr Ala Thr Thr Ala Pro Thr Ala Ser Ser Thr
530                 535                 540

Gln Gly Gly Ser Leu Ile Ser Leu Ser Ala Thr Glu Glu Glu Glu Val
545                 550                 555                 560

Val Ser Gly Glu Ala Val Tyr Asp Ala Leu Lys Gly Ala Lys Pro Thr
            565                 570                 575

Val Ser Ala Glu Ala Asn Lys Gly Ile Thr Gly Leu Val Asp Val Val
        580                 585                 590

Lys Lys Ala Asn Ser Pro Ile Thr Val Glu Pro Ser Thr Asp Asn Asn
    595                 600                 605

Lys Lys Lys Thr Phe Thr Val Gly Leu Met Lys Asp Ile Glu Gly Val
610                 615                 620

Asn Ser Ile Thr Phe Asp Lys Ser Gly Gln Asp Leu Asn Gln Val Thr
625                 630                 635                 640

Gly Arg Met Ser Ser Ala Gly Leu Thr Phe Lys Lys Gly Asp Thr Thr
            645                 650                 655

Asn Gly Ser Thr Thr Thr Phe Ala Glu Asp Gly Leu Thr Ile Asp Ser
        660                 665                 670

Thr Thr Asn Ser Ala Gln Thr Asn Leu Val Lys Val Ser Arg Asp Gly
    675                 680                 685

Phe Ser Val Lys Asn Gly Ser Asp Glu Ser Lys Leu Ala Ser Thr Lys
690                 695                 700

Leu Ser Ile Gly Ala Glu Asn Ala Glu His Val Glu Val Thr Lys Ser
705                 710                 715                 720

Gly Ile Ala Leu Lys Ala Asp Asn Thr Ser Asp Lys Ser Ser Ile Thr
            725                 730                 735

```
Leu Ala Gln Asp Ala Ile Thr Leu Ala Gly Asn Ala Thr Gly Thr Ala
            740                 745                 750

Ile Lys Leu Thr Gly Val Ala Asp Gly Asn Ile Thr Val Asn Ser Lys
            755                 760                 765

Asp Ala Val Asn Gly Gly Leu Arg Thr Leu Leu Gly Val Asp Ser
            770                 775                 780

Gly Ala Lys Ile Gly
785

<210> SEQ ID NO 66
<211> LENGTH: 923
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: A fusion peptide consisting of membrane protein
      sections from each of Avibacterium paragallinarum types A and C

<400> SEQUENCE: 66

Met Asp Gly Thr Ile Thr Phe Thr Asn Ile Gly Gly Thr Gly Gln Ala
1               5                   10                  15

Thr Ile His Asp Ala Ile Asn Asn Val Leu Thr Lys Gly Ile Tyr Leu
            20                  25                  30

Lys Ala Asp Gln Asn Asp Pro Thr Gly Asn Gln Gly Gln Lys Val Glu
            35                  40                  45

Leu Gly Asn Ala Ile Thr Leu Ser Ala Thr Asn Gln Trp Ala Asn Asn
    50                  55                  60

Gly Val Asn Tyr Lys Thr Asn Asn Leu Thr Thr Tyr Asn Ser Gln Asn
65                  70                  75                  80

Gly Thr Ile Leu Phe Gly Met Arg Glu Asp Pro Ser Val Lys Gln Ile
                85                  90                  95

Thr Ala Gly Thr Tyr Asn Thr Thr Gly Asp Ala Asn Asn Lys Asn Gln
            100                 105                 110

Leu Asn Asn Thr Leu Gln Gln Thr Thr Leu Glu Ala Thr Gly Ile Thr
            115                 120                 125

Ser Ser Val Gly Ser Thr Asn Tyr Ala Gly Phe Ser Leu Gly Ala Asp
    130                 135                 140

Ser Val Thr Phe Ser Lys Gly Gly Ala Gly Thr Val Lys Leu Ser Gly
145                 150                 155                 160

Val Ser Asp Ala Thr Ala Asp Thr Asp Ala Ala Thr Leu Lys Gln Val
                165                 170                 175

Lys Glu Tyr Arg Thr Thr Leu Val Gly Asp Asn Asp Ile Thr Ala Ala
            180                 185                 190

Asp Arg Ser Gly Gly Thr Ser Asn Gly Ile Thr Tyr Asn Leu Ser Leu
            195                 200                 205

Asn Lys Gly Thr Val Ser Ala Thr Glu Glu Lys Val Val Ser Gly Lys
    210                 215                 220

Thr Val Tyr Glu Ala Ile Arg Asn Ala Ile Thr Gly Asn Ile Phe Thr
225                 230                 235                 240

Ile Gly Leu Asp Asp Thr Thr Leu Asn Lys Ile Asn Asn Pro Ala Asp
                245                 250                 255

Gln Asp Leu Ser Asn Leu Ser Glu Ser Gly Lys Asn Ala Ile Thr Gly
            260                 265                 270

Leu Val Asp Val Val Lys Lys Thr Asn Ser Pro Ile Thr Val Glu Pro
            275                 280                 285
```

Ser Thr Asp Ser Asn Lys Lys Lys Thr Phe Thr Val Gly Val Asp Phe
290                 295                 300

Thr Asp Thr Ile Thr Glu Gly Asp Ala Thr Asp Asp Lys Lys Leu Thr
305                 310                 315                 320

Thr Ser Lys Ser Val Glu Ser Tyr Val Thr Asn Lys Leu Ala Asn Phe
            325                 330                 335

Ser Thr Asp Ile Leu Leu Ser Asp Gly Arg Ser Gly Asn Ala Thr Thr
                340                 345                 350

Ala Asn Asp Gly Val Gly Lys Arg Arg Leu Ser Asp Gly Phe Thr Ile
            355                 360                 365

Lys Ser Glu Asn Phe Thr Leu Gly Ser Lys Gln Tyr Asn Gly Ser Asp
370                 375                 380

Ser Leu Gly Val Met Tyr Asp Asp Gln Asn Gly Val Phe Lys Leu Ser
385                 390                 395                 400

Leu Asn Met Thr Ala Leu Thr Thr Ser Leu Ala Asn Thr Phe Ala Lys
                405                 410                 415

Leu Asp Ala Ser Asn Leu Thr Asp Asp Ser Asn Lys Glu Lys Trp Arg
            420                 425                 430

Thr Ala Leu Asn Val Tyr Ser Lys Thr Glu Val Asp Ala Glu Ile Gln
            435                 440                 445

Lys Ser Lys Val Thr Leu Thr Pro Asp Ser Gly Leu Ile Phe Ala Thr
450                 455                 460

Lys Gln Ala Gly Ser Gly Asn Asn Ala Gly Ile Asp Ala Gly Asn Lys
465                 470                 475                 480

Lys Ile Ser Asn Val Ala Asp Gly Asp Ile Ser Pro Thr Ser Gly Asp
                485                 490                 495

Val Val Thr Gly Arg Gln Leu Tyr Ala Leu Met Gln Lys Gly Ile Arg
            500                 505                 510

Val Tyr Gly Asp Glu Val Ser Pro Thr Lys Thr Gln Thr Thr Ala Pro
            515                 520                 525

Thr Asn Ala Asn Pro Thr Ala Thr Thr Ala Pro Thr Ala Ser Ser Thr
530                 535                 540

Gln Gly Gly Ser Gly Leu Met Lys Asp Ile Glu Gly Val Asn Ser Ile
545                 550                 555                 560

Thr Phe Asp Lys Ser Gly Gln Asp Leu Asn Gln Val Thr Gly Arg Met
                565                 570                 575

Ser Ser Ala Gly Leu Thr Phe Lys Lys Gly Asp Thr Thr Asn Gly Ser
            580                 585                 590

Thr Thr Thr Phe Ala Glu Asp Gly Leu Thr Ile Asp Ser Thr Thr Asn
            595                 600                 605

Ser Ala Gln Thr Asn Leu Val Lys Val Ser Arg Asp Gly Phe Ser Val
610                 615                 620

Lys Asn Gly Ser Asp Glu Ser Lys Leu Ala Ser Thr Lys Leu Ser Ile
625                 630                 635                 640

Gly Ala Glu Asn Ala Glu His Val Glu Val Thr Lys Ser Gly Ile Ala
                645                 650                 655

Leu Lys Ala Asp Asn Thr Ser Asp Lys Ser Ser Ile Thr Leu Ala Gln
            660                 665                 670

Asp Ala Ile Thr Leu Ala Gly Asn Ala Thr Gly Thr Ala Ile Lys Leu
            675                 680                 685

Thr Gly Val Ala Asp Gly Asn Ile Thr Val Asn Ser Lys Asp Ala Val
690                 695                 700

Asn Gly Gly Gln Leu Arg Thr Leu Leu Gly Val Asp Ser Gly Ala Lys

```
                705                 710                 715                 720
Ile Gly Gly Thr Glu Lys Thr Thr Ile Ser Glu Ala Ile Ser Asp Val
                    725                 730                 735

Lys Gln Ala Leu Thr Asp Ala Thr Leu Ala Tyr Lys Ala Asp Asn Lys
                    740                 745                 750

Asn Gly Lys Thr Val Lys Leu Thr Asp Gly Leu Asn Phe Thr Ser Thr
                    755                 760                 765

Thr Asn Ile Asp Ala Ser Val Glu Asp Asn Gly Val Val Lys Phe Thr
        770                 775                 780

Leu Lys Asp Lys Leu Thr Gly Leu Lys Thr Ile Ala Thr Glu Ser Leu
785                 790                 795                 800

Asn Ala Ser Gln Asn Ile Ile Ala Gly Gly Thr Val Thr Val Gly Gly
                    805                 810                 815

Glu Thr Glu Gly Ile Val Leu Thr Lys Ser Gly Ser Gly Asn Asp Arg
                    820                 825                 830

Thr Leu Ser Leu Ser Gly Ala Gly Asn Ala Ala Thr Asp Gly Ile Lys
            835                 840                 845

Val Ser Gly Val Lys Ala Gly Thr Ala Asp Thr Asp Ala Val Asn Lys
850                 855                 860

Gly Gln Leu Asp Lys Leu Phe Lys Ala Ile Asn Asp Ala Leu Gly Thr
865                 870                 875                 880

Thr Asp Leu Ala Val Thr Lys Asn Pro Asn Gln Thr Ser Ile Phe Asn
                    885                 890                 895

Pro Ile Asn Gly Thr Ala Pro Thr Thr Phe Lys Asp Ala Val Asp Lys
                    900                 905                 910

Leu Thr Thr Ala Val Asn Thr Gly Trp Gly Ser
            915                 920

<210> SEQ ID NO 67
<211> LENGTH: 722
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: A fusion peptide consisting of membrane protein
      sections from each of Avibacterium paragallinarum types A and C

<400> SEQUENCE: 67

Met Asp Gly Thr Ile Thr Phe Thr Asn Ile Gly Gly Thr Gly Gln Ala
1               5                   10                  15

Thr Ile His Asp Ala Ile Asn Asn Val Leu Thr Lys Gly Ile Tyr Leu
            20                  25                  30

Lys Ala Asp Gln Asn Asp Pro Thr Gly Asn Gln Gly Lys Val Glu
        35                  40                  45

Leu Gly Asn Ala Ile Thr Leu Ser Ala Thr Asn Gln Trp Ala Asn Asn
    50                  55                  60

Gly Val Asn Tyr Lys Thr Asn Asn Leu Thr Thr Tyr Asn Ser Gln Asn
65                  70                  75                  80

Gly Thr Ile Leu Phe Gly Met Arg Glu Asp Pro Ser Val Lys Gln Ile
                85                  90                  95

Thr Ala Gly Thr Tyr Asn Thr Thr Gly Asp Ala Asn Asn Lys Asn Gln
            100                 105                 110

Leu Asn Asn Thr Leu Gln Gln Thr Thr Leu Glu Ala Thr Gly Ile Thr
        115                 120                 125

Ser Ser Val Gly Ser Thr Asn Tyr Ala Gly Phe Ser Leu Gly Ala Asp
```

```
                130              135              140
Ser Val Thr Phe Ser Lys Gly Gly Ala Gly Thr Val Lys Leu Ser Gly
145                 150                 155                 160

Val Ser Asp Ala Thr Ala Asp Thr Asp Ala Ala Thr Leu Lys Gln Val
                165                 170                 175

Lys Glu Tyr Arg Thr Thr Leu Val Gly Asp Asn Asp Ile Thr Ala Ala
                180                 185                 190

Asp Arg Ser Gly Gly Thr Ser Asn Gly Ile Thr Tyr Asn Leu Ser Leu
                195                 200                 205

Asn Lys Gly Thr Val Ser Ala Thr Glu Glu Lys Val Val Ser Gly Lys
                210                 215                 220

Thr Val Tyr Glu Ala Ile Arg Asn Ala Ile Thr Gly Asn Ile Phe Thr
225                 230                 235                 240

Ile Gly Leu Asp Asp Thr Thr Leu Asn Lys Ile Asn Asn Pro Ala Asp
                245                 250                 255

Gln Asp Leu Ser Asn Leu Ser Glu Ser Gly Lys Asn Ala Ile Thr Gly
                260                 265                 270

Leu Val Asp Val Val Lys Lys Thr Asn Ser Pro Ile Thr Val Glu Pro
                275                 280                 285

Ser Thr Asp Ser Asn Lys Lys Lys Thr Phe Thr Val Gly Val Asp Phe
290                 295                 300

Thr Asp Thr Ile Thr Glu Gly Asp Ala Thr Asp Lys Lys Leu Thr
305                 310                 315                 320

Thr Ser Lys Ser Val Glu Ser Tyr Val Thr Asn Lys Leu Ala Asn Phe
                325                 330                 335

Ser Thr Asp Ile Leu Leu Ser Asp Gly Arg Ser Gly Asn Ala Thr Thr
                340                 345                 350

Ala Asn Asp Gly Val Gly Lys Arg Arg Leu Ser Asp Gly Phe Thr Ile
                355                 360                 365

Lys Ser Glu Asn Phe Thr Leu Gly Ser Lys Gln Tyr Asn Gly Ser Asp
                370                 375                 380

Ser Leu Gly Val Met Tyr Asp Asp Gln Asn Gly Val Phe Lys Leu Ser
385                 390                 395                 400

Leu Asn Met Thr Ala Leu Thr Thr Ser Leu Ala Asn Thr Phe Ala Lys
                405                 410                 415

Leu Asp Ala Ser Asn Leu Thr Asp Asp Ser Asn Lys Glu Lys Trp Arg
                420                 425                 430

Thr Ala Leu Asn Val Tyr Ser Lys Thr Glu Val Asp Ala Glu Ile Gln
                435                 440                 445

Lys Ser Lys Val Thr Leu Thr Pro Asp Ser Gly Leu Ile Phe Ala Thr
450                 455                 460

Lys Gln Ala Gly Ser Gly Asn Asn Ala Gly Ile Asp Ala Gly Asn Lys
465                 470                 475                 480

Lys Ile Ser Asn Val Ala Asp Gly Asp Ile Ser Pro Thr Ser Gly Asp
                485                 490                 495

Val Val Thr Gly Arg Gln Leu Tyr Ala Leu Met Gln Lys Gly Ile Arg
                500                 505                 510

Val Tyr Gly Asp Glu Val Ser Pro Thr Lys Thr Gln Thr Thr Ala Pro
                515                 520                 525

Thr Asn Ala Asn Pro Thr Ala Thr Thr Ala Pro Thr Ala Ser Ser Thr
                530                 535                 540

Gln Gly Gly Ser Gly Leu Met Lys Asp Ile Glu Gly Val Asn Ser Ile
545                 550                 555                 560
```

```
Thr Phe Asp Lys Ser Gly Gln Asp Leu Asn Gln Val Thr Gly Arg Met
            565                 570                 575
Ser Ser Ala Gly Leu Thr Phe Lys Lys Gly Asp Thr Thr Asn Gly Ser
            580                 585                 590
Thr Thr Thr Phe Ala Glu Asp Gly Leu Thr Ile Asp Ser Thr Thr Asn
            595                 600                 605
Ser Ala Gln Thr Asn Leu Val Lys Val Ser Arg Asp Gly Phe Ser Val
            610                 615                 620
Lys Asn Gly Ser Asp Glu Ser Lys Leu Ala Ser Thr Lys Leu Ser Ile
625                 630                 635                 640
Gly Ala Glu Asn Ala Glu His Val Glu Val Thr Lys Ser Gly Ile Ala
            645                 650                 655
Leu Lys Ala Asp Asn Thr Ser Asp Lys Ser Ser Ile Thr Leu Ala Gln
            660                 665                 670
Asp Ala Ile Thr Leu Ala Gly Asn Ala Thr Gly Thr Ala Ile Lys Leu
            675                 680                 685
Thr Gly Val Ala Asp Gly Asn Ile Thr Val Asn Ser Lys Asp Ala Val
            690                 695                 700
Asn Gly Gly Gln Leu Arg Thr Leu Leu Gly Val Asp Ser Gly Ala Lys
705                 710                 715                 720
Ile Gly

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Gly Gly Gly Gly Gly Gly Gly Gly Gly
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Met Arg Gly Ser His His His His His His Gly Ser
1               5                   10
```